US006610828B1

(12) United States Patent
Jepson et al.

(10) Patent No.: US 6,610,828 B1
(45) Date of Patent: Aug. 26, 2003

(54) HELIOTHIS ECDYSONE RECEPTOR

(75) Inventors: Ian Jepson, Maidenhead (GB); Alberto Martinez, Binfield (GB); Andrew James Greenland, Maidenhead (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 09/564,418

(22) Filed: May 3, 2000

Related U.S. Application Data

(62) Division of application No. 08/653,648, filed on May 24, 1996, now Pat. No. 6,379,945.

(51) Int. Cl.$^7$ .......................... C07K 1/00; C07K 14/00; C07K 17/00
(52) U.S. Cl. ........................................... 530/350
(58) Field of Search ......................................... 530/350

(56) References Cited

U.S. PATENT DOCUMENTS 5,424,333 A    6/1995   Wing .......................... 514/615
5,514,578 A  * 5/1996   Hogness et al.

FOREIGN PATENT DOCUMENTS

| EP | 0 218 571 | 4/1987 |
| EP | 0 293 358 | 11/1988 |
| EP | 0 615 976 | 9/1994 |
| WO | 90/08826 | 8/1990 |
| WO | 90/14000 | 11/1990 |
| WO | 91/04323 | 4/1991 |
| WO | 91/13167 | 9/1991 |
| WO | 92/003777 | 1/1992 |
| WO | 92/04449 | 3/1992 |
| WO | 92/06201 | 4/1992 |
| WO | 93/03162 | 2/1993 |
| WO | 93/09237 | 5/1993 |
| WO | 93/23431 | 11/1993 |
| WO | 96/27673 | 9/1996 |

OTHER PUBLICATIONS

Ayala et al. (1980) Modern Genetics, The Benjamin Cummings publishing company, Inc., p. 45.*

Allan, George F. et al., Ligand–dependent conformational changes in the pro–gesterone receptor are necessary for events that follow DNA binding, Proc. Natl. Acad. Sci., USA, Biochemistry, vol. 89, Dec. 1992, pp. 11750–11754.

Allan, George F. et al., "Hormone and Antihormone Induce Distinct Conforma–tional Changes Which Are Central to Steroid Receptor Activation", The Journal of Biological Chemistry, vol. 267, No. 27, Sep. 1992, pp. 19513–19520.

Ashburner, Michael, "Puffs, Genes, and Hormones Revisited", Cell, vol. 61, Apr. 6, 1990, pp. 1–3.

Beato, Miguel, "Gene Regulation by Steroid Hormones", Cell, vol. 56, Feb. 10, 1989, pp. 335–344.

Becker, Claudia et al., "PCR cloning and expression analysis of cDNAs encoding cysteine proteinases from germinating seeds of *Vicia sativa* L.", Plant Molecular Biology, vol. 26, 1994, pp. 1207–1212.

Cammue, Bruno P.A. et al., "Isolation and Characterization of a Novel Class of Plant Antimicrobial Peptides from *Mirabilis jalapa* L. Seeds", The Journal of Biological Chemistry, vol. 267, No. 4, Feb. 1992, pp. 2228–2233.

Carlberg, Carsten et al., "Two nuclear signalling pathways for vitamin D", Nature, vol. 361, Feb. 18, 1993, pp. 657–660.

Cho, Wen–Long et al., "Mosquito Ecdysteroid Receptor: Analysis of the cDNA and Expression During Vitellogenesis", Insect Biochem. Molec. Biol., vol. 25, No. 1, 1995, pp. 19–27.

Christopherson, Karen S. et al., "Ecdysteroid–dependent regulation of genes in mammalian cells by a *Drosophila* ecdysone receptor and chimeric transactiva–tors", Proc. Natl. Acad. Sci., USA, Genetics, vol. 89, Jul. 1992, pp. 6314–6318.

Evans, Ronald M., "The Steroid and Thyroid Hormone Receptor Superfamily", Science, vol. 240, May 13, 1988, pp. 889–895.

Goetting–Minesky, M.P. et al., "Differential gene expression in an actinohizal symbiosis: Evidence for a nodule–specific cysteine proteinase", Proc. Natl. Acad. Sci., USA, Plant Biology, vol. 91, Oct. 1994, pp. 9891–9895.

Green, Stephen et al., "Nuclear receptors enhance our understanding of trans–cription regulation", TIG, vol. 4, No. 11, Nov. 1988, pp. 309–314.

Heyman, Richard A. et al., "9–Cis Retinoic Acid Is a High Affinity Ligand for the Retinoid X Receptor", Cell, vol. 68, Jan. 24, 1992, pp. 397–406.

Hirst, M.C. et al., "Preparation of radiolabelled hybridization probes by STS labelling", Trends in Genetics, vol. 8, No. 1, Jan. 1992, pp. 6–7.

Hollenberg, Stanley M. et al., "Primary structure and expression of a functional human glucocorticoid receptor cDNA", Nature, vol. 318, No. 19, Dec. 16, 1985, pp. 635–641.

Imhog, Markus O. et al., Cloning of a *Chironomus tentans* Cdna Encoding a Protein (cEcRH) Homologous to the *Drosophila melanogaster* Ecdysteroid Receptor (dEcR), Insect Biochem. Molec. Biol., vol. 23, No. 1, Jan. 1993, pp. 115–124.

Primary Examiner—Michael Pak
(74) Attorney, Agent, or Firm—Jenkins, Wilson & Taylor, P.A.

(57) ABSTRACT

The invention relates to an insect steroid receptor protein which is capable of acting as a gene switch which is responsive to a chemical inducer enabling external control of the gene.

7 Claims, 57 Drawing Sheets

OTHER PUBLICATIONS

Jiang, Binghua et al., "Association of a 33–Kilodalton Cysteine Proteinase Found in Corn Callus with the Inhibition of Fall Armyworm Larval Growth", Plant Physiol., vol. 108, 1995, pp. 1631–1640.

Jindra, Marek et al., "Isolation and Developmental Expression of the Ecdysteroid–induced GHR3 Gene of the Wax Moth *Galleria mellonella*", Insect Biochem. Molec. Biol., vol. 24, No. 8, 1994, pp. 763–773.

Kliewer, Steven A. et al., "Retinoid X receptor interacts with nuclear receptors in retinoic acid, thyroid hormone and vitamin $D_3$ signalling", Nature, vol. 355, Jan. 30, 1992, pp. 446–449.

Koelle, Michael R. et al., "The Drosophila EcR Gene Encodes and Ecdysone Receptor, a New Member of the Steroid Receptor Superfamily", Cell, vol. 67, Oct. 4, 1991, pp. 59–77.

Kothapalli, Ravi et al., "Cloning and Developmental Expression of the Ecdysone Receptor Gene From the Spruce Budworm, Choristoneura fumiferana", Developmental Genetics, vol. 17, 1995, pp. 319–330.

Krust, Andréet al., "The chicken oestrogen receptor sequence: homology with v–erbA and the human oestrogen and glucocorticoid receptors", The EMBO Journal, vol. 5, No. 5, 1986, pp. 891–897.

Leid, Mark et al., "Multiplicity generates diversity in the retinoic acid signally path–ways", TIBS, vol. 17, Oct. 1992, pp. 427–433.

Leid, Mark et al., "Purification, Cloning, and RXR Identity of the HeLa Cell Factor with Which RAR or TR Heterodimerizes to Bind Target Sequences Efficiently", Cell, vol. 68, Jan. 24, 1992, pp. 377–395.

Linthorst, Huub J. et al., "Circadian expression and induction by wounding of tobacco genes for cysteine proteinase", Plant Molecular Biology, vol. 21, 1993, pp. 685–694.

Mangelsdorf, David J. et al., "Characterization of three RXR genes that mediate the action of 9–cis retinoic acid", Genes & Development, vol. 6, 1992, pp. 329–344.

Oro, Anthony E. et al., "Relationship between the product of the *Drosophila ultraspiracle* locus and the vertebrate retinoid X receptor", Nature, vol. 347, Sep. 20, 1990, pp. 298–301.

Riddihough et al., "An ecdysone response element in the Drosophila hsp27 promoter", The EMBO Journal, vol. 6, No. 12, 1987, pp. 3729–3734.

Schena, Mark et al., "A steroid–inducible gene expression system for plant cells", Proc. Natl. Acad. Sci., USA, Genetics, vol. 88, Dec. 1991, pp. 10421–10425.

Segraves, William A., "Something Old, Some Things New: The Steroid Receptor Superfamily in Drosophila", Cell, vol. 67, Oct. 18, 1991, pp. 225–228.

Segraves, William A. et al., "The E75 ecdysone–inducible gene responsible for the 75B early puff in Drosophila encodes two new members of the steroid receptor superfamily", Genes & Development, vol. 4, 1990, pp. 204–219.

Smagghe, Guy et al., "Action of a Novel Nonsteroidal Ecdysteroid Mimic, Tebufenozide (RH–5992), on Insects of Different Orders", Pestic. Sci., vol. 42, 1994, pp. 85–92.

Smagghe, Guy et al., "Biological activity and receptor–binding of ecdysteroids and the ecdysteroid agonists RH–5849 and RH–5992 in imaginal wing discs of *Spodoptera exigua* (Lepidoptera:Noctuidae)", Eur. J. Entomol., vol. 92, 1995, pp. 333–340.

Smart, Catherine M. et al., "The timing of maize leaf senescene and characteri–sation of senescene–related cDNAs", Physiologia Plantarum, vol. 93, 1995, pp. 673–682.

Stemmer, Willem P.C., "Rapid evolution of a protein in vitro by DNA shuffling", Nature, vol. 370, Aug. 4, 1994, pp. 389–391.

Terras, Franky R.G. et al., "A new family of basic cysteine–rich plant antifungal proteins from Brassicaceae species", FEBS Letters, vol. 316, No. 3, pp. 233–240.

Thummel, Carl S. et al., "Spatial and Temporal Patterns of E74 Transcription during Drosophila Development", Cell, vol. 61, Apr. 6, 1990, pp. 101–111.

Vegeto, Elisabetta et al., "The Mechanism of RU486 Antagonism Is Dependent on the Conformation of the Carboxy–Terminal Tail of the Human Progesterone Receptor", Cell, vol. 69, May 15, 1992, pp. 703–713.

Yao, Tso–Pang et al., "Drosophila ultraspiracle Modulates Ecdysone Receptor Function via Heterodimer Formation", Cell, vol. 71, Oct. 2, 1992, pp. 63–72.

Yao, Tso–Pang et al., "Functional ecdysone receptor is the product of EcR and Ultraspiracle genes", Nature, vol. 366, Dec. 2, 1993, pp. 476–479.

Yu, Victor C. et al., "RXRβ: A Coregulator That Enhances Binding of Retinoic Acid, Thyroid Hormone, and Vitamin D receptors to Their Cognate Response Elements", Cell, vol. 67, Dec. 20, 1991, pp. 1251–1266.

Hogness, D.S., Talbot, W.S., Bender, M.T. and Koelle, M. [1992] X Ecdysone Workshop, Liverpool. (Abstract).

Bowie et al. (1990) Science 247: 1307–1310.

George et al. (1988) Macromolecular Sequencing and Synthesis (Ed. D.H. Schlesinger) Alan R. Liss Inc., New York, pp. 127–149.

* cited by examiner

Fig.1.

Sequence ID 1

```
1    TGCG AGG GGT GCA AGG AGT TCT TCA GGC GGA GTG TAA CCA AAA ATG
     ACGC TCC CCA CGT TCC TCA AGA AGT CCG CCT CAC ATT GGT TTT TAC

46   CAG TGT ACA TAT GCA AAT TCG GCC ATG CTT GCG AAA TGG ATA TGT
     GTC ACA TGT ATA CGT TTA AGC CGG TAC GAA CGC TTT ACC TAT ACA

91   ATA TGC GGA GAA AAT GCC AAG AGT A
     TAT ACG CCT CTT TTA CGG TTC TCA T
```

Fig.2.

```
Sequence ID 2

3            9           15          21          27          33          39          45
       |            |            |           |           |           |           |           |
  1  TCC ACT GGT GTT TTC ACC ACA GAA AAG GCC TCT GCT CAT TTA
     AGG TGA CCA CAA AAG TGG TGT CTT TTC CGG AGA CGA GTA AAT

46  GAG GGT GGT GCT AAG AAG GTC ATC TCC TGC CCA GCG CTG
     CTC CCA CCA CGA TTC TTC CAG AGG ACG GGT CGC GAC

91  ACC CAT GTT CGT CGT TGT CAA CCT TGA AGC AGT ATG ACC CCT
     TGG GTA CAA GCA GCA ACA GTT GGA ACT TCG TCA TAC TGG GGA

136  CTT ACA AGG TCA TCT CCA ACG TGC CCT GCA CCT CCA CAA CCA ACT GCC TCG
     GAA TGT TCC AGT AGA GGT TGC ACG GGA CGT GTT GGT TGA CGG AGC

181  CTC CTC TCG CTA AGG TCA TCC ATG ACA ACT TCG AGA TCA TTG AAG
     GAG GAG AGC GAT TCC AGT AGG TAC TGT TGA AGC TCT AGT AAC TTC

226  GTC TGA TGA CCA CTG TAC ACG ATG TGC CCA CTG CCA CCC AGA AGA CAG
     CAG ACT ACT GGT GAC ATG TGC TAC CCG GGT GAC GGG TCT TCT GTC

271  TGG ATG GAC CCT CTG GTA AAC TGT GGC GTG ATG GCC GTG GTG CTC
     ACC TAC CTG GGA GAC CAT TTG ACA CCG CAC TAC CGG CAC CAC GAG

316  AGC AGA ATA TCA TTC CCG CGG AAT TCC CCA GCC GCA GCT TAA
     TCG TCT TAT AGT AGT AAG GGC GCC TTA AGG CGT CGA TCG ATT
```

Fig.2 i.

```
361  CCT GCA GCA GAC ACA ACC CCT ACC TTC CAT GCC GTT ACC AAT GCC
     GGA CGT CGT CTG TGT TGG GGA AAG GTA CGG CAA TGG TTA CGG

406  ACC GAC AAC ACC CAA ATC AGA AAA CGA GTC AAT GTC ATC AGG TCG
     TGG CTG TTG TGG GTT TAG TCT TTT GCT CAG TTA CAG TAG TCC AGC

451  TGA GGA ACT GTC TCC AGC TTC GAG TGT AAA CGG CTG CAG CAC AGA
     ACT CCT TGA CAG AGG TCG AAG CTC ACA TTT GCC GAC GTC GTG TCT

496  TGG CGA GGC GAG GCG GCA GAA GAA AGG CCC AGC GCC GAG GCA GCA
     ACC GCT CCG CTC CGC CGT CTT CTT TCC GGG TCG CTC CGT CGT

541  AGA AGA GCT ATG TCT TGT CTG CGG CGA CAG AGC CTC CGG ATA TCA
     TCT TCT CGA TAC AGA ACA GAC GCC GCT GTC GAG GCC TAT AGT

586  CTA CAA CGC GCT CAC ATG TGA AGG GTG TAA AGG TTT CTT CAG GCG
     GAT GTT GCG CGA GTG TAC ACT TCC CAC ATT AAA GAA GTC CGC

631  GAG TGT AAC CAA AAA TGC AGT CAT GTA CAT ATG CAA ATT CGG CCA TGC
     CTC ACA TTG GTT TTT ACG TCA CAT GTA TAC GTT TAA GCC GGT ACG

676  TTG CGA AAT GGA TAT CTA TAT GCG GAG AAA ATG TCA GTG TCG
     AAC GCT TTA CCT ATA GAT ATA CGC CTC TTT TAC AGT CCT CAC AGC

721  GTT GAA GAA ATG TCT TGC GGT GGG CAT GAG GCC CGA GTG CGT GGT
     CAA CTT CTT TAC AGA ACG CCA CCC GTA CTC GCT CGG CAC GCA CCA

766  GCC GGA GAA CCA GTG TGC AAT GAA ACG GAA AGA AAA GGC GCA
     CGG CCT CTT GGT CAC ACG TTA CTT TGC CTT TCT TTT CCG CGT
```

Fig.2 ii.

```
 811 GAG GGA AAA AGA CAA ATT GCC CGT CAG TAC GAC GAC AGT AGA CGA
     CTC CCT TTT TCT GTT TAA CGG GCA GTC ATG CTG CTG TCA TCT GCT

856 TCA CAT GCC TCC CAT CAT GCA ATG TGA CCC TCC GCC CCC AGA GGC
     AGT GTA CGG AGG GTA GTA CGT TAC ACT GGG AGG CGG GGG TCT CCG

901 CGC TAG AAT TCT GGA ATG TGT GCA CGA GGT GGT GCC ACG ATT
     GCG ATC TTA AGA CCT TAC ACA CGT GCT CCA CGG TGC TAA

946 CCT GAA TGA GAA GCT AAT GGA ACA GAA CAG ATT GAA GAA CGT GCC
     GGA CTT ACT CGA TTA CCT TGT CTT GTC TAA CTT GCA CGG

991 CCC CCT CAC TGC CAA TCA GAA GTT GAT GTC AAG GCT CGT GTG
     GGG GGA GTG ACG GTT AGT CTT CAA CTA GCG TTC CGA GCA CAC

1036 GTA CCA GGA AGG CTA TGA ACA ACC TTC CGA AGA CCT GAA GAG
     CAT GGT CCT TCC GAT ACT TGT TGG AAG GCT TCT GGA CTT CTC

1081 GGT TAC ACA GTC CGA GAC GGA CGA AGA CTC GGA TAT GCC GTT
     CCA ATG TGT CAG GCT CTG CCT GCT TCT GAG ATA CGG CAA

1126 CCG TCA GAT TAC CGA TAC AGT CAC GCT GCA GCT CAT CGT
     GGC AGT CTA ATG GCT ATG TCA CGT CGA GTA GCA

1171 AGA ATT CGC TAA GGG CCT CGC CAA GAT CTC GCA GTC
     TCT TAA GCG ATT CCC GGA GCG GTT CTA GAG CGT CAG

1216 GGA CCA GAT CAC GTT ATT AAA GGC GTG CTC AAG TGA GGT GAT
     CCT GGT CTA GTG CAA TAA TTT CCG CAC GAG TTC ACT CCA CTA

1261 GCT CCG AGT GGC TCG TGA GTA CGC GGC CAC CGA CAG CGT ACT
     CGA GGC TCA CCG AGC CGC CAT ACT GCG CCG GTG GCT GCA TGA
```

Fig.2 iii.

```
1306  GTT CGC GAA CAA CCA GGC GTA CAC TCG CGA CAA CTA CCG CAA GGC
      CAA GCG CTT GTT GGT CAT GTG AGC GCT GTT GAT GGC GTT CCG

1351  AGG CAT GGC GTA CTC CAT CGA GGA CGA CCT GCT GCA CTT CTG GTG
      TCC GTA CCG CAT GAG GTA GCT CCT CGA CGA CGT GAA GAC CAC

1396  CAT GTA CTC CAT GAT GAT GGA TAA CGT GCA TTA TGC GCT TAC
      GTA CAT GAG GTA CTA CTA CCT ATT GCA CGT AAT ACG CGA ATG

1441  AGC CAT TGT CAT CTT CTC AGA GCC CGG GCT CCT GCT GCA ACC CCT
      TCG GTA ACA GTA GAA GAG TCT CGG GCC CGA CGA CGT TGG GGA

1486  GTT GGT GGA CAT CCA GAG ATA TTA CCA GCC CGG CGT ACG GGT
      CAA CCA CCT GTA GGT CTC TAT AAT GGT CGG GCC GCA TGC CCA

1531  GTA CAT CCT GAA CTC CAG CGC GAA CAG CGC CGT CAT
      CAT GTA GGA CTT GAG GTC GCG CTT GTC GCG GCA GTA

1576  CTT CGG CGA GAT GAT CCT GGG CAT ACT GAC CCG CAC GCT GGG
      GAA GCC GCT CTA CTA GGA CCC GTA TGA CTG GGC GTG CGA CCC

1621  CAT GCA GAA CTC CAA CTC CAT GTG GGA GAT CTG GAA CAG
      GTA CGT CTT GAG GTT GAG GTA CAC CCT CTA GAC CTT GTC

1666  GAA GCT GCC GCC GTT CCT CGA GGA CCT CGT GGA CGT
      CTT CGA CGG CGG CAA GGA GCT CCT GGA GAC CCT GCA

1711  GGC GAC GAC GGC GGT GGC GAC GCC GGC GCC TCT
      CCG CTG CTG CCG CCA CCG CTG CGG CCG CGG AGA
```

Fig.2 iv.

```
1756 AGC CCC CGC CCC GCC CGC CCG GCC CGC CAC CGT CTA GCG CGC
     TCG GGG GCG GGG CGG GCG GGC CGG GCG GTG GCA GAT CGC GCG

1801 CTC AGG AGA GAA CGC TCA TAG ACT GGC TAG TTT TAG TGA AGT GCA
     GAG TCC TCT CTT GCG AGT ATC TGA CCG ATC AAA ATC ACT TCA CGT

1846 CGG ACA CTG ACG TCG ACG TGA TCA ACC TAT TTA TAA GGA CTG CGA
     GCC TGT GAC TGC AGC TGC ACT AGT TGG ATA AAT ATT CCT GAC GCT

1891 ATT TTA CCA CTT AAG AGG GCA CAC CCG TAC CCG ATT TCG TAC GG
     TAA AAT GGT GAA TTC TCC CGT GTG GGC ATG GGC TAA AGC ATG CC
```

Total number of bases is: 1934.

Fig.3.

The sequence shown below is that of pSK16.1

Sequence ID3

```
            3           9          15          21          27          33          39          45
            —           —           —           —           —           —           —           —
  1  CGC TGG TAT AAC AAC GGA CCA TTC CAG ACG CTG CGA ATG CTC GAG
     GCG ACC ATA TTG TTG CCT GGT AAG GTC TGC GAC GCT TAC GAG CTC

46  GAG AGC TCG TCT GAG GTG ACG TCG TCT TCA GCA CTG GGC CTG CCG
     CTC TCG AGC AGA CTC CAC TGC AGC AGA AGT CGT GAC CCG GAC GGC

91  CCG GCT ATG GTG ATG TCC CCG GAA TCG CTC GCG TCG CCC GAG ATC
     GGC CGA TAC CAC TAC AGG GGC CTT AGC GAG CGC AGC GGG CTC TAG

136  GGC GGC CTG GAG CTG TGG GGC TAC GAC GAT GGC ATC ACT TAC AGC
     CCG CCG GAC CTC GAC ACC CCG ATG CTA CCG CTA TGA ATG TCG

181  ATG GCA CAG TCG CTG GGC ACC TGC ACC ATG GAG CAG CAG CCC
     TAC CGT GTC AGC GAC CCG TGG ACG TAC CTC GTC GTC GGG
```

Fig. 3 i.

```
226  CAG CCG CAG CAG CAG CCG CAG ACA CAA CCC CTA CCT TCC ATG
     GTC GGC GTC GTC GTC GGC GTC TGT GTT GGG GAT GGA AGG TAC

271  CCG TTA CCA ATG CCA ACA CCG ACA CCC AAA TCA GAA AAC GAG TCA
     GGC AAT GGT TAC GGT TGT GGC TGT GGG TTT AGT CTT CTC AGT

316  ATG TCA TCA GGT CGT GAG GAA CTG TCT CCA GCT TCG AGT GTA AAC
     TAC AGT AGT CCA GCA CTC GAC AGA GGT CGA AGC TCA CAT TTG

361  GGC TGC AGC ACA GAT GGC GAG AGG CGG CAG AAG AAA GGC CCA
     CCG ACG TCG TGT CTA CCG CTC CGC GCC GTC TTC TTT CCG GGT

406  GCG CCG AGG CAG CAA GAA GAG CTA TGT CTT GTC TGC GGC GAC AGA
     CGC GGC TCC GTT CTT CTC GAT ACA GAA CAG ACG CTG TCT

451  GCC TCC GGA TAT CAC TAC AAC GCG CTC ACA TGT GAA GGG TGT AAA
     CGG AGG CCT ATA GTG ATG TTG CGC GAG TGT ACA CTT CCC ACA TTT

496  GGT TTC TTC AGG CGG AGT GTA ACC AAA AAT GCA GTG TAC ATA TGC
```

Fig.3 ii.

```
    CCA AAG AAG TCC GCC TCA CAT TGG TTT TTA CGT CAC ATG TAT ACG
541 AAA TTC GGC CAT GCT TGC GAA ATG GAT ATC TAT ATG CGG AGA AAA
    TTT AAG CCG GTA CGA ACG CTT TAC CTA TAG ATA TAC GCC TCT TTT
586 TGT CAG GAG TGT CGG TTG AAG TGT CTT GCG GTG GGC ATG AGG
    ACA GTC CTC ACA GCC AAC TTC ACA GAA CGC CAC CCG TAC TCC
631 CCC GAG TGC GTG GTG CAG CCG GAG AAC CAG TGT GCA ATG AAA CGG AAA
    GGG CTC ACG CAC CAC GGC CTC TTG GTC ACA CGT TAC TTT GCC TTT
676 GAG AAA AAG GCG CAG AGG GAA AAA GAC ATG CCT CCC GTC AGT ACG
    CTC TTT TTC CGC GTC CTT TTT CTG TAC GGA GGG CAG TCA TGC
721 ACG ACA GTA GAC GAT CAC ATC CCC ATC ATG CAA TGT GAC CCT
    TGC TGT CAT CTG CTA GTG TAG GGG TAG TAC GTT ACA CTG GGA
766 CCG CCC CCA GAG GCC GCT AGA ATT CTG GAA TGT GTG CAG CAC GAG
    GGC GGG GGT CTC CGG TCT TAA GAC CTT ACA CAC GTC GTG CTC
811 GTG GTG CCA CGA TTC CTG AAT GAG AAG CTA ATG GAA CAG AAC AGA
    CAC CAC GGT GCT AAG GAC TTA CTC TTC GAT TAC CTT GTC TTG TCT
856 TTG AAG GTG CCC CCC CTC ACT GCC AAT CAG AAG TCG TTG ATC
    AAC TTC CAC GGG GAG TGA CGG TTA GTC TTC AGC AAC TAG
901 GCA AGG CTC GTG TGG TAC CAG GAA TAT GAA CAA CCT TCC GAG
    CGT TCC GAG CAC ACC ATG GTC CTT CTA GTT GGA AGG CTC
946 GAA GAC CTG AAG AGG GTT ACA CAG TCG GAC GAC GAC GAA GAC
    CTT CTG GAC TTC TCC CAA TGT GTC AGC CTG CTG CTG CTT CTG
```

Fig.3 iii.

```
 991 TCG GAT ATG CCG TTC CGT CAG ATT ACC GAG ATG ACG ATT CTC ACA
     AGC CTA TAC GGC AAG GCA GTC TAA TGG CTC TAC TGC TAA GAG TGT

1036 GTG CAG CTC ATC GTA GAA TTC GCT AAG GGC CTC CCG GGC TTC GCC
     CAC GTC GAG TAG CAT CTT CGA CGA TTC CCG GAG GGC CCG AAG CGG

1081 AAG ATC TCG CAG TCG GAC CAG ATC ACG TTA TTA AAG GCG TGC TCA
     TTC TAG AGC GTC AGC CTG GTC TAG TGC AAT TTC CGC ACG AGT

1126 AGT GAG GTG ATG ATG CTC CGA GTG GCT CGG CGG TAT GAC CGG GCC
     TCA CTC CAC TAC TAC GAG GCT CAC CGA GCC ATA CTG CGC CGG

1171 ACC GAC AGC GTA CTG TTC CAT GAC AAC CAG TAC ACT CGC GAC
     TGG CTG TCG CAT GAC AAG CGC TTG GTC ATG TGA GCG CTG

1216 AAC TAC CGC AAG GCA GGC ATG GCG TAC GTC GAG GAC CTG CTG
     TTG ATG GCG TTC CGT CCG TAC CGC CTC CTG GAC GAC

1261 CAC TTC TGT CGG TGC ATG ATG TCC ATG ATG GAT AAC GTG CAT
     GTG AAG ACA GCC TAC ACG TAC TAC AGG TAC TAC CTA TTG CAC GTA

1306 TAT GCG CTT ACA GCC ATT GTC ATC TTC TCA GAC CGG CCC GGG
     ATA CGC GAA TGT CGG TAA CAG TAG AAG AGT CTG GCC GGG CCC

1351 CTT GAG CAA CCC CTG TTG GTG GAG GAC ATC CAG AGA TAT TAC CTG
     GAA CTC GTT GGG GAC AAC CAC CTC CTG TAG GTC TCT ATA ATG GAC

1396 AAC ACG CTA CGG GTG TAC ATC CTG AAC AGC GCG GCG TCG CCC
     TTG TGC GAT GCC CAC ATG GAC TTG TCG AGC CGC AGC GGG

1441 CGC GGC GCC ATC TTC GGC GAG ATC CTG ACG GAG
     GCG ATA CTG ACG GAG
```

Fig.3 iv.

```
        GCG CCG CGG CAG TAG AAG CCG CTC TAG GAC CCG TAT GAC TGC CTC
1486 ATC CGC ACG CTG GGC ATG CAG AAC TCC AAC ATG TGC ATC TCC CTC
     TAG GCG TGC GAC CCG TAC GTC TTG AGG TTG TAC ACG TAG AGG GAG

1531 AAG CTG AAG AAC AGG AAG CTG CCG CCG TTC CTC GAG GAG ATC TGG
     TTC GAC TTC TTG TCC TTC GAC GGC GGC AAG GAG CTC TAG ACC

1576 GAC GTG GCG GAC GTG CAC GCG ACG CCG GTG GCG GCG GCG GCG GAG
     CTG CAC CGC CTG CAC GTG CGC TGC GGC CAC CGC CGC CGC CGC CTC

1621 GCG CCG GCG CCT CTA GCC CCC CCC GCC CGG CCC CCC CCC GCC
     CGC GGC CGC GGA GAT CGG GGG GGG CGG GCC GGG GGG GGG CGG

1666 ACC GTC TAG CGC GCC TCA GGA GAG AAC GCT CAT AGA CTG GCT AGT
     TGG CAG ATC GCG CGG AGT CCT CTC TTG CGA TCT GAC CGA TCA

1711 TTT AGT GAA GTG CAC GGA CAC TGA CGT CGA GAT CAA CCT ATT
     AAA TCA CTT CAC GTG CCT GTG ACT GCA GCT CTA GTT GGA TAA

1756 TAT AAG GAC TGC GAA TTT AAA TTA TAC CAC AGA GGG CAC ACC CGT ACC
     ATA TTC CTG ACG CTT AAA AAT ATG GTG TCT CCC GTG TGG GCA TGG

1801 CGA TTT CGT ACG TAT ATG TCG GTG ACC GAC GAT GCA GAG CGT GTG
     GCT AAA GCA TGC ATA TAC AGC CAC TGG CTG CTA CGT CTC GCA CAC

1846 TAA TGT GAA TAT ATG TGT TGA ACG ATT TGG AGA ATA TAT ATT
     ATT ACA CTT ATA TAC ACA ACT TGC TAA ACC TCT TAT ATA TAA

1891 GGT GTT GCT GTT CGG GCC CGC CCG TCG CCG CCG GTC CGG CGT GAT
     CCA CAA CGA CAA GCC CGG GCG AGC AGC GGC CAG GCC GCA CTA
```

Fig. 3 v.

```
1936 CGC GGC GCC CGC GGC TTC AGT TTT ATT TCG TTT ACG ACT GAG TTG
     GCG CCG CGG GCG CCG AAG TCA AAA TAA AGC AAA TGC TGA CTC AAC

1981 GTC ACT CGG ATA CGA CTG TAT GAT AAG ACT TCG TTC GAT AAG TAC
     CAG TGA GCC TAT GCT GAC ATA CTA TTC TGA AGC AAG CTA TTC ATG

2026 ACC TAC TAA ATT ACA CAT ACG TAC GTA GCT TAC GAG AGT TAT TAG
     TGG ATG ATT TAA TGT GTA TGC ATG CAT CGA ATG CTC TCA ATA ATC

2071 AGA CAA AGA ATA TAA GAA GAT GTT TCT ATT GGG TGA AAA GTT
     TCT GTT TCT TAT ATT CTT CTA CAA AGA TAA CCC ACT TTT CAA

2116 GAT AGT TAT GTT TAT TTA CCA AAA ATA ACA ATA CGT TGA TTA
     CTA TCA ATA CAA ATA AAT GGT TTT TGT TAT GCA ACT AAT

2161 ACC TTT CGA GTA TAA TAT GAG TCC GCT GTC CAC GTC
     TGG AAA GCT CAT ATT ATA CTC AGG CGA CAG GTG CAG

2206 GCC GTC ACA TGT TTG TTT CTG ATG CAC ACG TGA GGN GCG TTA TCG
     CGG CAG TGT ACA AAC AAA GAC TAC GTG TGC ACT CCN CGC AAT AGC

2251 TGT TTC ATG GTT CCA TCG TCC TGC CGC GAC CCT CGA CTA AAT
     ACA AAG TAC CAA AGG AGC AGG ACG GCG GCG GGA GCT GAT TTA

2296 GAG TAA TTT AAT TTA CTG TGA TTA CAT TTT AAT GTG TTG ATT
     CTC ATT AAA TAA GAC ACT AAT GTA AAA TTA CAC AAC TAA

2341 ATC TAC CAT AGG GTG ATA TAA GTT TGT CTT ATT ACA ATA CAA AGT
     TAG ATG GTA TCC CAC TAT ATT CAA ACA GAA TAA TGT TAT GTT TCA

2386 GTG TGT CGT CGA TAG CTT CCA CAC GAG CAA GCC TTT TGT TTA AGT
```

Fig.3 vi.

```
         CAC ACA GCA GCT ATC GAA GGT GTG CTC GTT CGG AAA ACA AAT TCA
2431 GAT TTA CTG ACA TGG ACA CTC GAC CCG GAA CTT C
     CTA AAT GAC TGT ACC TGT GAG CTG GGC CTT GAA G
```

Total number of bases is: 2464.

Fig.4.

Sequence ID 4

```
         10         20         30         40         50         60
         |          |          |          |          |          |
ACTCGGCGTGCTCTCTCACCTGTTGCTCGGATTGTGTTGTACTAGAAAAAGTTGTCGCC 70         80         90        100        110        120
         |          |          |          |          |          |
GCTCGAACGAGACTTCCGAGTCCTATTGGATTGCACGAAAGTCGAGACAGTGGATAGCGA 130        140        150        160        170        180
         |          |          |          |          |          |
TTCGGTTTCGTTTGAACGTTGCGTAGACGAGTGGTGCATGTCCATGAGTCGCGTTTAGAT
```

Fig. 4 i.

```
         190       200       210       220       230       240
          |         |         |         |         |         |
AGTTTAGTGCGAGGAAAAAGTGAAAGTGAAAGCCTTCCTCGGAGGATGTCCCTCGGCGCTC
                                              M  S  L  G  A 250       260       270       280       290       300
          |         |         |         |         |         |
GTGGATACCGGAGGTGTGACACGCTCGCCGACATGAGACGCCGCTGGTATAACAACGGAC
 R  G  Y  R  R  C  D  T  L  A  D  M  R  R  R  W  Y  N  N  G 310       320       330       340       350       360
          |         |         |         |         |         |
CATTCCAGACGCTGCGAATGCTCGAGGAGAGCTCGTCTGAGGTGACGTCGTCTTCAGCAC
  P  F  Q  T  L  R  M  L  E  E  S  S  E  V  T  S  S  S  A 370       380       390       400       410       420
          |         |         |         |         |         |
TGGGCCTGCCGCCGGCTATGGTGTCCCCGGAATGTCGCTCGCCTCGCCCCGAGATCGGCG
 L  G  L  P  P  A  M  V  S  P  E  S  L  A  S  P  E  I  G
```

Fig. 4 ii.

```
         430         440         450         460         470         480
          |           |           |           |           |           |
GCCTGAGAGTCGTGTGGGCTACGACGATGGCATCACTTACAGCATGGCACAGTCGCTGGGCA
 G   L   E   L   W   G   Y   D   D   G   I   T   Y   S   M   A   Q   S   L   G 490         500         510         520         530         540
          |           |           |           |           |           |
CCTGCACCATGGAGCAGCAGCCCCAGCAGCCGCAGCAGCAGCCGCAGCAGCAGACACAACCCC
 T   C   T   M   E   Q   Q   P   Q   Q   P   Q   Q   Q   P   Q   Q   T   Q   P 550         560         570         580         590         600
          |           |           |           |           |           |
TACCTTCCATGCCGTTACCAATGCCACCGACAACACCCAAATCAGAAAAACGAGTCAATGT
 L   P   S   M   P   L   P   M   P   P   T   T   P   K   S   E   N   E   S   M 610         620         630         640         650         660
          |           |           |           |           |           |
CATCAGTCGTGAGGAACTGTCTCCAGCTTCGAGTGTAAACGGCTGCAGCACAGATGGCG
 S   S   G   R   E   E   L   S   P   A   S   S   V   N   G   C   S   T   D   G 670         680         690         700         710         720
          |           |           |           |           |           |
AGGCGAGGCGGCAGAAGAAAGGCCCAGCCGCGAGGCAGCAAGAAGAGCTATGTCTGTCT
 E   A   R   R   Q   K   K   G   P   A   P   R   Q   Q   E   E   L   C   L   V
```

Fig.4 iii.

```
 730                                                              780
  |         740         750         760         770          |
  |          |           |           |           |           |
GCGGGCGACAGAGCCTCCGGATATCACTACAACGCGCTCACATGTGAAGGGTGTAAAGGTT
 C  G  D  R  A  S  G  Y  H  Y  N  A  L  T  C  E  G  C  K  G 790                                                              840
  |         800         810         820         830          |
  |          |           |           |           |           |
TCTTCAGGCGGAGTGTAACCAAAAATGCAGTGTACATATGCAAATTCGGCCATGCTTGCG
 F  F  R  R  S  V  T  K  N  A  V  Y  I  C  K  F  G  H  A  C 850                                                              900
  |         860         870         880         890          |
  |          |           |           |           |           |
AAATGGATATATATGCGGAGAAAATGTCAGGAGTGTCGGTTGAAGAAATGTCTTGCGG
 E  M  D  I  Y  M  R  R  K  C  Q  E  C  R  L  K  K  C  L  A 910                                                              960
  |         920         930         940         950          |
  |          |           |           |           |           |
TGGGCATGAGGCCCGAGTGCGTGGTGCCGGAGAACCAGTGTGCAATGAAACGGAAAGAGA
 V  G  M  R  P  E  C  V  V  P  E  N  Q  C  A  M  K  R  K  E 970                                                             1020
  |         980         990        1000        1010          |
  |          |           |           |           |           |
AAAAGGCGCAGAGGGAAAAGACAAATTGCCCGTCAGTACGACGACAGTAGACGATCACA
 K  K  A  Q  R  E  K  D  K  L  P  V  S  T  T  T  V  D  D  H
```

Fig. 4 iv.

```
        1030      1040      1050      1060      1070      1080
         |         |         |         |         |         |
TGCCTCCCATCATGCAATGTGACCCTCCGCCCCCAGAGGCCGCTAGAATTCTGGAATGTG
 C  L  P  S  C  N  V  T  L  R  P  Q  R  P  L  E  F  W  N  V
 M  P  P  I  M  Q  C  D  P  P  P  P  E  A  A  R  I  L  E  C 1090      1100      1110      1120      1130      1140
         |         |         |         |         |         |
TGCAGCACGAGGTGTGCCACGATTCCTGAATGAGAAGCTAATGGAACAGAACAGATTGA
 V  Q  H  E  V  V  P  R  F  L  N  E  K  L  M  E  Q  N  R  L 1150      1160      1170      1180      1190      1200
         |         |         |         |         |         |
AGAACGTGCCCCCTCACTGCCAATCAGAAGTCGTTGATCGCAAGGCTCGTGTGGTACC
 K  N  V  P  P  L  T  A  N  Q  K  S  L  I  A  R  L  V  W  Y 1210      1220      1230      1240      1250      1260
         |         |         |         |         |         |
AGGAAGGCTATGAACAACCTTCCGAGGAAGACCTGAAAGAGGGTTACACAGTCGGACGAGG
 Q  E  G  Y  E  Q  P  S  E  E  D  L  K  R  V  T  Q  S  D  E
```

Fig. 4 v.

```
          1270       1280       1290       1300       1310       1320
           |          |          |          |          |          |
      ACGACGAAGACTCGGATATGCCGTTCCGTCAGATTACCGAGATGACGATTCTCACAGTGC
        D  D  E  D  S  D  M  P  F  R  Q  I  T  E  M  T  I  L  T  V 1330       1340       1350       1360       1370       1380
           |          |          |          |          |          |
      AGCTCATCGTAGAATTCGCTAAGGGCCTTCCCGGGCTTCGCCAAGATCTCGCAGTCGGACC
        Q  L  I  V  E  F  A  K  G  L  P  G  F  A  K  I  S  Q  S  D 1390       1400       1410       1420       1430       1440
           |          |          |          |          |          |
      AGATCACGTTATTAAAGGCGTGCTCAAGTGAGGTGATGATGCTCCGAGTGGCTCGGCGGT
        Q  I  T  L  L  K  A  C  S  S  E  V  M  M  L  R  V  A  R  R 1450       1460       1470       1480       1490       1500
           |          |          |          |          |          |
      ATGACGCGGCCACCGACAGCGTACTGTTCGCGAACAACCAGGCGTACACTCGCGACAACT
        Y  D  A  A  T  D  S  V  L  F  A  N  N  Q  A  Y  T  R  D  N
```

Fig.4 vi.

```
         1510      1520      1530      1540      1550      1560
          |         |         |         |         |         |
ACCGCAAGGCAGGCATGGCCGTACGTCATCGAGGACCTGCTGCACTTCTGTCGGTGCATGT
 Y  R  K  A  G  M  A  Y  V  I  E  D  L  L  H  F  C  R  C  M 1570      1580      1590      1600      1610      1620
          |         |         |         |         |         |
ACTCCATGATGATGGATAACGTGCATTATGCGCTGCTTACAGCCATTGTCATCTTCTCAG
 Y  S  M  M  M  D  N  V  H  Y  A  L  L  T  A  I  V  I  F  S 1630      1640      1650      1660      1670      1680
          |         |         |         |         |         |
ACCGGGCCCGGGCTTGAGCAACCCCTGTTGGTGGAGGAGATCCAGAGATATTACCTGAACA
 D  R  P  G  L  E  Q  P  L  L  V  E  E  I  Q  R  Y  Y  L  N 1690      1700      1710      1720      1730      1740
          |         |         |         |         |         |
CGCTACGGGTGTACATCCTGAACCAGAACAGCGCGTCGCCCCGCGGCGTCATCTTCG
 T  L  R  V  Y  I  L  N  Q  N  S  A  S  P  R  G  A  V  I  F
```

Fig. 4 vii.

```
        1750       1760       1770       1780       1790       1800
         |          |          |          |          |          |
GCGAGATCCTGGGCATACTGACGGAGATCCGCACGCTGGGCATGCAGAACTCCAACATGT
 G  E  I  L  G  I  L  T  E  I  R  T  L  G  M  Q  N  S  N  M 1810       1820       1830       1840       1850       1860
         |          |          |          |          |          |
GCATCTCCCTCAAGCTGAAGAACAGGAAGCTGCCGTTCCTCGAGGAGATCTGGGACG
 C  I  S  L  K  L  K  N  R  K  L  P  P  F  L  E  E  I  W  D 1870       1880       1890       1900       1910       1920
         |          |          |          |          |          |
TGGCGGACGTGGCCGACGGCGACGCCGGTGGCGGAGGCGCCGGCCTCTAGCCC
 V  A  D  V  A  T  T  A  T  P  V  A  A  E  A  P  A  P  L  A 1930       1940       1950       1960       1970       1980
         |          |          |          |          |          |
CCGCCCCCGCCCCGGCCCGCCACCGTCGCCTCAGGAGAGAACGCTCATA
 P  A  P  P  A  R  P  P  P  A  T  V  -

1990       2000       2010       2020       2030       2040
         |          |          |          |          |          |
GACTGGCTAGTTTTAGTGAAGTGCACGGACACTGACGTGATCAACCTATTTATA
```

Fig.4 viii.

```
2050        2060        2070        2080        2090        2100
  |           |           |           |           |           |
AGGACTGCGAATTTACCACTTAAGAGGGCACACCCGTACCCGATTTCGTACGTATTCGG 2110        2120        2130        2140        2150        2160
  |           |           |           |           |           |
TGACCGACGACGATGCAGAGCGTGTGTAATGTGAATATATGTGTTGTTGAACGATTTGA 2170        2180        2190        2200        2210        2220
  |           |           |           |           |           |
GAATATATATTGGTGTTGCTGTTCGGGCCCCGCACGCCGTCGGGCGGGCGGATCGCG 2230        2240        2250        2260        2270        2280
  |           |           |           |           |           |
GCGCCCCGGGCTTCAGTTTTATTCGTTTACGACTGAGTTGGTCACTCGGATACGACTGT 2290        2300        2310        2320        2330        2340
  |           |           |           |           |           |
ATGATAAGACTTCGTTCGATAAGTACACCTACTAAATTACACATACGTACGTAGCTTACG 2350        2360        2370        2380        2390        2400
  |           |           |           |           |           |
AGAGTTATTAGAGACAAAGAATATAAGAAGAGATGTTTCTATTGGGTGAAAAGTTGATA
```

Fig. 4 ix.

```
2410       2420       2430       2440       2450       2460
   |          |          |          |          |          |
GTTATGTTTATTACCAAAATTAACAATAATACGTTGATTAACCTTTCGAGTATAATATT 2470       2480       2490       2500       2510       2520
   |          |          |          |          |          |
GTGATGAGTCGTCCGCTGTCCACGTCGGCCGTCACATGTTTGTTTCTGATGCACACGTGAG 2530       2540       2550       2560       2570       2580
   |          |          |          |          |          |
GNGCCGTTATCGTGTTTCATGGTTCCATCGTCGTCCTGTGCCGCGACCCTCGACTAAATGAGT 2590       2600       2610       2620       2630       2640
   |          |          |          |          |          |
AATTAATTTATTGCTGTGTGATTACATTTTAATGTGTTGATTATCTACCATAGGGTGATAT 2650       2660       2670       2680       2690       2700
   |          |          |          |          |          |
AAGTGTCTCTTATTACAATACAAAGTGTGTCGTCGATAGCTTCCACACGAGCAAGCCT 2710       2720       2730       2740
   |          |          |          |
TTTGTTTAAGTGATTACTGACATGGACACTCGACCCGGAACTTC
```

Fig.5.

Sequence I.D. 5

```
                  10
BmECR    MRVENVDNVS
MsECR    ----------
HvECR    M---------
CtECR    ----------
AaECR    ----------
DmECR    ----------
```

```
                                                            60
BmECR    FALNGRADEWCMSVETRLDSLVREKSEVKAYVGGCPSVITDAGAYDALFD
MsECR    --------------------------------------------------
HvECR    -SLGARGYRRC---------------------------------------         16
CtECR    --------------------------------------------------
AaECR    --------------------------------------------------
DmECR    --------------------------------------------------
```

```
                                                                 107
BmECR    M-RRRWSNNGGFP-LRMLEESSSEVTSSSA-LGLPPAMVMSPESLASPEY        107
MsECR    M-RRRWSNNGCFP-LRMFEESSSEVTSSSA-FGMPAAMVMSPESLASPEY         47
HvECR    M-RRRWYNNGGFQTLRMLEESSSEVTSSSA-LGLPPAMVMSPESLASPEI         64
CtECR    M-K----------------TENLIVTT-VKVEPLNYASQSF                  23
AaECR    MMKRRWSNNGGFTALRMLDDSSSEVTSSSAAL---GMTMSPNSLGSPNY          46
DmECR    M-KRRWSNNGGF--MRLPEESSSEVTSSSNGLVLPSGVNMSPSSLDSHDY         47
              *                    *    .  .     ..  *  . ..
```

Fig. 5 i.

```
BmECR  GALELW-------SY-----------------------------------------------                              114
MsECR  GGLELW-------SY-----------------------------------------------                               55
HvECR  GGLELW-------GY-----------------------------------------------                               72
CtECR  GDNNI--------YGGAT--------------------------------------------                               33
AaECR  DELELW-SSYEDNAYNGHSV--LSNGNNN------LGGCGA---------------------                               78
DmECR  CDNDKWLCGNESGSFGGSNGHGLSQQQQSVITLAMHGCSSTLPAQTTIIP             97

BmECR  ------------------------------------------------------DDGITY  121
MsECR  ------------------------------------------------------DETMTN   61
HvECR  ------------------------------------------------------DDGIT-   77
CtECR  ------------------------------------------KKQRLESDETMNH        46
AaECR  ----------------------------------ANNLLMNGIVGNNNL-----NGMMN    98
DmECR  INGNANGNGGSTNGQYVPGATNLGALANGMLNGGFNGMQQQIQNGHGLIN            147

BmECR  NTAQSLLGACNMQQQQLQP----------------------QQPHPAPPTLPTMP-----  154
MsECR  YPAQSLLGACNAPQQQQQQ----------------------QQQQPSAQPLPSMP-----   94
HvECR  YSMAQSLGTCTMEQQQPQP----------------------QQQPQQTQPLPSMP-----  114
CtECR  NQTMNLESSNMNHNTIS-------GFSSPDVNYEAYSPNSKL-------DDGN          86
AaECR  MASQAVQANANSIQHIVGN-------------LINGVNPNQTLIPPLPS-----        134
DmECR  STTPSTPTTPLHLQQNLGGAGGGIGGMGILHHANGTPNGLIGVVGGGGG             197

BmECR  ------LPMPPTTPKSENESMSSGREELSPASSINGCSADA--D                  190
MsECR  ------LPMPPTTPKSENESMSSGREELSPASSINGCSTDG--E                  130
HvECR  ------LPMPPTTPKSENESMSSGREELSPASSVNGCSTDG--E                  146
CtECR  ------------------------------------LDG------K                98
AaECR  IIQNTLMNTPRSESVNSISSGREDLSPSSSLNGYT--DGSD                    173
DmECR  VGLGVGGGVGGLGMQHTPRSDSVNSISSGRDDLSPSSSLNGYSANESCD             247
```

Fig. 5 ii.

```
BmECR   ARRQKKGPAPRQQEELCLVCGDRASGYHYNALTCEGCKGFFRRSVTKNAV       240
MsECR   PRRQKKGPAPRQQEELCLVCGDRASGYHYNALTCEGCKGFFRRSVTKNAV       180
HvECR   ARRQKKGPAPRQQEELCLVCGDRASGYHYNALTCEGCKGFFRRSVTKNAV       196
CtECR   KSSSKKGPVPRQQEELCLVCGDRASGYHYNALTCEGCKGFFRRSVTKNAV       148
AaECR   AKKQKKGPTPRQQEELCLVCGDRASGYHYNALTCEGCKGFFRRSVTKNAV       223
DmECR   AKKSKKGPAPRVQEELCLVCGDRASGYHYNALTCEGCKGFFRRSVTKSAV       297
        .****.** ****************************************

BmECR   YICKFGHACEMDMYMRRKCQECRLKKCLAVGMRPECVIQEPS-KNKDRQR       289
MsECR   YICKFGHACEMDMYMRRKCQECRLKKCLAVGMRPECVVPESTCKNKRREK       230
HvECR   YICKFGHACEMDIYMRRKCQECRLKKCLAVGMRPECVVPENQCAMKRKEK       246
CtECR   YCCKFGHECEMDMYMRRKCQECRLKKCLAVGMRPECVVPENQCAIKRKEK       198
AaECR   YCCKFGHACEMDMYMRRKCQECRLKKCLAVGMRPECVVPENQCAIKRKEK       273
DmECR   YCCKFGRACEMDMYMRRKCQECRLKKCLAVGMRPGCVVPGNQCAMKRREK       347
        * ****.. ****. ***********************  .*  ...

BmECR   QKKDKGILLPVSTTTV---------------------------EDHMPPIMQC     315
MsECR   EAQREKDKLPVSTTTV---------------------------DDHMPAIMQC     256
HvECR   KAQREKDKLPVSTTTV---------------------------DDHMPPIMQC     272
CtECR   KAQKEKDKVPGIVGSNTSSSSLLNQSLNNGSLKNLEISYREELLQQLMKC      248
AaECR   KAQKEKDKVQTNAT-------------VSTTNSTY-RS-----EILPILMKC     306
DmECR   KAQKEKDKMTTSPSSQHGGNGSLASGGGQDFVKK--------EILD-LMTC     389
                                                       *  .*

BmECR   DPPPPEAAARI-----HEVVPRYLSEKLMEQNRQKNIPPLSANQKSLIARL     360
MsECR   DPPPPEAAARI-----HEVVPRFLTEKLMEQNRLKNVTPLSANQKSLIARL     301
HvECR   DPPPPEAAARILECVQHEVVPRFLNEKLMEQNRLKNVPPLTANQKSLIARL     322
CtECR   DPPPHPMQQLL--------------PEKLLMENRAKGTPQLTANQVAVIYKL    286
AaECR   DPPPHQAIPLL--------------PEKLLQENRLRNIPLLTANQMAVIYKL    344
DmECR   EPPQHATIPLL--------------PDEILAKCQARNIPSLTYNQLAVITKL    427
        :**             .  ..  .
```

Fig.5 iii.

```
BmECR   VWYQEGYEQPSDEDLKRVTQTWQ-SDEEDEESDLPFRQITEMTILTVQLI        409
MsECR   VMYQEGYEQPSEEDLKRVTQTWQLEEEEEEETDMPFRQITEMTILTVQLI        351
HvECR   VWYQEGYEQPSEEDLKRVTQS----DEDDEDSDMPFRQITEMTILTVQLI        368
CtECR   IWYQDGYEQPSEEDLKRITTE--LEEEEDQEHEANFRYITEVTILTVQLI        334
AaECR   IWYQDGYEQPSEEDLKRIMIG--SPNEEEDQHDVHFRHITEITILTVQLI        392
DmECR   IWYQDGYEQPSEEDLRRIM-S--QPDENESQTDVSFRHITEITILTVQLI        474
        * * ****** ****  *     .          *  ** * ******

BmECR   VEFAKGLPGFSKISQSDQITLLKASSSEVMMLRVARRYDAASDSVLFANN        459
MsECR   VEFAKGLPGFSKISQSDQITLLKASSSEVMMLRVARRYDAATDSVLFANN        401
HvECR   VEFAKGLPGFAKISQSDQITLLKACSSEVMMLRVARRYDAATDSVLFANN        418
CtECR   VEFAKGLPAFIKIPQEDQITLLKACSSEVMMLRMARRYDHDSDSILFANN        384
AaECR   VEFAKGLPAFTKIPQEDQITLLKACSSEVMMLRMARRYDAATDSILFANN        442
DmECR   VEFAKGLPAFTKIPQEDQITLLKACSSEVMMLRMARRYDHSSDSIFFANN        524
        ********  ** *.******.*********.****** .. * ****

BmECR   KAYTRDNYRQGGMAYVIEDLLHFCRCMFAMGMDNVHFALLTAIVIFSDRP        509
MsECR   QAYTRDNYRKAGMSYVIEDLLHFCRCMYSMSMDNVHYALLTAIVIFSDRP        451
HvECR   QAYTRDNYRKAGMAYVIEDLLHFCRCMYSMMDNVHYALLTAIVIFSDRP         468
CtECR   TAYTKQTYQLAGMEETIDDLLHFCRQMYALSIDNVETALLTAIVIFSDRP        434
AaECR   RSYTRDSYRMAGMADTIEDLLHFCRQMFSLTVDNVEYALLTAIVIFSDRP        492
DmECR   RSYTRDSYKMAGMADNIEDLLHFCRQMFSMKVDNVEYALLTAIVIFSDRP        574
         ***  .   .*   .*.*******.*.    **   *************

BmECR   GLEQPSLVEEIQRYYLNTLRIYIINQNSASSRCAVIYGRILSVLTELRTL        559
MsECR   GLEQPLLVEEIQRYYLNQHSASPRCAVLFGKILGVLTELRTL                501
HvECR   GLEQPLLVEDIQRYYLNTLRVYILNQNSASPRGAVIFGEILGILTEIRTL        518
CtECR   GLEKAEMVDIIQSYYTETLRKVYIVRDHGGESRCSVQFAKLLGILTELRTM       484
AaECR   GLEQAELVEHIQSYYIDTLRIYILNRHAGDPKCSVIFAKLLSILTELRTL        542
DmECR   GLEKAQLVEAIQSYYIDTLRITILNRHCGDSMSLVFYAKLLSILTELRTL        624
        ***       *  *        *   .  .        .  *** **
```

Fig.5 iv.

```
BmECR   GTQNSNMCISLKLKNRKLPPFLEEIWDVAEVARR--------------------------   593
MsECR   GTQNSNMCISLKLKNRKLPPFLEEIWDVAEVSTT--------------------------   535
HvECR   GMQNSNMCISLKLKKRKLPPFLEEIWDVADVATT--------------------------   552
CtECR   GNLNSEMCFSLKLRNRKLPRFLEEVWDVGDVNQTTATTNTENIVRERIN              534
AaECR   GNQNSEMCFSLKLKNRKLPRFLEEIWDVQDIPPSMQAQMHSHGTQSSS--             590
DmECR   GNQNAEMCFSLKLKNRKLPKFLEEIWDVHAIPPSVQSHLQITQEEDERLE             674
        *   *  ** ****  .*** **  *****   .

BmECR   ------------------------------------------------------------   593
MsECR   ------------------------------------------------------------   535
HvECR   ------------------------------------------------------------   552
CtECR   RN----------------------------------------------------------   536
AaECR   ------SSSSSSSSSNGSSNGNSSSNSSQHGPHPHGQQ--LTPNQ                  632
DmECR   RAERMRASVGGAITAGIDCDSASTSAAAAAQHQPQPQPQPSSLTQND                724

BmECR   ---------------------HPTV-----------LPPTNPVVL---------------   606
MsECR   ---------QP--TPGVAAQVTPIVVDNPAAL----------------------------   556
HvECR   ---------ATPVAAEAPAPLAPAPPARPATV----------------------------   575
CtECR   ------------------------------------------------------------   536
AaECR   QQHQQ----------HSQLQQ--------------------V                     645
DmECR   SQHQTQPQLQPQLPPQLQGQLQPQLQPQLQTQLQPQIQPQPQLLPVSAPV             774

BmECR   ------------------------------------------------------------   606
MsECR   ------------------------------------------------------------   556
HvECR   ------------------------------------------------------------   575
CtECR   ------------------------------------------------------------   536
AaECR   HANGSGSGGGSNNNSSSG-----------------------------                663
DmECR   PASVTAPGSLSAVSTSSEYMGGSAAIGPITPATTSSITAAVTASSTTSAV             824
```

Fig.5 v.

```
BmECR    ------------------------------------------------------------    ------    606
MsECR    ------------------------------------------------------------    ------    556
HvECR    ------------------------------------------------------------    ------    575
CtECR    ------------------------------------------------------------    ------    536
AaECR    ----GVVPGLGMLDQV--------------------------------------------    ------    675
DmECR    PMGNGVGVGVGVGGNVSMYANAQTAMALMGVALHSHQQQLIGGVAVKSEH              STTA      878
```

Fig. 40.

Spodoptera exigua DNA sequence.

Sequence ID 6

SPODOPTERA EXIGUA HINGE AND LIGAND BINDING DOMAINS

```
      3         9        15        21        27        33        39        45
      |         |         |         |         |         |         |         |
  1 AGG CCG GAG TGC GTG GTG CCA GAA AAC CAG TGT GCA ATG AAA AGG
    TCC GGC CTC ACG CAC CAC GGT CTT TTG GTC ACA CGT TAC TTT TCC

46 AAA GAG AAA AAG GCA CAA AGG GAA AAA GAC AAG TTG CCA GTC AGT
    TTT CTC TTT TTC CGT GTT TCC CTT TTT CTG TTC AAC GGT CAG TCA

91 ACA ACG ACA GTG GAT GAT CAC ATG CCT CCC ATT ATG CAG TGT GAT
    TGT TGC TGT CAC CTA CTA GTG TAC GGA TAA GTG TAA GTC ACA CTA

136 CCA CCG CCT CCA GAG GCC GCA AGA ATT CAC GAG GTG GTG CCA CGA
    GGT GGC GGA GGT CTC CGG CGT TCT TAA GTG CTC CAC CAC GGT GCT

181 TTC CTG AAT GAA AAG CTA ATG GAC AGG ACA AGG CTC AAG AAT GTG
    AAG GAC TTA CTT TTC GAT TAC CTG TCC TGT TCC GAG TTC TTA CAC

226 CCC CCT CAC TGC CAA GTC CAA CCA GAA GTC CTT AAT AGC GAG GCT GGT CTG
    GGG GGA GTG ACG GTT CAG GTT GGT CTT CAG GAA TTA TCG CTC CGA CCA GAC

271 GTA CCA AGA AGG CTA TGA ACA GCC ATC AGA GGA GGA TCT AAA AAG
    CAT GGT TCT TCC GAT ACT TGT CGG TAG TCT CCT AGA TTT TTC
```

Fig. 40 i.

```
316 AGT CAC ACA GTC GGA TGA AGA AGA GTC GGA CAT GCC GTT
    TCA GTG TGT CAG CCT ACT TCT TCT CAG CCT GTA CGG CAA

361 CCG TCA GAT CAC CGA GAT CAC CCT GAC AGT GCA GCT CAT TGT
    GGC AGT CTA GTG GCT CTA GTG GGA CTG TCA CGT CGA GTA ACA

406 TGA ATT CGC TAA GGG CCT ACC AGC GTT CGC AAA GAT CTC ACA GTC
    ACT TAA GCG ATT CCC GGA TGG TCG CAA GCG TTT CTA GAG TGT CAG

451 GGA TCA GAT CAC ATT ATT AAA GGC CTG TTC GAG GGT GAT
    CCT AGT CTA GTG TAA TAA TTT CCG GAC AAG CTC CCA CTA

496 GTT GCG AGT AGC TCG GCG GTA CGA CGC GAC CTG AGA CAG CGT GTT
    CAA CGC TCA TCG AGC CGC CAT GCT GCG CTG TCT GTC GCA CAA

541 GTT CGC CAA CAA CCA GGC CTA CGT CAT CGA CCG CAA CTA CCG GGC
    CAA GCG GTT GTT GGT CCG GAT GCA GTA GCT GGC GTT GAT GGC CCG

586 AGG CAT GGC CTA CGT CAT GAT GAT GGA TAA CGT CCA CCT GCT CAC
    TCC GTA CCG GAT GCA GTA CTA CTA CCT ATT GCA GGT GAT ACG GTG

631 CAT GTA CTC CAT GAT CGT CAT TTT CTC AGA CGT CCA CTA TGC ACT CCT
    GTA CAT GAG GTA CTA GCA GTA AAA GAG TCT GCA GGT GAT ACG TGA GGA

676 TGC CAT GTA CTC GAT CGT CAT AGA GAG ATT GCA ACC CGG GCT TGA GCT AAC CCT
    ACG GTA CAT GAG CTA GCA GTA TCT CTC TAA CGT TGG GCC CGA ACT CGA TTG GGA

721 GTT GGT GGA GAT CCA GAG ATA TTA CCT GAA CAC GCT GGT GCG GGT
    CAA CCA CCT CTA GGT CTC TAT AAT GGA CTT GTG CGA CCA CGC CCA
```

Fig.40 ii.

```
766  GTA CAT CCT GAA CCA GAA CAG TCG GTC GCC GTG CTG CCC TGT CAT
     CAT GTA GGA CTT GGT CTT GTC AGC CAG CGG CAC GAC GGG ACA GTA

811  CTA CGC TAA GAT CCT CGG CAT CCT GAC GGA GCT GCG GAC CCT GGG
     GAT GCG ATT CTA GGA GCC GTA GGA CTG CCT CGA CGC CTG GGA CCC

856  CAT GCA GAA CTC CAA CAT GTG CAT CTC ACT CAA GCT GAA GAA CAG
     GTA CGT CTT GAG GTT GTA CAC GTA GAG TGA GTT CGA CTT CTT GTC

901  GAA CGT GCC GCC GTT CTT CGA GGA TAT CTG GGA CGT CCT CGA GTA
     CTT GCA CGG CGG CAA GAA GCT CCT ATA GAC CCT GCA GGA GCT CAT

946  AAA
     TTT
```

Total number of bases is: 948.

Fig.41.

Sequence I.D. 7

Sequence comparison between Heliothis 19R clone and SEcR Taq clon

```
HEcR   RPECVVPENQCAMKRKEKKAQREKDKLPVSTTTVDDHMPPIMQCDPPPPEAARILECVQ
SEcR   RPECVVPENQCAMKRKEKKAQREKDKLPVSTTTVDDHMPPIMQCDPPPPEAARI

HEcR   HEVVPRFLNEKLMEQNRLKNVPPLTANQKSLIARLVWYQEGYEQPSEEDLKRVTQSD
SEcR   HEVVPRFLNEKLMERTRLRNVPPLTANQKSLIARLVWYQEGYEQPSEEDLKRVTQSD

HEcR   EDDEDSDMPFRQITEMTILTVQLIVEFAKGLPGFAKISQSDQITLLKACSSEVMMLR
SEcR   EDEEESDMPFRQITEMTILTVQLIVEFAKGLPAFAKISQSDQITLLKACSSEVMMLR

HEcR   VARRYDAATDSVLFANNQAYTRDNYRKAGMAYVIEDLLHFCRCMYSMMMDNVHYALL
SEcR   VARRYDAATDSVLFANNQAYTRDNYRKAGMAYVIEDLLHFCRCMYSMMMDNVHYALL

HEcR   TAIVIFSDRPGLEQPLLVEEIQRYYLNTLRVYILNQNSASPRGAVIFGEILGILTEI
SEcR   TAIVIFSDRPGLELTLLVEEIQRYYLNTLRVYILNQNSRSPCCPVIYAKILGILTEL

HEcR   RTLGMQNSNMCISLKLKKRKLPPFLEEIDWDV
SEcR   RTLGMQNSNMCISLKLKNRNVPPFFEDIDWDV
```

HELIOTHIS ECDYSONE RECEPTOR

This is a division of application Ser. No. 08/653,648, filed May 24, 1996, now U.S. Pat. No. 6,379,945.

The present invention relates to the identification and characterisation of insect steroid receptors from the Lepidoptera species *Heliothis virescens*, and the nucleic acid encoding therefor. The present invention also relates to the use of such receptors, and such nucleic acid, particularly, but not exclusively, in screening methods, and gene switches. By gene switch we mean a gene sequence which is responsive to an applied exogenous chemical inducer enabling external control of expression of the gene controlled by said gene sequence.

Lipophilic hormones such as steroids induce changes in gene expression to elicit profound effects on growth, cellular differentiation, and homeostasis. These hormones recognise intracellular receptors that share a common modular structure consisting of three main functional domains: a variable amino terminal region that contains a transactivation domain, a DNA binding domain, and a ligand binding domain on the carboxyl side of the molecule. The DNA binding domain contains nine invariant cysteines, eight of which are involved in zinc coordination to form a two-finger structure. In the nucleus the hormone-receptor complex binds to specific enhancer-like sequences called hormone response elements (HREs) to modulate transcription of target genes.

The field of insect steroid research has undergone a revolution in the last three years as a result of the cloning and preliminary characterisation of the first steroid receptor member genes. These developments suggest the time is ripe to try to use this knowledge to improve our tools in the constant fight against insect pests. Most of the research carried out on the molecular biology of the steroid receptor superfamily has been on *Drosophila melanogaster* (Diptera), see for example International Patent Publication No WO91/13167, with some in Manduca and Galleria (Lepidoptera).

It has been three decades since 20-hydroxyecdysone was first isolated and shown to be involved in the regulation of development of insects. Since then work has been carried out to try to understand the pathway by which this small hydrophobic molecule regulates a number of activities. By the early 1970s, through the studies of Clever and Ashburner, it was clear that at least in the salivary glands of third instar Drosophila larvae, the application of ecdysone lead to the reproducible activation of over a hundred genes. The ecdysone receptor in this pathway is involved in the regulation of two classes of genes: a small class (early genes) which are induced by the ecdysone receptor and a large class (late genes) which are repressed by the ecdysone receptor. The early class of genes are thought to have two functions reciprocal to those of the ecdysone receptor; the repression of the early transcripts and the induction of late gene transcription. Members of the early genes so far isolated and characterised belong to the class of molecules with characteristics similar to known transcription factors. They are thus predicted to behave as expected by the model of ecdysone action (Ashburner, 1991). More recently, the early genes E74 and E75 have been shown to bind both types of ecdysone inducible genes (Thummel et al., 1990; Segraves and Hogness, 1991), thus supporting their proposed dual activities. It should be noted however, that the activation of a hierarchy of genes is not limited to third instar larvae salivary glands, but that the response to the ecdysone peak at the end of larval life is observed in many other tissues, such as the imaginal disks (i.e. those tissues which metamorphose to adult structures) and other larval tissues which histolyse at the end of larval life (eg. larval fat body). The model for ecdysone action as deduced by studying the third instar chromosome puffing may not apply to the activation of ecdysone regulated genes in adults. In other words, the requirement for other factors in addition to the active ecdysone receptor must be satisfied for correct developmental expression (e.g. the Drosophila yolk protein gene expression in adults is under control of doublesex, the last gene in the sex determination gene hierarchy).

The ecdysone receptor and the early gene E75 belong to the steroid receptor superfamily. Other Drosophila genes, including ultraspiracle, tailless, sevenup and FTZ-FI, also belong to this family. However, of all these genes only the ecdysone receptor is known to have a ligand, and thus the others are known as orphan receptors. Interestingly, despite the ultraspiracle protein ligand binding region sharing 49% identity with the vertebrate retinoic X receptor (RXR) ligand binding region (Oro et al., 1990), they do not share the same ligand (i.e. the RXR ligand is 9-cis retinoic acid) (Heymann et al., 1992 and Mangelsdorf et al., 1992). All the Drosophila genes mentioned are involved in development, ultraspiracle for example, is required for embryonic and larval abdominal development. The protein products of these genes all fit the main features of the steroid receptor superfamily (Evans, 1988; Green and Chambon, 1988, Beato, 1989) i.e. they have a variable N terminus region involved in ligand independent transactivation (Domains A and B), a highly conserved 66–68 amino acid region which is responsible for the binding of DNA at specific sites (Domain C), a hinge region thought to contain a nuclear translocation signal (Domain D), and a well conserved region containing the ligand binding region, transactivation sequences and the dimerisation phase (Domain E). The last region, domain F, is also very variable and its function is unknown.

Steroid receptor action has been elucidated in considerable detail in vertebrate systems at both the cellular and molecular levels. In the absence of ligand, the receptor molecule resides in the cytoplasm where it is bound by Hsp90, Hsp70, and p59 to form the inactive complex (Evans, 1988). Upon binding of the ligand molecule by the receptor a conformational change takes place which releases the Hsp90, Hsp70 and p59 molecules, while exposing the nuclear translocation signals in the receptor. The ligand dependent conformational change is seen in the ligand binding domain of both progesterone and retinoic acid receptors (Allan et al., 1992a). This conformational change has been further characterised in the progesterone receptor and was found to be indispensable for gene transactivation (Allan et al., 1992b). Once inside the nucleus the receptor dimer binds to the receptor responsive element at a specific site on the DNA resulting in the activation or repression of a target gene. The receptor responsive elements usually consist of degenerate direct repeats, with a spacer between 1 and 5 nucleotides, which are bound by a receptor dimer through the DNA binding region (Domain C).

Whereas some steroid hormone receptors are active as homodimers others act as heterodimers. For example, in vertebrates, the retinoic acid receptor (RAR) forms heterodimers with the retinoic X receptor (RXR). RXR can also form heterodimers with the thyroid receptor, vitamin D receptor (Yu et al., 1991; Leid et al., 1992) and peroxisome activator receptor (Kliewer et al., 1992). Functionally the main difference between homodimers and heterodimers is increased specificity of binding to specific response elements. This indicates that different pathways can be linked, coordinated and modulated, and more importantly this observation begins to explain the molecular basis of the pleotropic activity of retinoic acid in vertebrate development (Leid et al., 1992b). Similarly, the Drosophila ultraspiracle gene product was recently shown to be capable of forming heterodimers with retinoic acid, thyroid, vitamin D and peroxisome activator receptors and to stimulate the binding of these receptors to their target responsive elements (Yao et al., 1993). More significantly, the ultraspiracle gene product has also been shown to form heterodimers with the ecdysone receptor, resulting in cooperative binding to the ecdysone response element and capable of rendering mammalian cells ecdysone responsive (Yao et al., 1992). The latter is of importance since transactivation of the ecdysone gene alone in mammalian cells fails to elicit an ecdysone response (Koelle et al., 1991), therefore suggesting that the ultraspiracle gene product is an integral component of a functional ecdysone receptor (Yao et al., 1992). It is possible that the ultraspiracle product competes with other steroid receptors or factors to form heterodimers with the ecdysone receptor. Moreover it remains to be investigated if ultraspiracle is expressed in all tissues of the Drosophila larvae. Despite ultraspiracle being necessary to produce a functional ecdysone receptor, the mechanism by which this activation takes place is as yet undetermined.

We have now isolated and characterised the ecdysone steroid receptor from *Heliothis virescens* (hereinafter HEcR). We have found that surprisingly unlike the Drosophila ecdysone steroid receptor (hereinafter DEcR), in reports to-date, HEcR can be induced by known non-steroidal inducers. It will be appreciated that this provides many advantages for the system.

Steroids are difficult and expensive to make. In addition, the use of a non-steroid as the inducer allows the system to be used in agrochemical and pharmaceutical applications, not least because it avoids application of a steroid which is already present in insects and/or mammals. For example, it would not be feasible to use a gene switch in a mammalian cell which was induced by a naturally occurring steroidal inducer. It will also be appreciated that for environmental reasons it is advantageous to avoid the use of steroids as inducers.

According to one aspect of the present invention there is provided DNA having the sequence shown in Seq ID No. 2, wherein Seq ID No 2 gives the sequence for the HEcR.

According to another aspect of the present invention there is provided DNA having part of the sequence shown in Seq ID No. 2, which encodes for the HEcR ligand binding domain.

According to another aspect of the present invention there is provided DNA having part of the sequence shown in Seq ID No. 2, which encodes for the HEcR DNA binding domain.

According to yet another aspect of the present invention there is provided DNA having part of the sequence shown in Seq ID No. 2, which encodes for the HEcR transactivation domain.

According to a further aspect of the present invention there is provided DNA having part of the sequence shown in Seq ID No. 2, which encodes for the HEcR hinge domain.

According to a still further aspect of the present invention there is provided DNA having part of the sequence shown in Seq ID No. 2, which encodes for the HEcR carboxy terminal region.

According to one aspect of the present invention there is provided DNA having the sequence shown in Seq ID No. 3, wherein Seq ID No 3 gives the sequence for the HEcR.

According to another aspect of the present invention there is provided DNA having part of the sequence shown in Seq ID No. 3, which encodes for the HEcR ligand binding domain.

According to another aspect of the present invention there is provided DNA having part of the sequence shown in Seq ID No. 3, which encodes for the HEcR DNA binding domain.

According to yet another aspect of the present invention there is provided DNA having part of the sequence shown in Seq ID No. 3, which encodes for the HEcR transactivation domain.

According to a further aspect of the present invention there is provided DNA having part of the sequence shown in Seq ID No. 3, which encodes for the HEcR hinge domain.

According to a still further aspect of the present invention there is provided DNA having part of the sequence shown in Seq ID No. 3, which encodes for the HEcR carboxy terminal region.

According to one aspect of the present invention there is provided DNA having the sequence shown in Seq ID No. 4, wherein Seq ID No 4 gives the sequence for the HEcR.

According to another aspect of the present invention there is provided DNA having part of the sequence shown in Seq ID No. 4, which encodes for the HEcR ligand binding domain.

According to another aspect of the present invention there is provided DNA having part of the sequence shown in Seq ID No. 4, which encodes for the HEcR DNA binding domain.

According to yet another aspect of the present invention there is provided DNA having part of the sequence shown in Seq ID No. 4, which encodes for the HEcR transactivation domain.

According to a further aspect of the present invention there is provided DNA having part of the sequence shown in Seq ID No. 4, which encodes for the HEcR hinge domain.

According to a still further aspect of the present invention there is provided DNA having part of the sequence shown in Seq ID No. 4, which encodes for the HEcR carboxy terminal region.

As mentioned above, steroid receptors are eukaryotic transcriptional regulatory factors which, in response to the binding of the steroid hormone, are believed to bind to specific DNA elements and activate transcription. The steroid receptor can be divided into six regions, designated A to F, using alignment techniques based on shared homology with other members of the steroid hormone receptor superfamily. Krust et al identified two main regions in the receptor, C and E. Region C is hydrophilic and is unusual in its high content in cysteine, lysine and arginine. It corresponds to a DNA-binding domain, sometimes referred to as the "zinc finger". It is the DNA binding domain which binds to the upstream DNA of the responsive gene. Such upstream DNA is known as the hormone response element or HRE for short. Region E is hydrophobic and is identified as the hormone (or ligand) binding domain. Region E can be further subdivided into regions E1, E2 and E3.

The region D, which separates domains C and E is highly hydrophobic and is flexible. It is believe that communication between domains E and C involves direct contact between them through region D, which provides a hinge between the two domains. Region D is therefore referred to as the hinge domain.

The mechanism of the receptor appears to require it to interact with some element(s) of the transcription machinery over and above its interactions with the hormone and the hormone response element. N-terminal regions A and B perform such a function and are jointly known as the transactivation domain. The carboxy terminal region is designated F.

The domain boundaries of the HEcR can be defined as follows:

|  | INTERVALS | |
| --- | --- | --- |
| DOMAIN | base pairs | amino acids |
| Transactivating (A/B) | 114–600 | 1–162 |
| DNA Binding (C) | 601–798 | 163–228 |
| Hinge (D) | 799–1091 | 229–326 |
| Ligand Binding (E) | 1092–1757 | 327–545 |
| C-Terminal End (F) | 1758–1844 | 546–577 |

The DNA binding domain is very well defined and is 66 amino acids long, thus providing good boundaries. The above intervals have been defined using the multiple alignment for the ecdysone receptors (FIG. 5).

The present invention also includes DNA which shows homology to the sequences of the present invention. Typically homology is shown when 60% or more of the nucleotides are common, more typically 65%, preferably 70%, more preferably 75%, even more preferably 80% or 85%, especially preferred are 90%, 95%, 98% or 99% or more homology.

The present invention also includes DNA which hybridises to the DNA of the present invention and which codes for at least part of the Heliothis ecdysone receptor transactivation domain, DNA binding domain, hinge domain, ligand binding domain and/or carboxy terminal region. Preferably such hybridisation occurs at, or between, low and high stringency conditions. In general terms, low stringency conditions can be defined as 3×SCC at about ambient temperature to about 65° C., and high stringency conditions as 0.1×SSC at about 65° C. SSC is the name of a buffer of 0.15M NaCl, 0.015M trisodium citrate. 3×SSC is three time as strong as SSC and so on.

The present invention further includes DNA which is degenerate as a result of the genetic code to the DNA of the present invention and which codes for a polypeptide which is at least part of the Heliothis ecdysone receptor transactivation domain, DNA binding domain, hinge domain, ligand binding domain and/or carboxy terminal region.

The DNA of the present invention may be cDNA or DNA which is in an isolated form.

According to another aspect of the present invention there is provided a polypeptide comprising the Heliothis ecdysone receptor or a fragment thereof, wherein said polypeptide is substantially free from other proteins with which it is ordinarily associated, and which is coded for by any of the DNA of the present invention.

According to another aspect of the present invention there is provided a polypeptide which has the amino acid sequence of Seq ID No. 4 or any allelic variant or derivative thereof, wherein Seq ID No. 4 gives the amino acid sequence of the HEcR polypeptide.

According to another aspect of the present invention there is provided a polypeptide which has part of the amino acid sequence of Seq ID No. 4 or any allelic variant or derivative thereof, which sequence provides the HEcR ligand binding domain.

According to another aspect of the present invention there is provided a polypeptide which has part of the amino acid sequence of Seq ID No. 4 or any allelic variant or derivative thereof, which sequence provides the HEcR DNA binding domain.

According to yet another aspect of the present invention there is provided a polypeptide which has part of the amino acid sequence of Seq ID No. 4 or any allelic variant or derivative thereof, which sequence provides the HEcR transactivation domain.

According to a further aspect of the present invention there is provided a polypeptide which has the amino acid sequence of a part of Seq ID No. 4 or any allelic variant or derivative thereof, which sequence provides the HEcR hinge domain.

According to a still further aspect of the present invention there is provided a polypeptide which has the amino acid sequence of a part of Seq ID No. 4 or any allelic variant or derivative thereof, which sequence provides the HEcR carboxy terminal region.

For the avoidance of doubt, spliced variants of the amino acid sequences of the present invention are included in the present invention.

Preferably, said derivative is a homologous variant which has conservative amino acid changes. By conservation amino acid changes we mean replacing an amino acid from one of the amino acid groups, namely hydrophobic, polar, acidic or basic, with an amino acid from within the same group. An examples of such a change is the replacement of valine by methionine and vice versa.

According to another aspect of the present invention there is provided a fusion polypeptide comprising at least one of the polypeptides of the present invention functionally linked to an appropriate non-Heliothis ecdysone receptor domain(s).

According to an especially preferred embodiment of the present invention the HEcR ligand binding domain of the present invention is fused to a DNA binding domain and a transactivation domain.

According to another embodiment of the present invention the DNA binding domain is fused to a ligand binding domain and a transactivation domain.

According to yet another embodiment of the present invention the transactivation domain is fused to a ligand binding domain and a DNA binding domain.

The present invention also provides recombinant DNA encoding for these fused polypeptides.

According to an especially preferred embodiment of the present invention there is provided recombinant nucleic acid comprising a DNA sequence encoding the HEcR ligand binding domain functionally linked to DNA encoding the DNA binding domain and transactivation domain from a glucocorticoid receptor.

According to yet another aspect of the present invention there is provided recombinant nucleic acid comprising a DNA sequence comprising a reporter gene operably linked to a promoter sequence and a hormone response element which hormone response element is responsive to the DNA bonding domain encoded by the DNA of of the present invention.

According to another aspect of the present invention there is provided a construct transformed with nucleic acid, recombinant DNA, a polypeptide or a fusion polypeptide of the present invention. Such constructs include plasmids and phages suitable for transforming a cell of interest. Such constructs will be well known to those skilled in the art.

According to another aspect of the present invention there is provided a cell transformed with nucleic acid, recombinant DNA, a polypeptide, or a fusion polypeptide of the present invention.

Preferably the cell is a plant, fungus or mammalian cell.

For the avoidance of doubt fungus includes yeast.

The present invention therefore provides a gene switch which is operably linked to a foreign gene or a series of foreign genes whereby expression of said foreign gene or said series of foreign genes may be controlled by application of an effective exogenous inducer.

Analogs of ecdysone, such as Muristerone A, are found in plants and disrupt the development of insects. It is therefore proposed that the receptor of the present invention can be used be in plants transformed therewith as an insect control mechanism. The production of the insect-damaging product being controlled by an exogenous inducer. The insect-damaging product can be ecdysone or another suitable protein.

The first non-steroidal ecdysteroid agonists, dibenzoyl hydrazines, typified by RH-5849 [1,2-dibenzoyl, 1-tert-butyl hydrazide], which is commercially available as an insecticide from Rohm and Haas, were described back in 1988. Another commercially available compound in this series is RH-5992 [tebufenozide, 3,5-dimethylbenzoic acid 1-1 (1,1-diethylethyl)-2(4-ethylbenzoyl)hydrazide]. These compounds mimic 20-hydroxyecdysone (20E) in both *Manduca sexta* and *Drosophila melanogaster*. These compounds have the advantage that they have the potential to control insects using ecdysteroid agonists which are non-steroidal. Further Examples of such dibenzoyl hydrazines are given in U.S. Pat. No. 5,117,057 to Rohm and Haas, and Oikawa et al, Pestic Sci, 41, 139–148 (1994). However, it will be appreciated that any inducer of the gene switch of the present invention, whether steroidal or non-steroidal, and which is currently or becomes available, may be used.

The gene switch of the present invention, then, when linked to an exogenous or foreign gene and introduced into a plant by transformation, provides a means for the external regulation of expression of that foreign gene. The method employed for transformation of the plant cells is not especially germane to this invention and any method suitable for the target plant may be employed. Transgenic plants are obtained by regeneration from the transformed cells. Numerous transformation procedures are known from the literature such as agroinfection using *Agrobacterium tumefaciens* or its Ti plasmid, electroporation, microinjection or plants cells and protoplasts, microprojectile transformation, to mention but a few. Reference may be made to the literature for full details of the known methods.

Neither is the plant species into which the chemically inducible sequence is inserted particularly germane to the invention. Dicotyledonous and monocotyledonous plants can be transformed. This invention may be applied to any plant for which transformation techniques are, or become, available. The present invention can therefore be used to control gene expression in a variety of genetically modified plants, including field crops such as canola, sunflower, tobacco, sugarbeet, and cotton; cereals such as wheat, barley, rice, maize, and sorghum; fruit such as tomatoes, mangoes, peaches, apples, pears, strawberries, bananas and melons; and vegetables such as carrot, lettuce, cabbage and onion. The switch is also suitable for use in a variety of tissues, including roots, leaves, stems and reproductive tissues.

In a particularly preferred embodiment of the present invention, the gene switch of the present invention is used to control expression of genes which confer resistance herbicide resistance and/or insect tolerance to plants.

Recent advances in plant biotechnology have resulted in the generation of transgenic plants resistant to herbicide application, and transgenic plants resistant to insects. Herbicide tolerance has been achieved using a range of different transgenic strategies. One well documented example in the herbicide field is the use the bacterial xenobiotic detoxifying gene phosphinothricin acetyl transferase (PAT) from *Streptomyces hydroscopicus*. Mutated genes of plant origin, for example the altered target site gene encoding acetolactate synthase (ALS) from Arabidopsis, have been successfully utilised to generate transgenic plants resistant to herbicide application. The PAT and ALS genes have been expressed under the control of strong constitutive promoter. In the field of insecticides, the most common example to-date is the use of the Bt gene.

We propose a system where genes conferring herbicide and/or insect tolerance would be expressed in an inducible manner dependent upon application of a specific activating chemical. This approach has a number of benefits for the farmer, including the following:

1. Inducible control of herbicide and/or insect tolerance would alleviate any risk of yield penalties associated with high levels of constitutive expression of herbicide and/or insect resistance genes. This may be a particular problem as early stages of growth where high levels of transgene product may directly interfere with normal development. Alternatively high levels of expression of herbicide and/or insect resistance genes may cause a metabolic drain for plant resources.
2. The expression of herbicide resistance genes in an inducible manner allows the herbicide in question to be used to control volunteers if the activating chemical is omitted during treatment.
3. The use of an inducible promoter to drive herbicide and/or insect resistance genes will reduce the risk of resistance becoming a major problem. If resistance genes were passed onto weed species from related crops, control could still be achieved with the herbicide in the absence of inducing chemical. This would particularly be relevant if the tolerance gene confirmed resistance to a total vegetative control herbicide which would be used (with no inducing chemical) prior to sowing the crop and potentially after the crop has been harvested. For example, it can be envisaged that herbicide resistance cereals, such as wheat, might outcross into the weed wild oats, thus conferring herbicide resistance to this already troublesome weed. A further example is that the inducible expression of herbicide resistance in sugar beet will reduce the risk of wild sugar beet becoming a problem. Similarly, in the field of insect control, insect resistance may well become a problem if the tolerance gene is constitutively expressed. The used of an inducible promoter will allow a greater range of insect resistance control mechanisms to be employed.

This strategy of inducible expression of herbicide resistance can be achieved with a pre-spray of chemical activator or in the case of slow acting herbicides, for example N-phosphonomethyl-glycine (commonly known as glyphosate), the chemical inducer can be added as a tank mix simultaneously with the herbicide. Similar strategies can be employed for insect control.

This strategy can be adopted for any resistance confering gene/corresponding herbicide combination, which is, or becomes, available. For example, the gene switch of the present invention can be used with:

1. Maize glutathione S-transferase (GST-27) gene (see our International Patent Publication No WO90/08826), which confers resistance to chloroacetanilide herbicides such as acetochlor, metolachlor and alachlor.

2. Phosphinotricin acetyl transferase (PAT), which confers resistance to the herbicide commonly known as glufosinate.
3. Acetolactate synthase gene mutants from maize (see our International Patent Publication No WO90/14000) and other genes, which confer resistance to sulphonyl urea and imadazolinones.
4. Genes which confer resistance to glyphosate. Such genes include the glyphosate oxidoreductase gene (GOX) (see International Patent Publication No. WO92/00377); genes which encode for 5-enolpyruvyl-3-phosphoshikimic acid synthase (EPSPS), including Class I and Class II EPSPS, genes which encode for mutant EPSPS, and genes which encode for EPSPS fusion peptides such as that comprised of a chloroplast transit peptide and EPSPS (see for example EP 218 571, EP 293 358, WO91/04323, WO92/04449 and WO92/06201); and genes which are involved in the expression of CPLyase.

Similarly, the strategy of inducible expression of insect resistance can be adopted for any tolerance confering gene which is, or becomes, available.

The gene switch of the present invention can also be used to controlled expression of foreign proteins in yeast and mammalian cells. Many heterologous proteins for many applications are produced by expression in genetically engineered bacteria, yeast cells and other eucaryotic cells such as mammalian cells.

As well as the obvious advantage in providing control over the expression of foreign genes in such cells, the switch of the present invention provides a further advantage in yeasts and mammalian cells where accumulation of large quantities of an heterologous protein can damage the cells, or where the heterologous protein is damaging such that expression for short periods of time is required in order to maintain the viability of the cells.

Such an inducible system also has applicability in gene therapy allowing the timing of expression of the therapeutic gene to be controlled. The present invention is therefore not only applicable to transformed mammalian cells but also to mammals per se.

A further advantage of the inducible system of the present invention in mammalian cells is that, because it is derived from a insect, there is less chance of it being effected by inducers which effect the natural mammalian steroid receptors.

In another aspect of the present invention the gene switch is used to switch on genes which produce potentially damaging or lethal proteins. Such a system can be employed in the treatment of cancer in which cells are transformed with genes which express proteins which are lethal to the cancer. The timing of the action of such proteins on the cancer cells can be controlled using the switch of the present invention.

The gene switch of the present invention can also be used to switch genes off as well as on. This is useful in disease models. In such a model the cell is allowed to grow before a specific gene(s) is switched off using the present invention. Such a model facilitates the study of the effect of a specific gene(s).

Again the method for producing such transgenic cells is not particularly germane to the present invention and any method suitable for the target cell may be used; such methods are known in the art, including cell specific transformation.

As previously mentioned, modulation of gene expression in the system appears in response to the binding of the HEcR to a specific control, or regulatory, DNA element. A schematic representation of the HEcR gene switch is shown in FIG. 6. For ease of reference, the schematic representation only shows three main domains of the HEcR, namely the transactivation domain, DNA binding domain and the ligand binding domain. Binding of a ligand to the ligand binding domain enables the DNA binding domain to bind to the HRE resulting in expression (or indeed repression) of a target gene.

The gene switch of the present invention can therefore be seen as having two components. The first component comprising the HEcR and a second component comprising an appropriate HRE and the target gene. In practice, the switch may conveniently take the form of one or two sequences of DNA. At least part of the one sequence, or one sequence of the pair, encoding the HEcR protein. Alternatively, the nucleic acid encoding the HEcR can be replaced by the protein/polypeptide itself.

Not only does the switch of the present invention have two components, but also one or more of the domains of the receptor can be varied producing a chimeric gene switch. The switch of the present invention is very flexible and different combinations can be used in order to vary the result/to optimise the system. The only requirement in such chimeric systems is that the DNA binding domain should bind to the hormone response element in order to produce the desired effect.

The glucocorticoid steroid receptor is well characterised and has been found to work well in plants. A further advantage of this receptor is that it functions as a homodimer. This means that there is no need to express a second protein such as the ultraspiracle in order to produce a functional receptor. The problem with the glucocorticoid steroid receptor is that ligands used to activate it are not compatible with agronomic practice.

In a preferred aspect of the present invention the receptor comprises glucocorticoid receptor DNA binding and transactivation domains with a Heliothis ligand binding domain according to the present invention. The response unit preferably comprising the glucocorticoid hormone response element and the desired effect gene. In the Examples, for convenience, this effect gene took the form of a reporter gene. However, in non-test or non-screen situations the gene will be the gene which produces the desired effect, for example produces the desired protein. This protein may be a natural or exogenous protein. It will be appreciated that this chimeric switch combines the best features of the glucocorticoid system, whilst overcoming the disadvantage of only being inducible by a steroid.

In another preferred embodiment, the Heliothis ligand binding domain is changed, and preferably replaced with a non-Heliothis ecdysone receptor ligand binding domain. For example, we have isolated suitable sequences from *Spodoptera exigua*.

Thus, according to another aspect of the present invention there is provided DNA having the sequence shown in Seq ID No. 6.

According to another aspect of the present invention there is provided DNA having part of the sequence shown in Seq ID No. 6, which encodes for the Spodoptera ecdysone ligand binding domain.

According to another aspect of the present invention there is provided DNA having part of the sequence shown in Seq ID No. 6, which encodes for the Spodoptera ecdysone hinge domain.

The present invention also provides the polypeptides coded for by the above DNA sequences of Seq ID No. 6.

A further advantage with such chimeric systems is that they allow you to choose the promoter which is used to drive the effector gene according to the desired end result. For example, placing the foreign gene under the control of a cell specific promoter can be particularly advantageous in circumstances where you wish to control not only the timing of expression, but also which cells expression occurs in. Such a double control can be particularly important in the areas of gene therapy and the use of cytotoxic proteins.

Changing the promoter also enables gene expression to be up- or down-regulated as desired.

Any convenient promoter can be used in the present invention, and many are known in the art.

Any convenient transactivation domain may also be used. The transactivation domain VP16 is a strong activator from Genentech Inc., and is commonly used when expressing glucocorticoid receptor in plants. Other transactivation domains derived for example from plants or yeast may be employed.

In a preferred embodiment of the present invention, the DNA binding domain is the glucocorticoid DNA binding domain. This domain is commonly a human glucocorticoid receptor DNA binding domain. However, the domain can be obtained from any other convenient source, for example, rats.

According to another aspect of the present invention there is provided a method of selecting compounds capable of being bound to an insect steroid receptor superfamily member comprising screening compounds for binding to a polypeptide or fusion polypeptide of the present invention, and selecting said compounds exhibiting said binding.

According to another aspect of the present invention there is provided a compound selected using the method of the present invention.

According to another aspect of the present invention there is provided an agricultural or pharmaceutical composition comprising the compound of the present invention.

According to yet another aspect of the present invention there is provided the use of the compound of the present invention as a pesticide, pharmaceutical and/or inducer of the switch. It will be appreciated that such inducers may well be useful as insecticides in themselves.

According to a further aspect of the present invention there is provided a method of producing a protein or peptide or polypeptide comprising introducing into a cell of the present invention, a compound which binds to the ligand binding domain in said cell.

Various preferred features and embodiments of the present invention will now be described by way of non-limiting example with reference to the accompanying examples and figures, in which figures:

FIG. 1 (Sequence ID No. 1) shows the DNA sequence amplified from first strand cDNA made from mRNA isolated from *Heliothis virescens* Fourth instar larvae. The complementary sequence (Sequence ID No. 60) is also shown. The underlined sequences refer to the position of the degenerate oligonucleotides. At the 5' end the sequence matches that of the oligonucleotide while at the 3' end 12 nucleotides of the original oligonucleotide are observed;

FIG. 2 (Sequence ID No. 2) shows the DNA sequence contained with the clone pSK19R isolated from a random primed cDNA *Heliothis virescens* library (Complimentary sequence, Sequence ID No. 6, is also shown); Sequence is flanked by EcoRI sites;

FIG. 3 (Sequence ID No. 3) shows the DNA sequence contained with the clone pSK16.1 isolated from a random primed cDNA *Helidthis virescens* library (Complimentary sequence, Sequence ID No. 62, is also shown);

Figure 6:
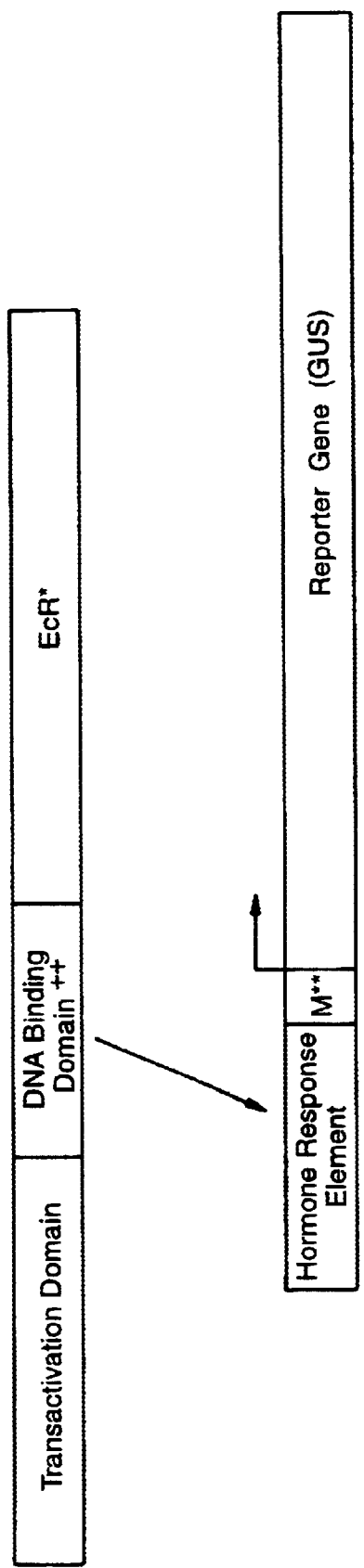
Figure 7:
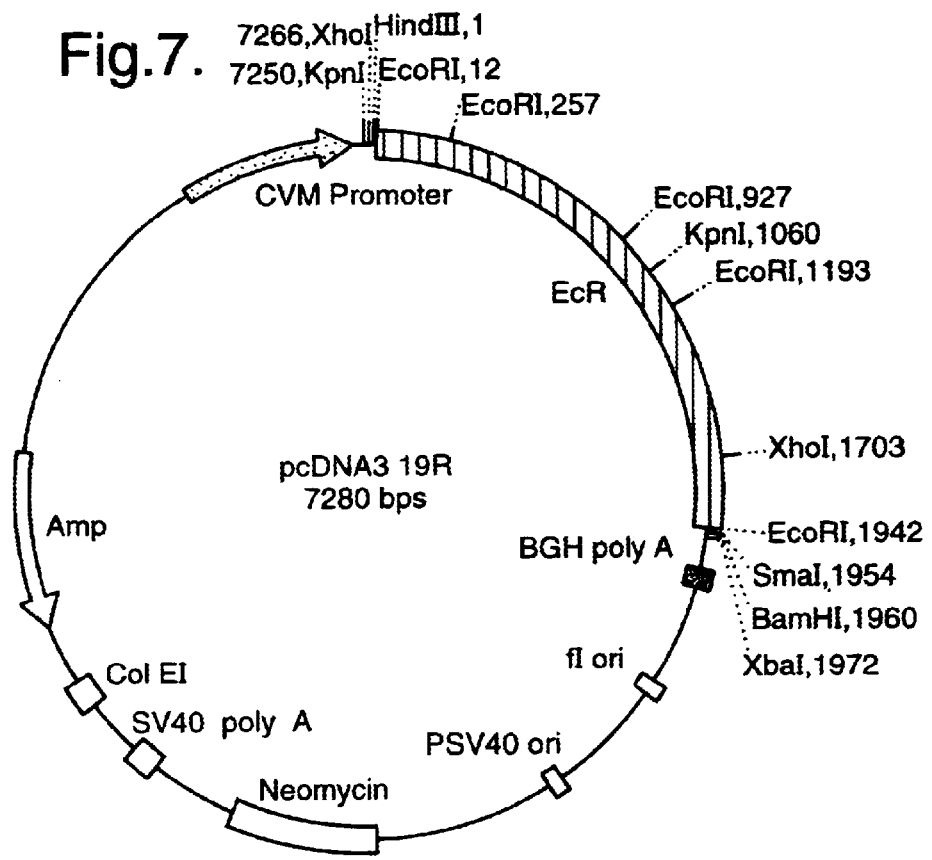
Figure 8:
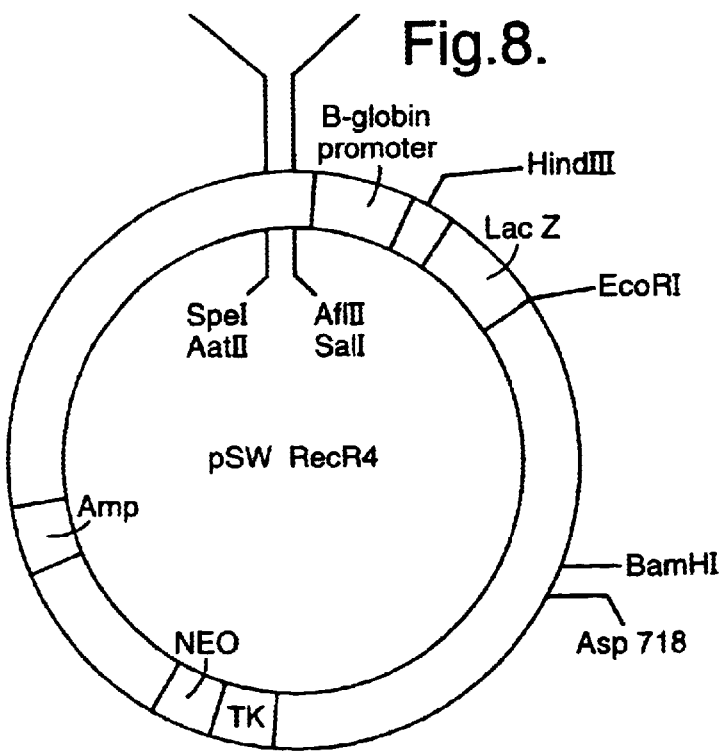
Figure 9:
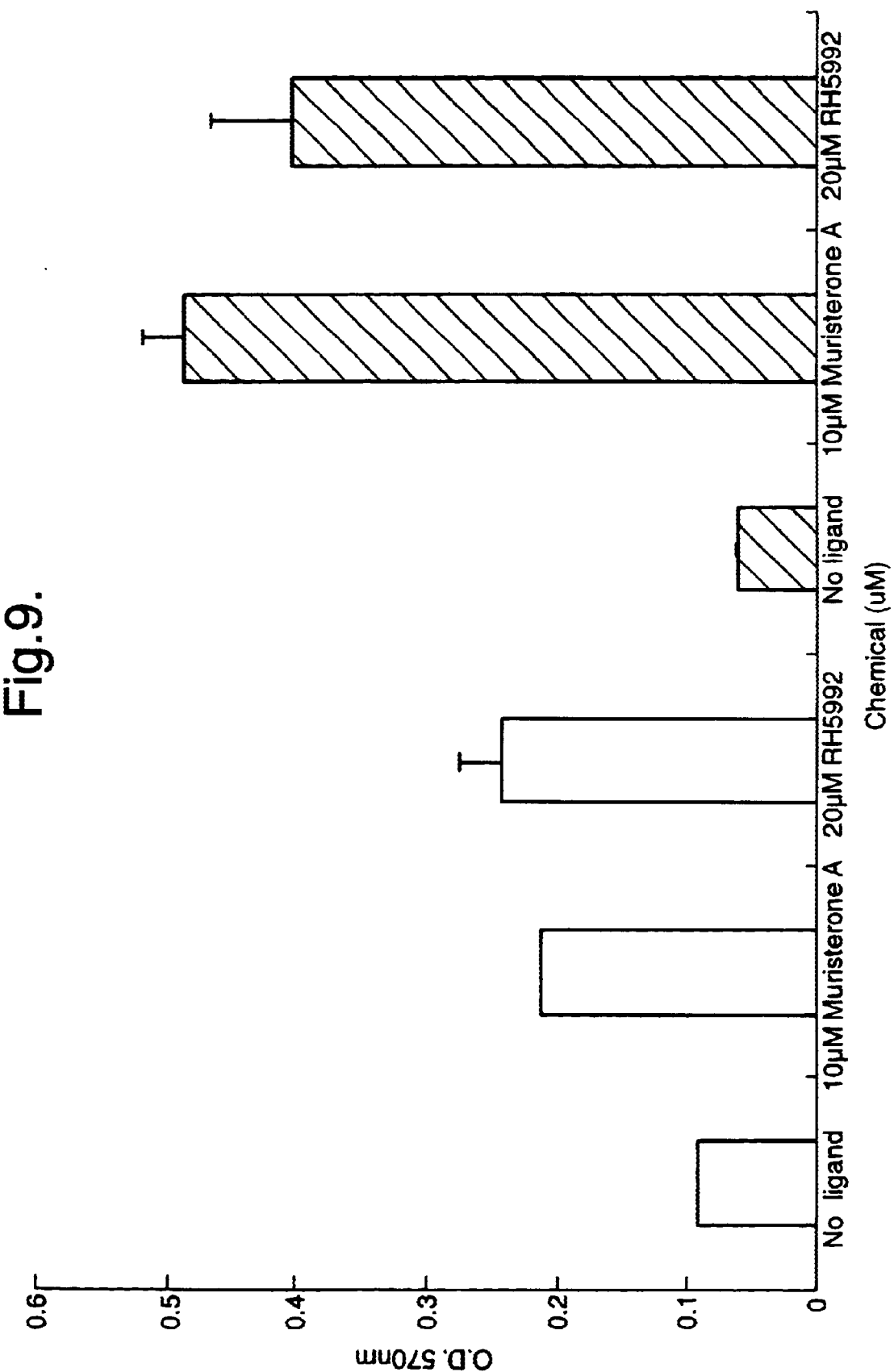
Figure 10:
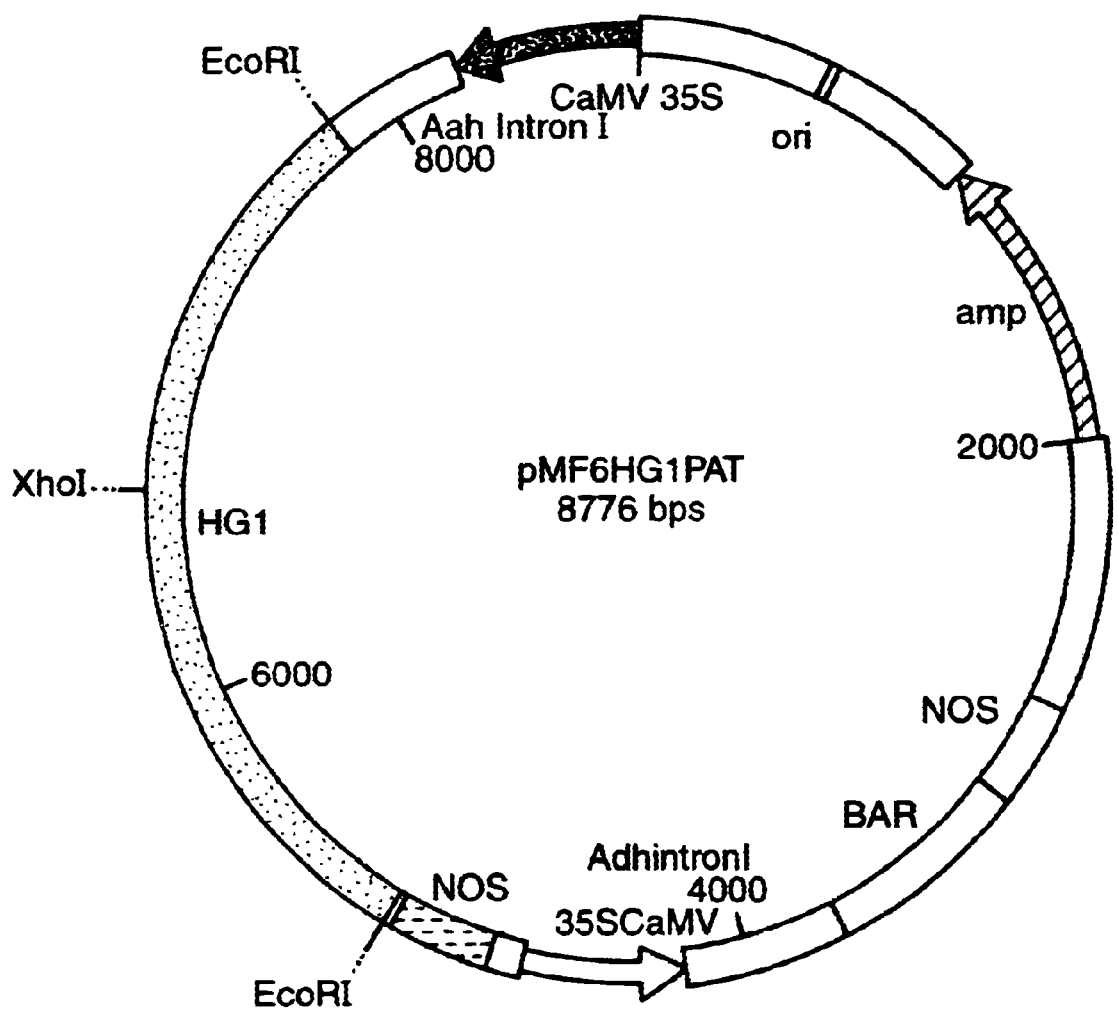
Figure 11:
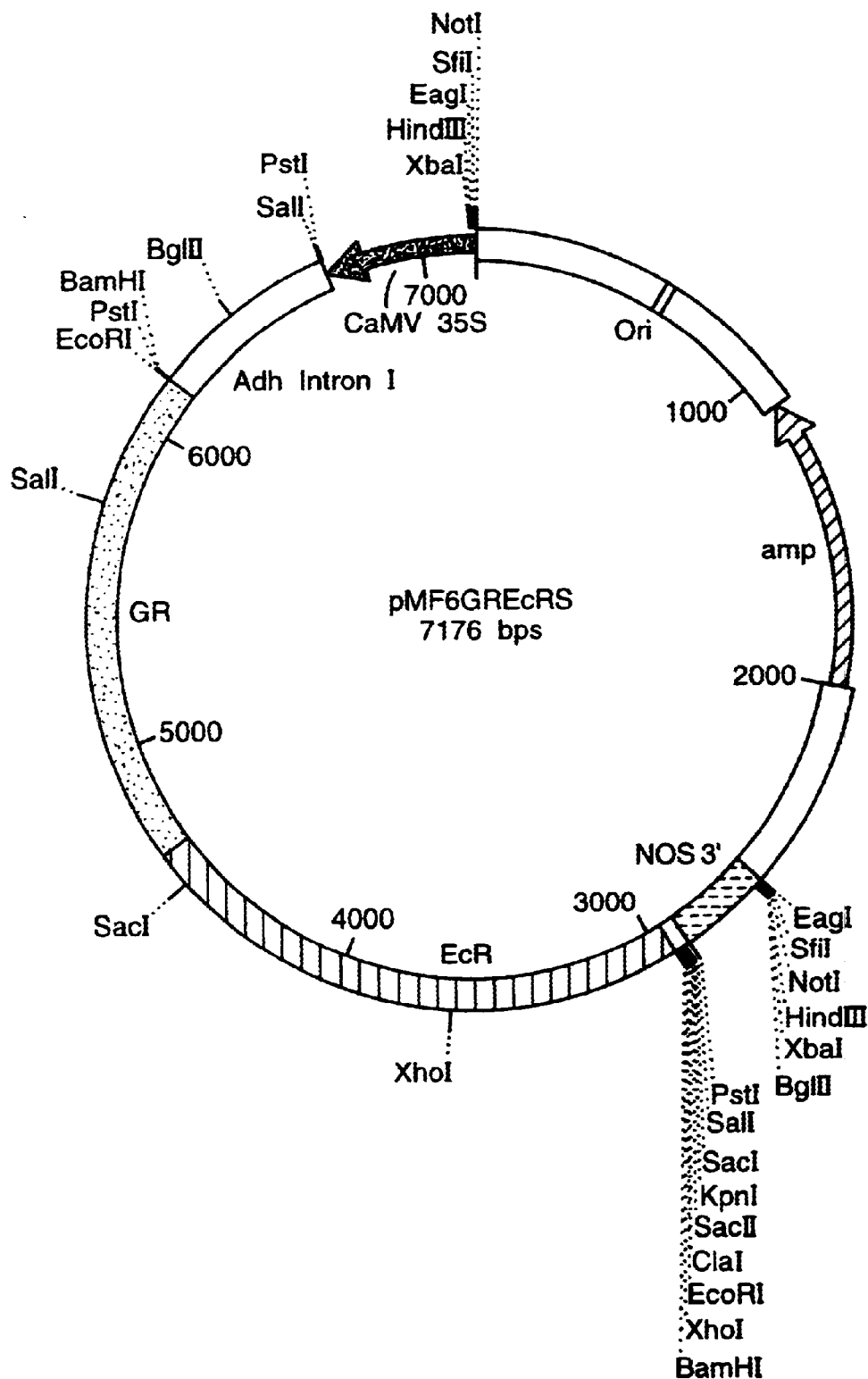
Figure 12:
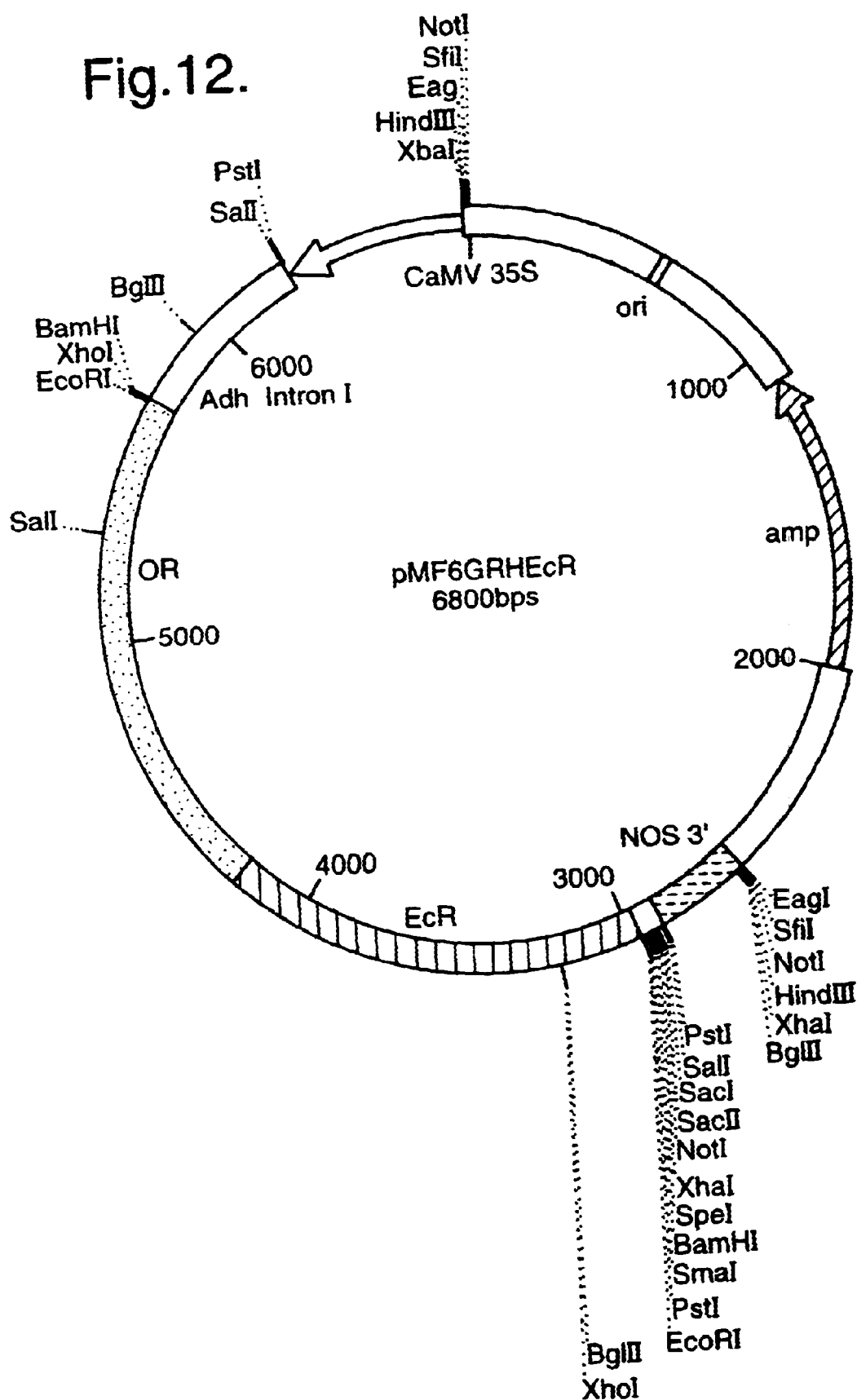
Figure 13:
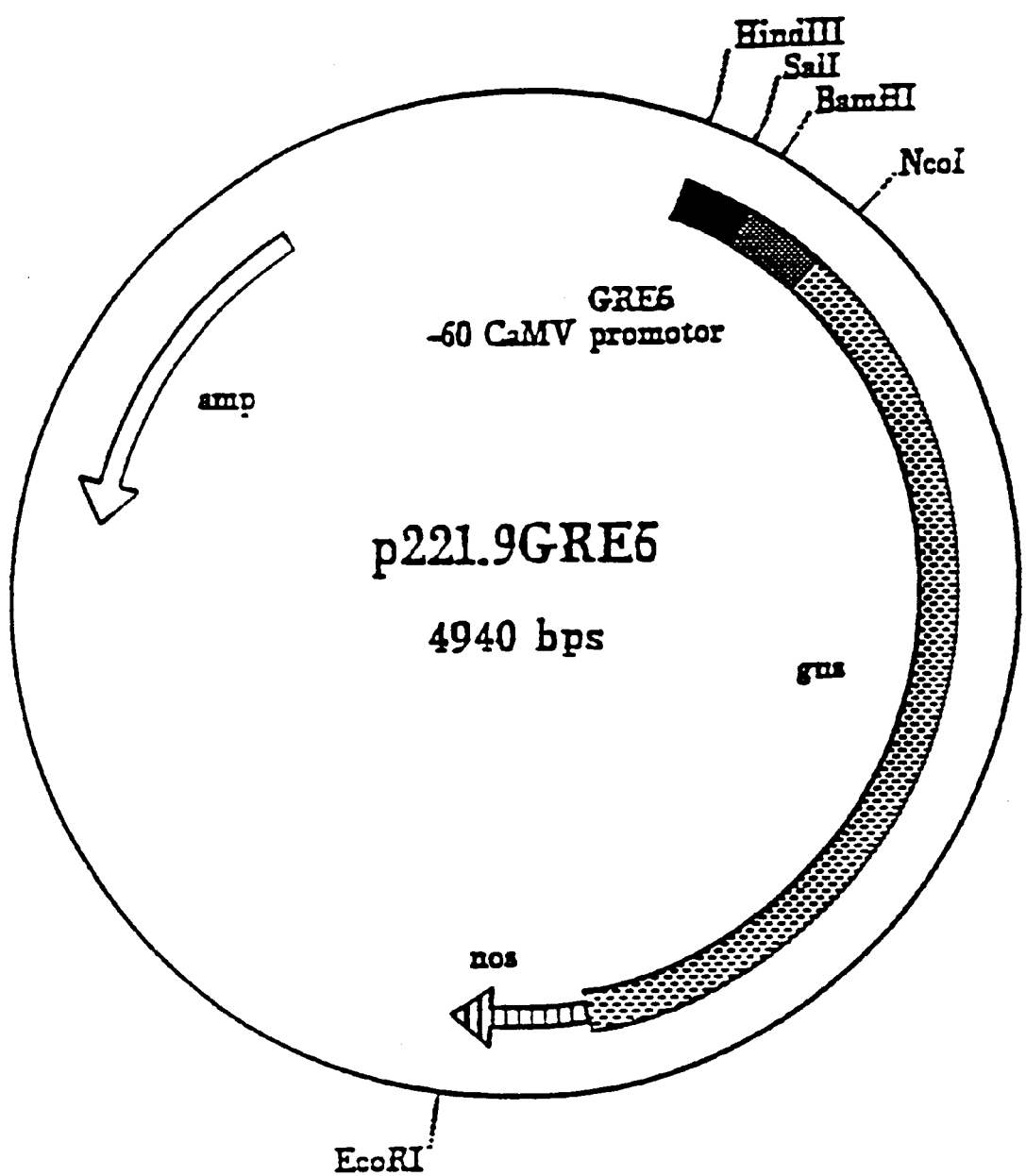
Figure 14:
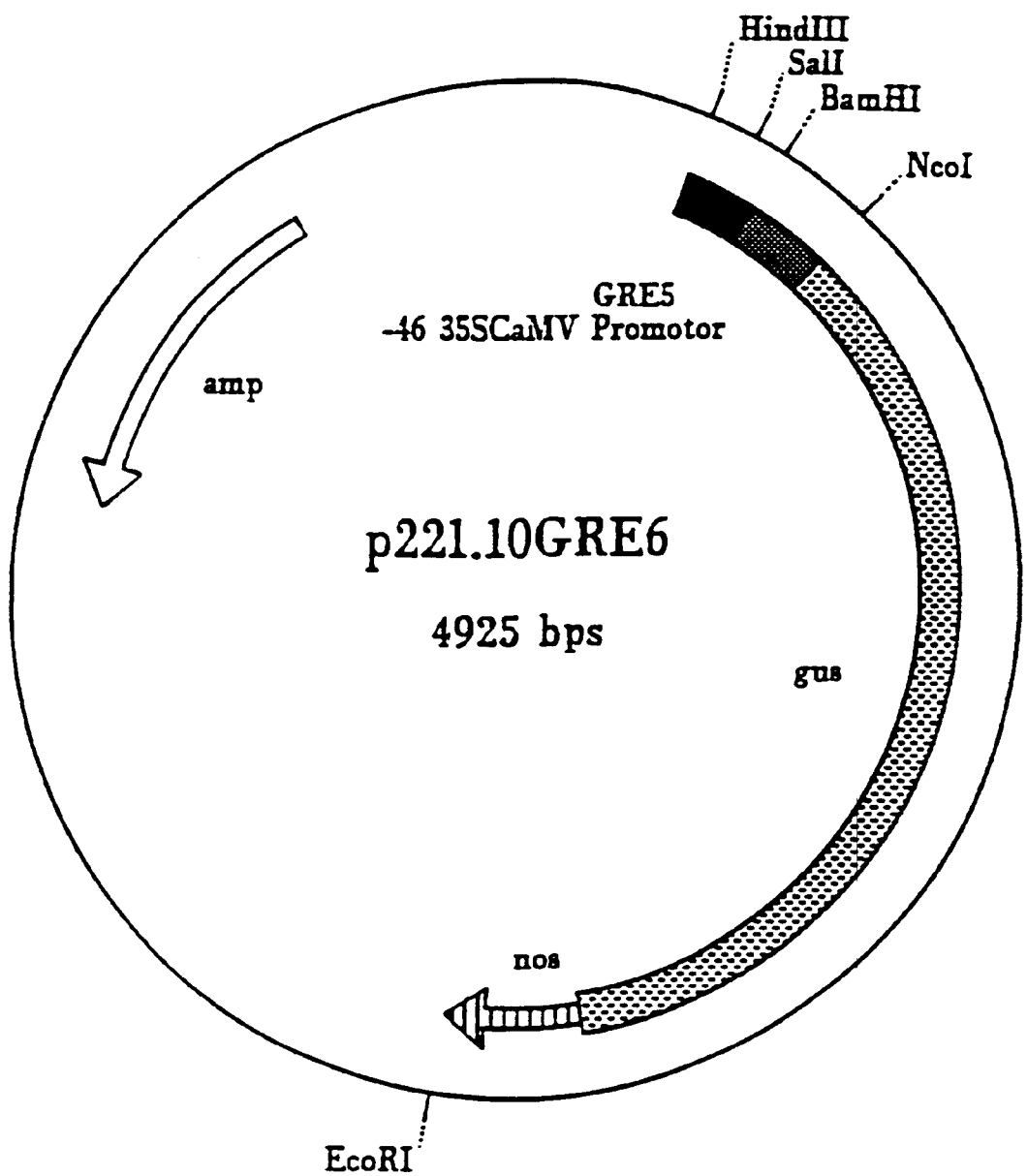
Figure 15:
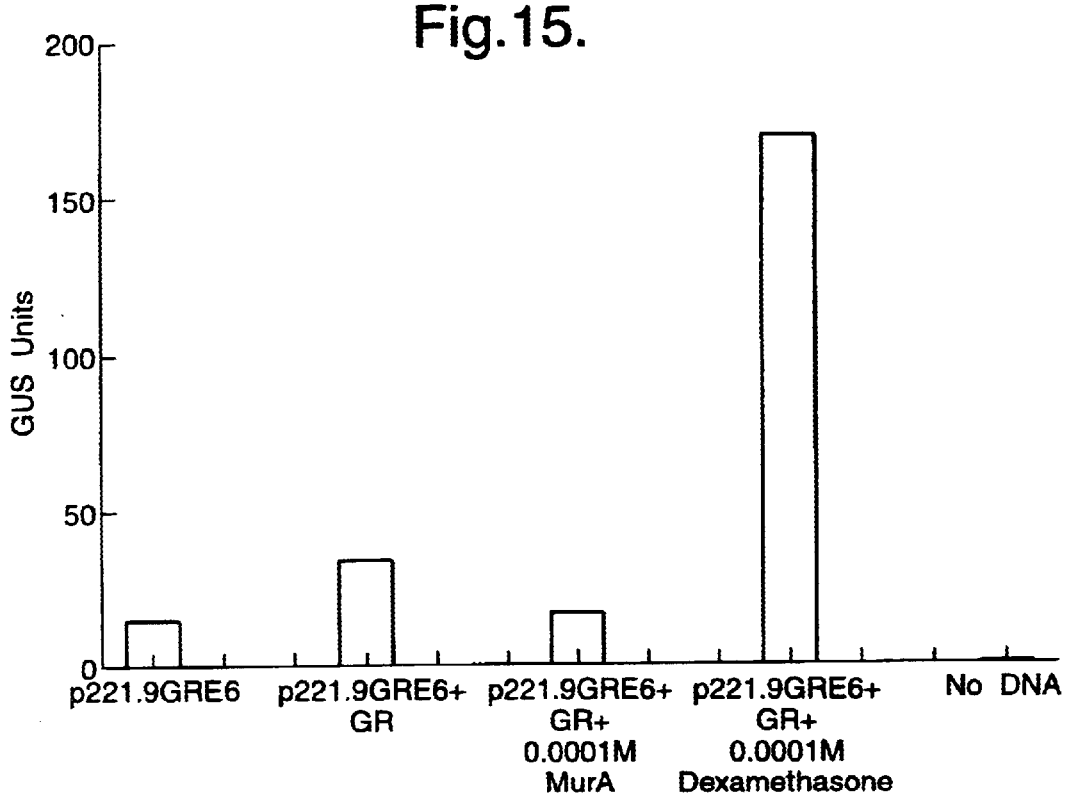
Figure 16:
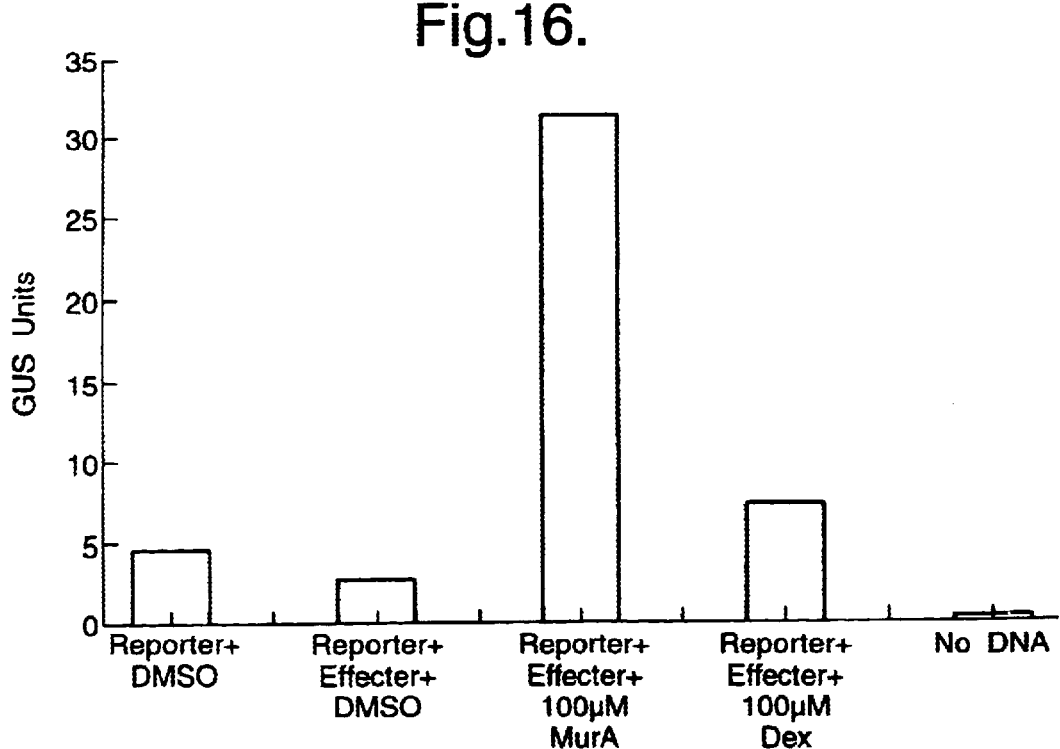
Figure 17:
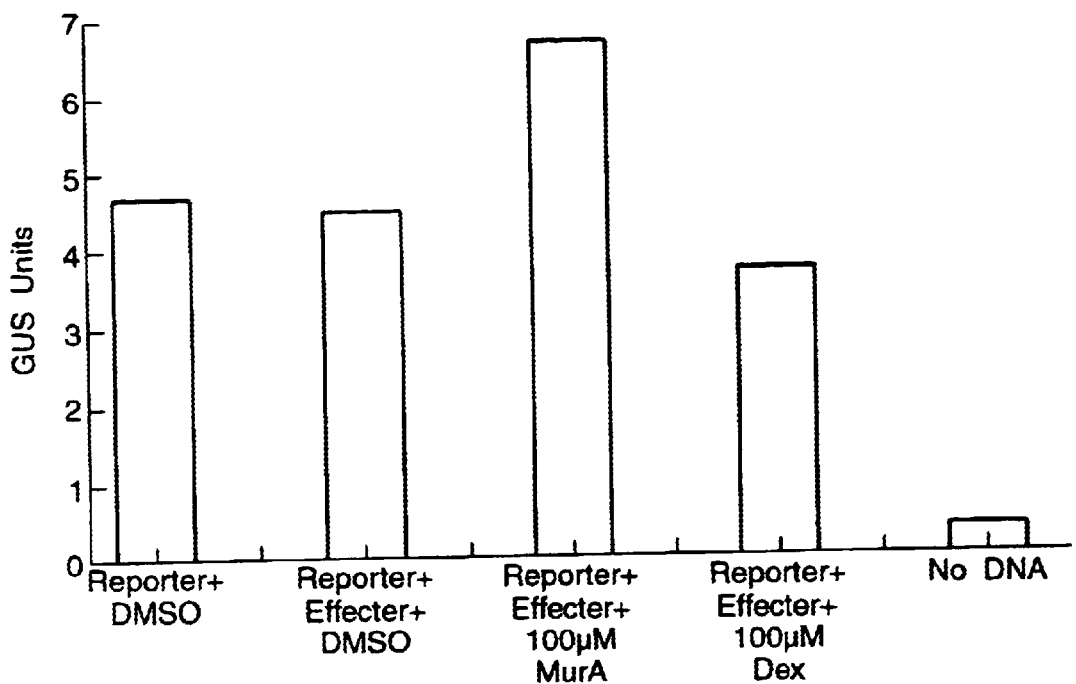
Figure 18:
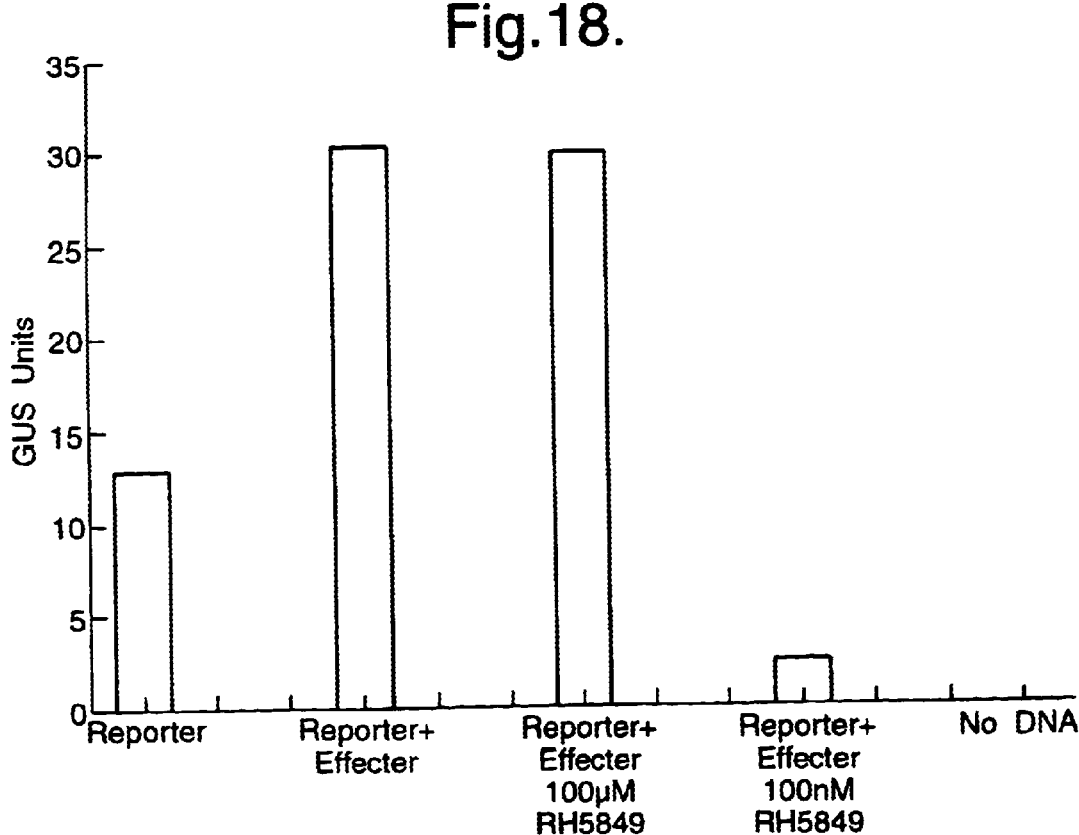
Figure 19:
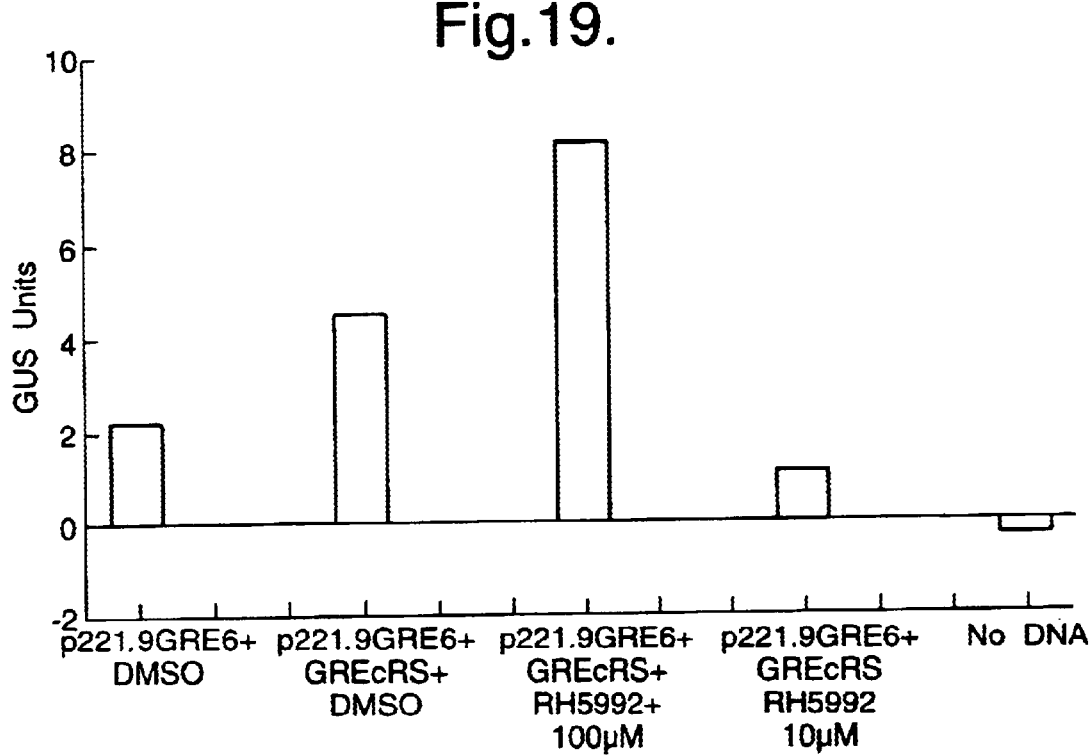
Figure 20:
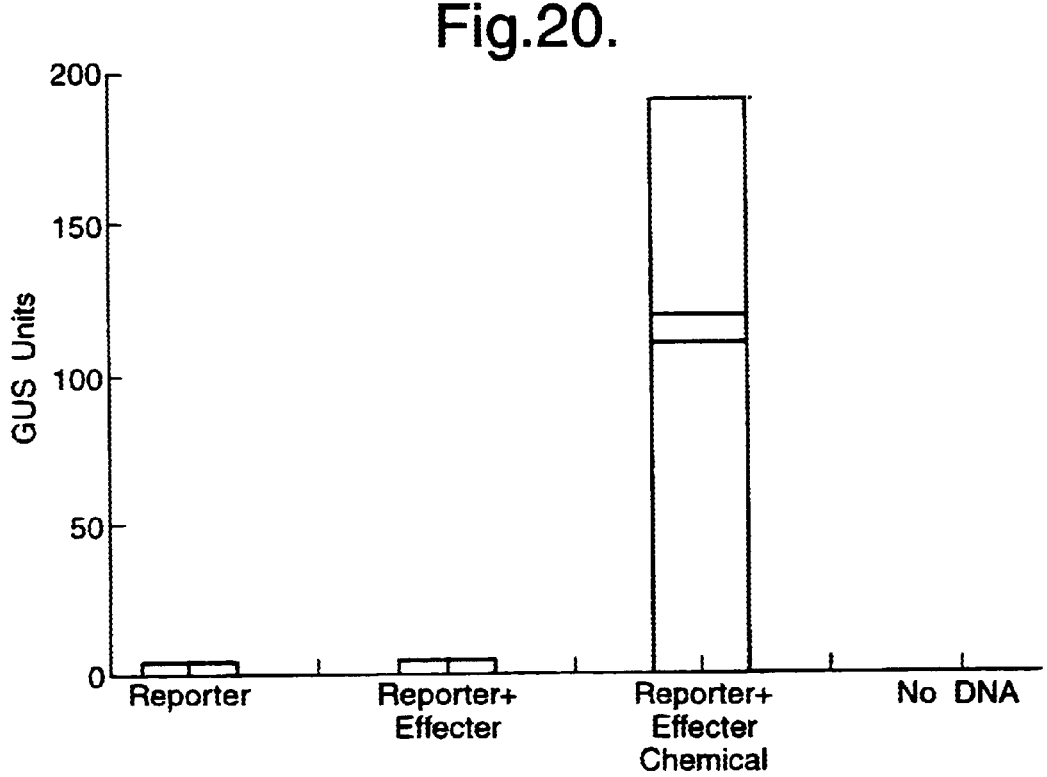
Figure 21:
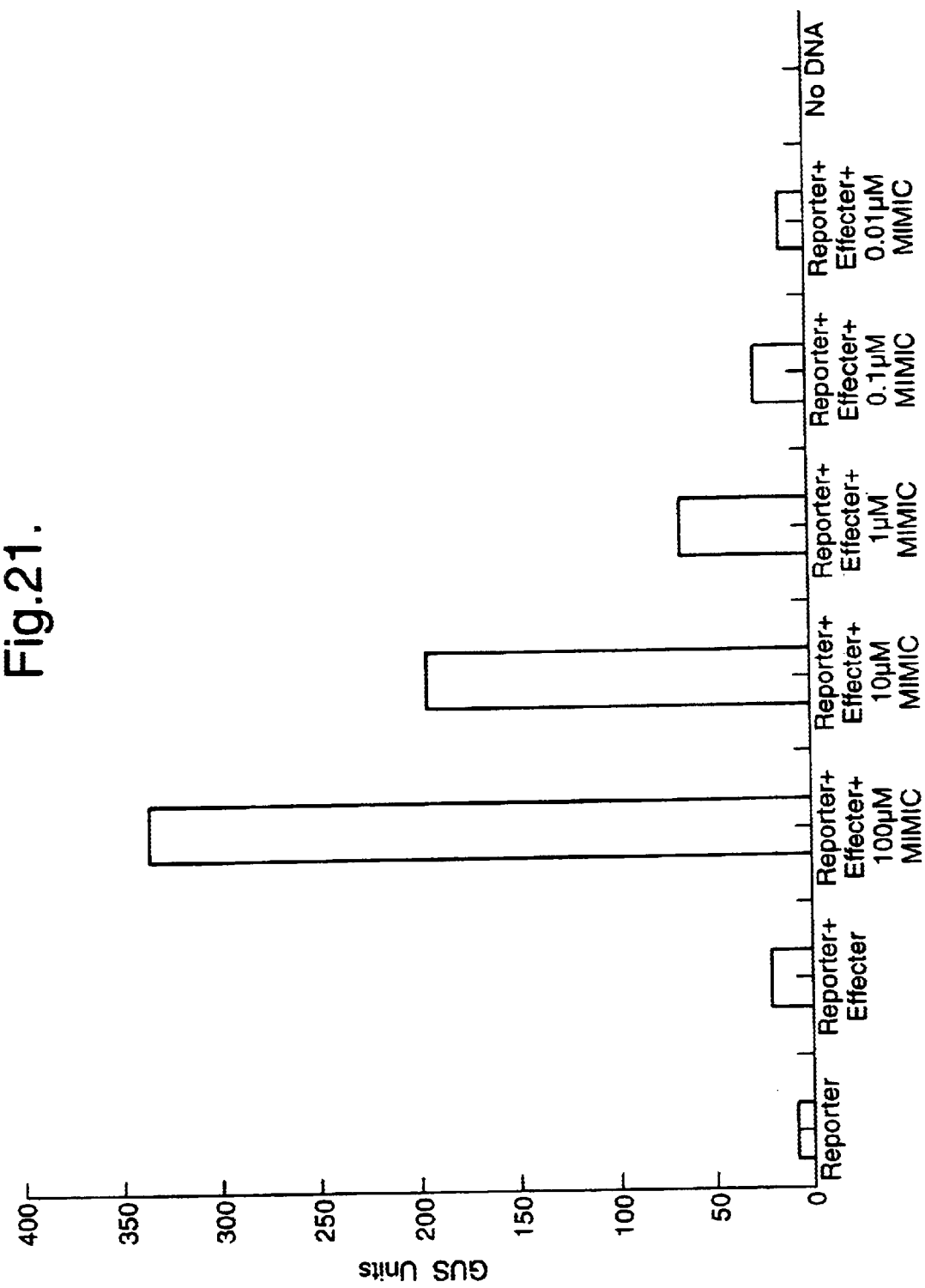
Figure 22:
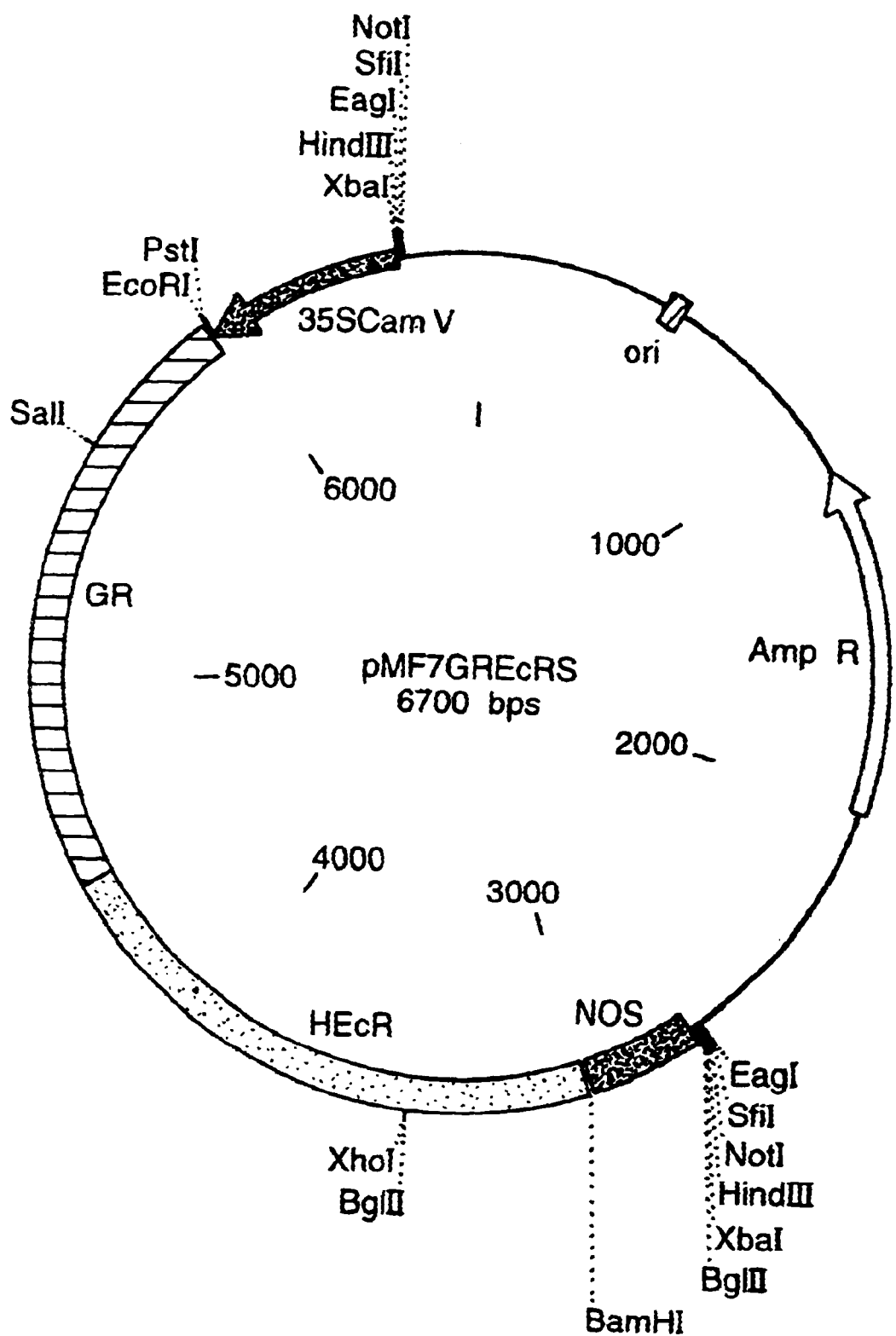
Figure 23:
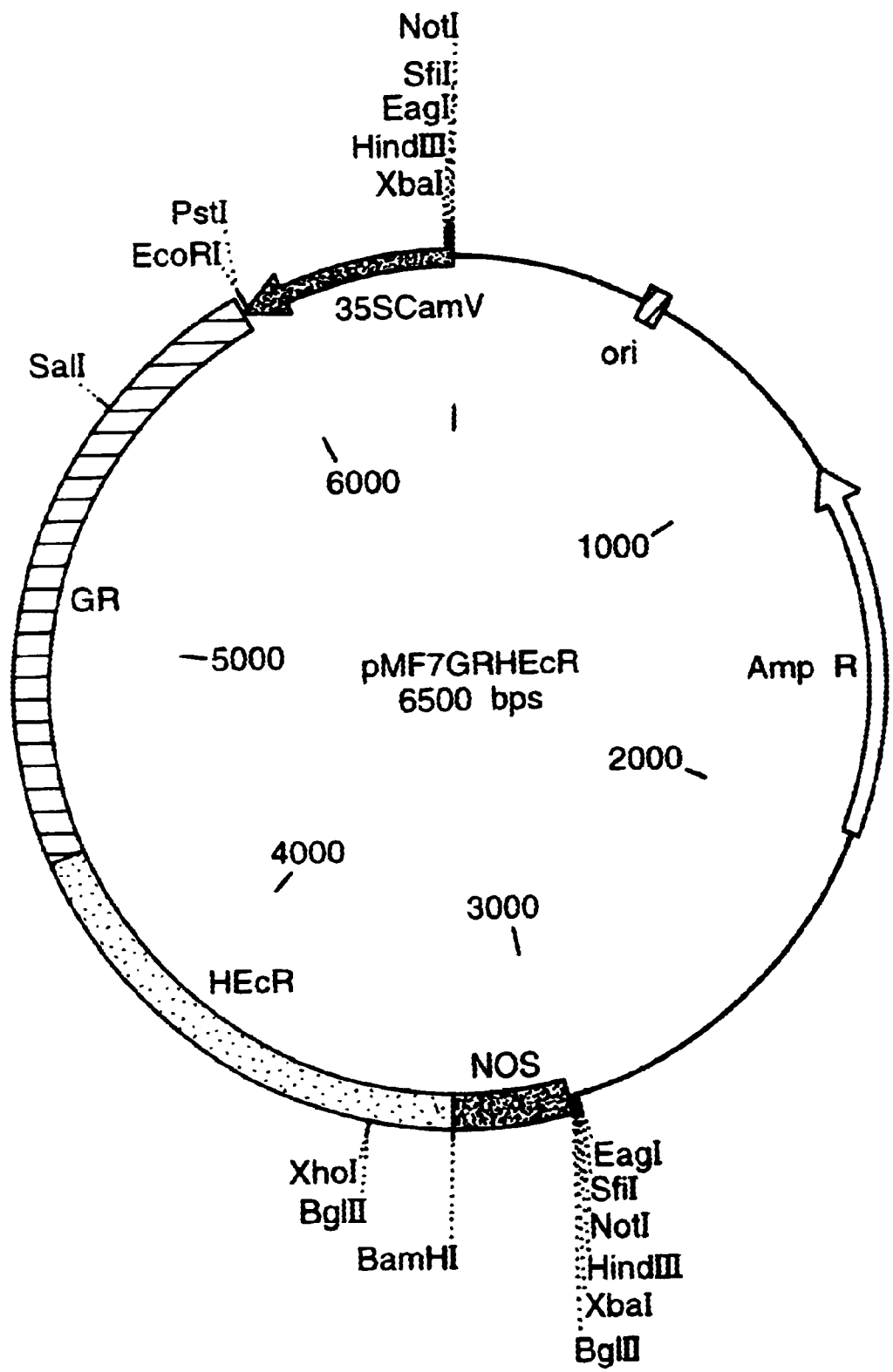
Figure 24:
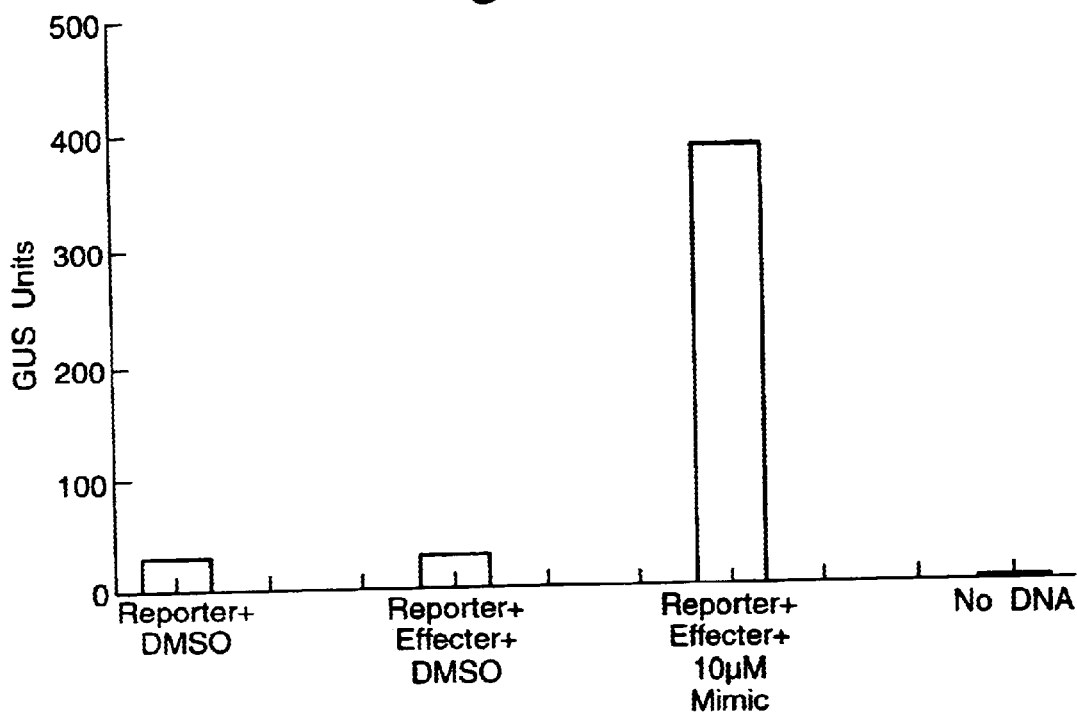
Figure 26:
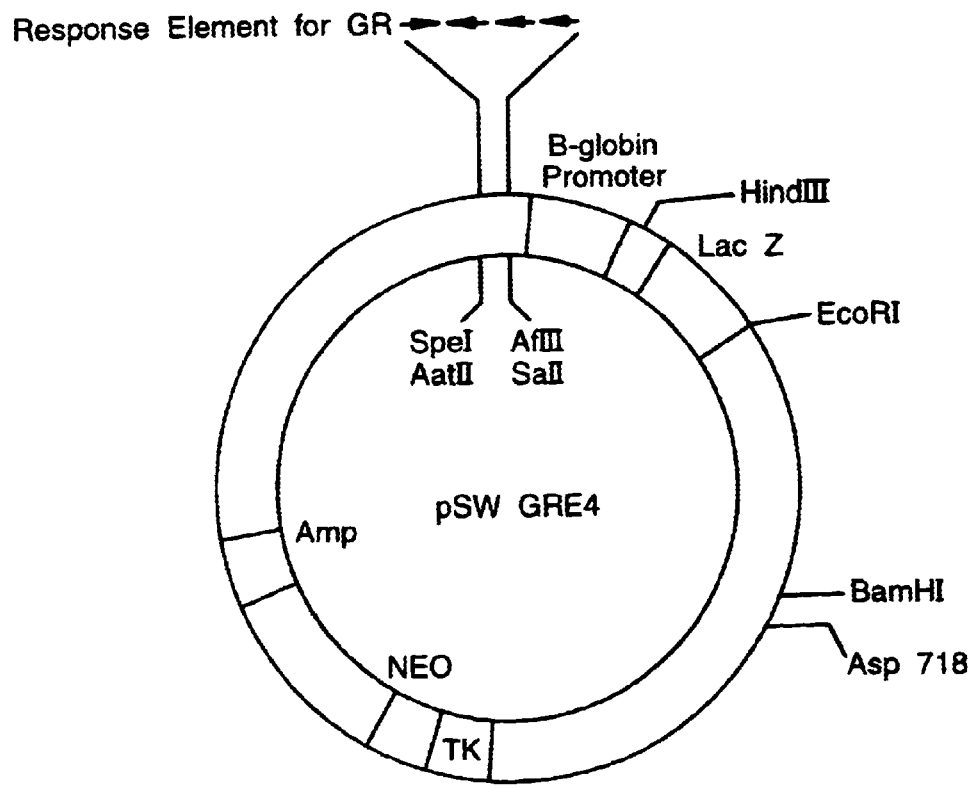
Figure 25:
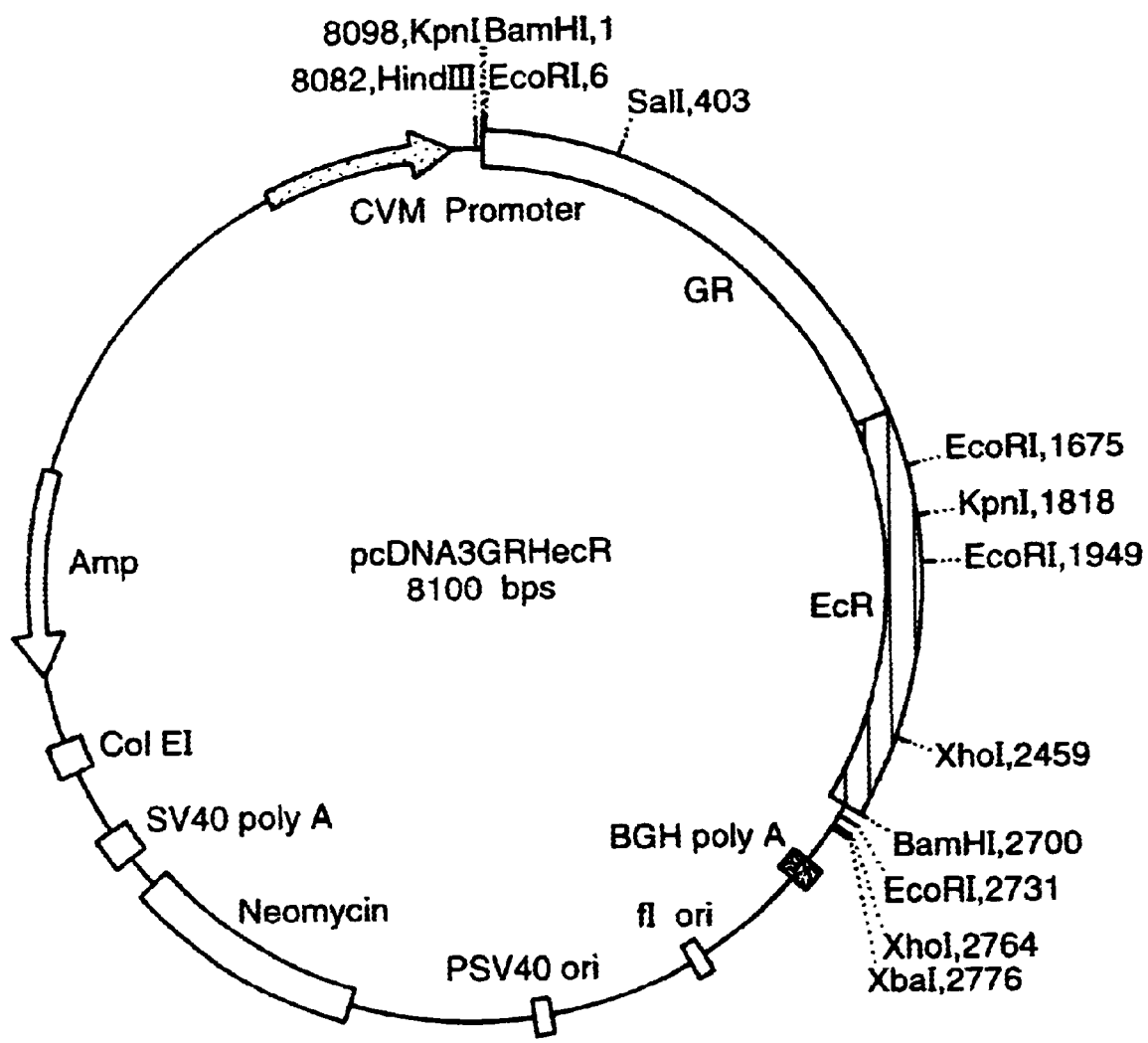
Figure 27:
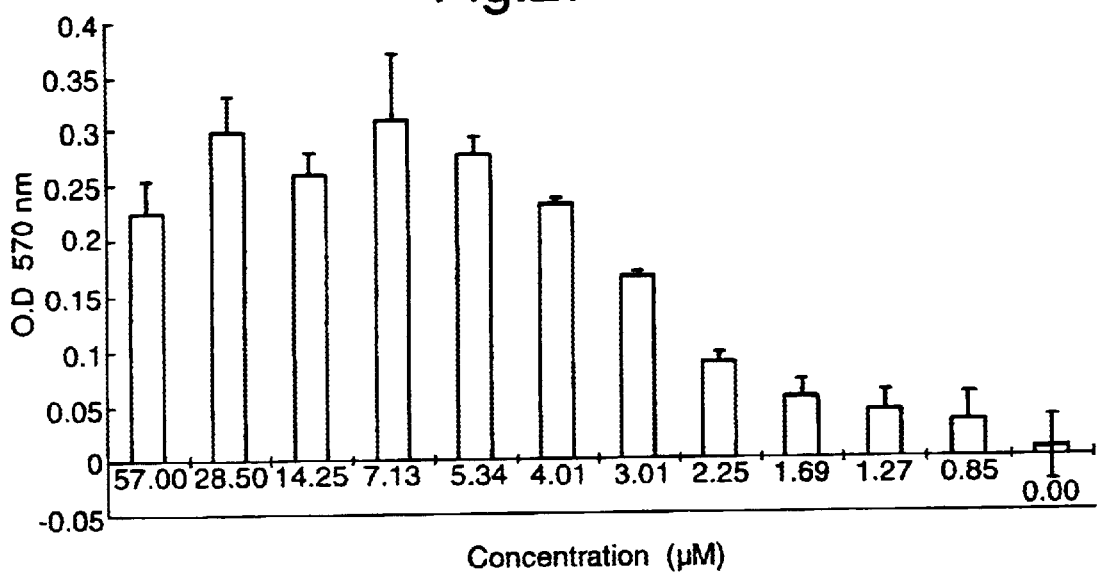
Figure 28:
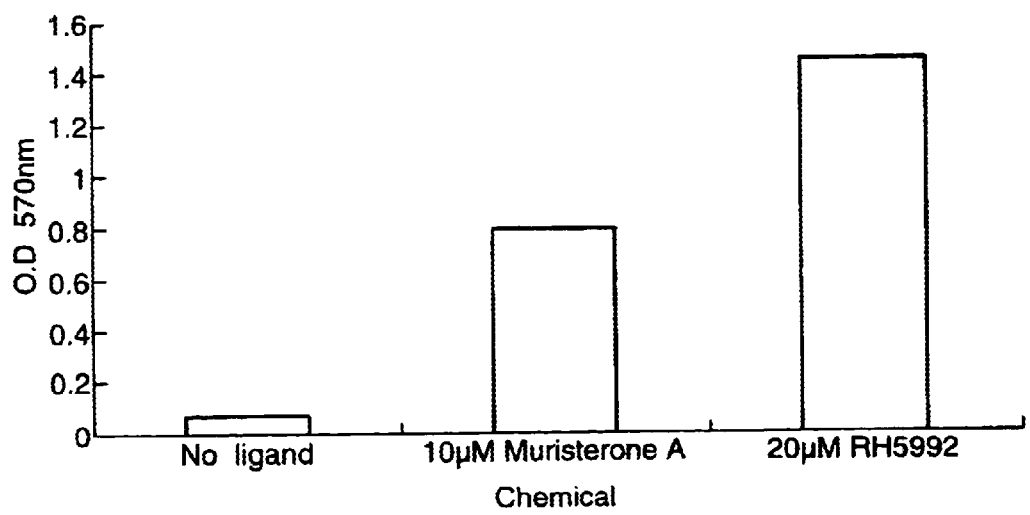
Figure 29:
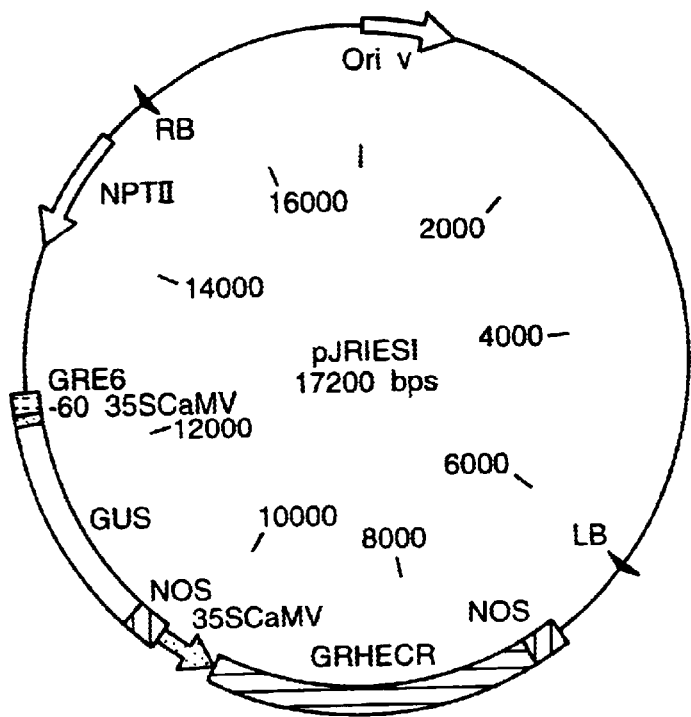
Figure 30:
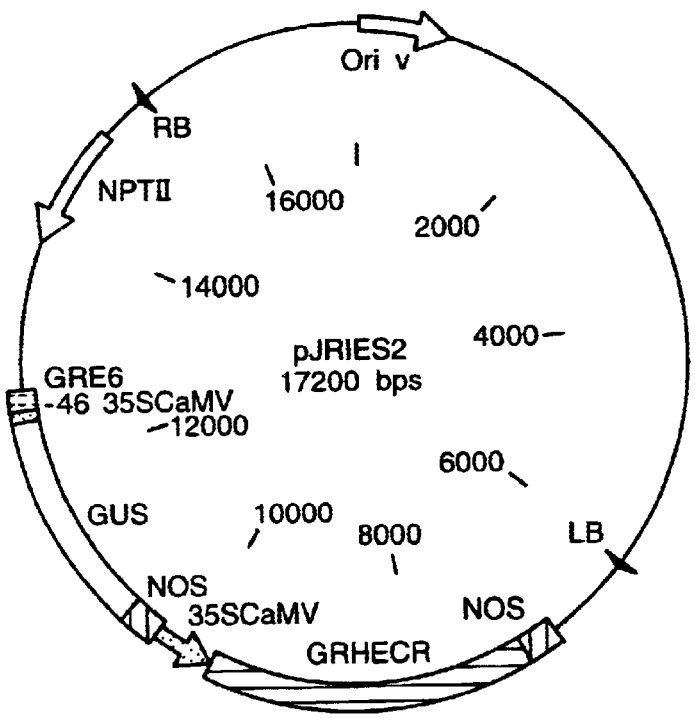
Figure 31:
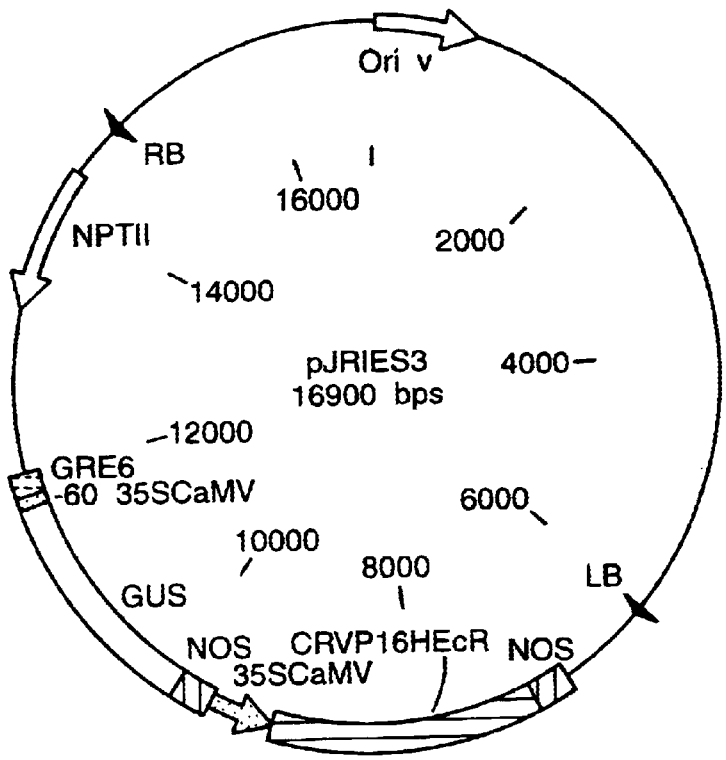
Figure 32:
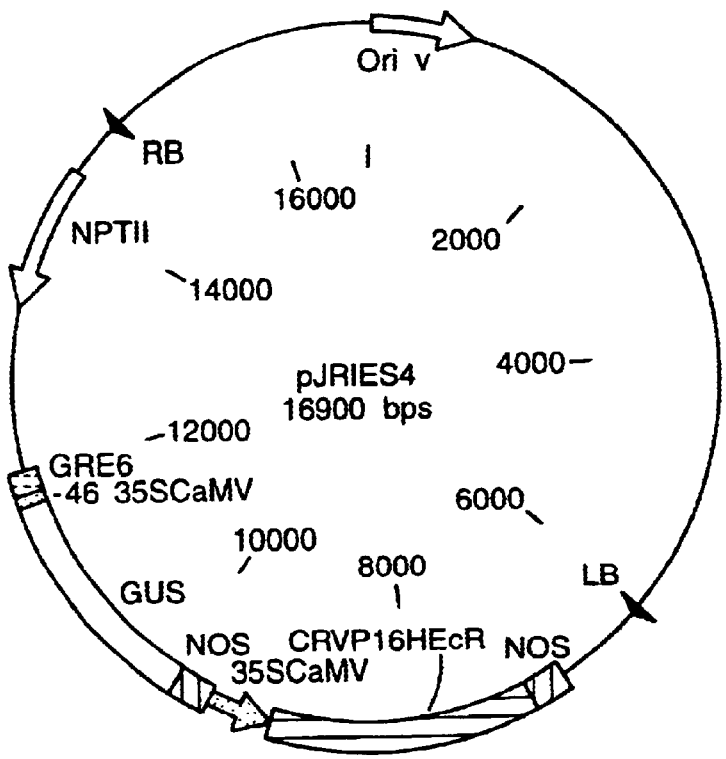
Figure 33:
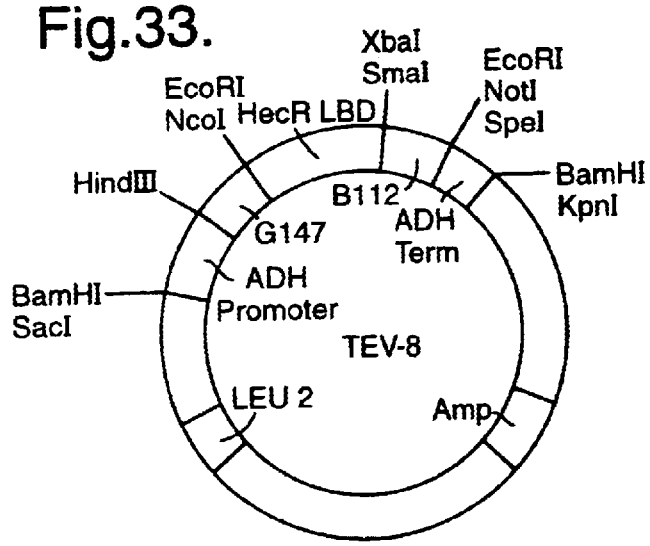
Figure 34:
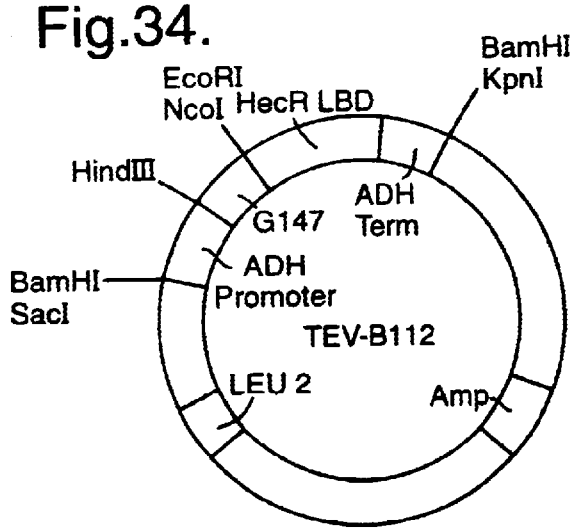
Figure 35:
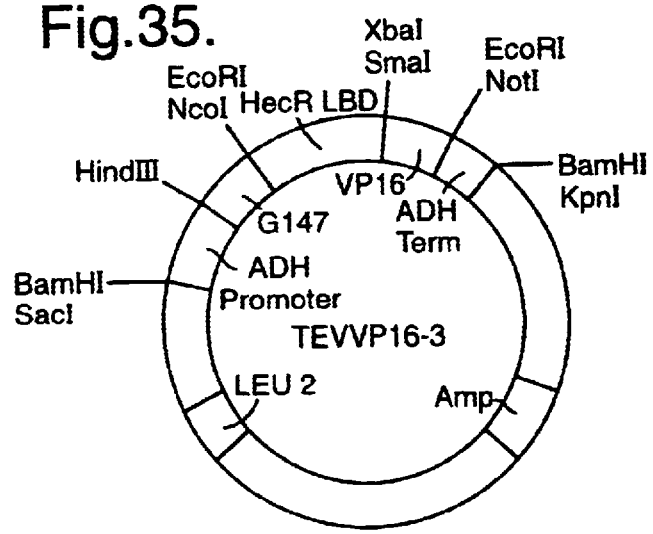
Figure 36:
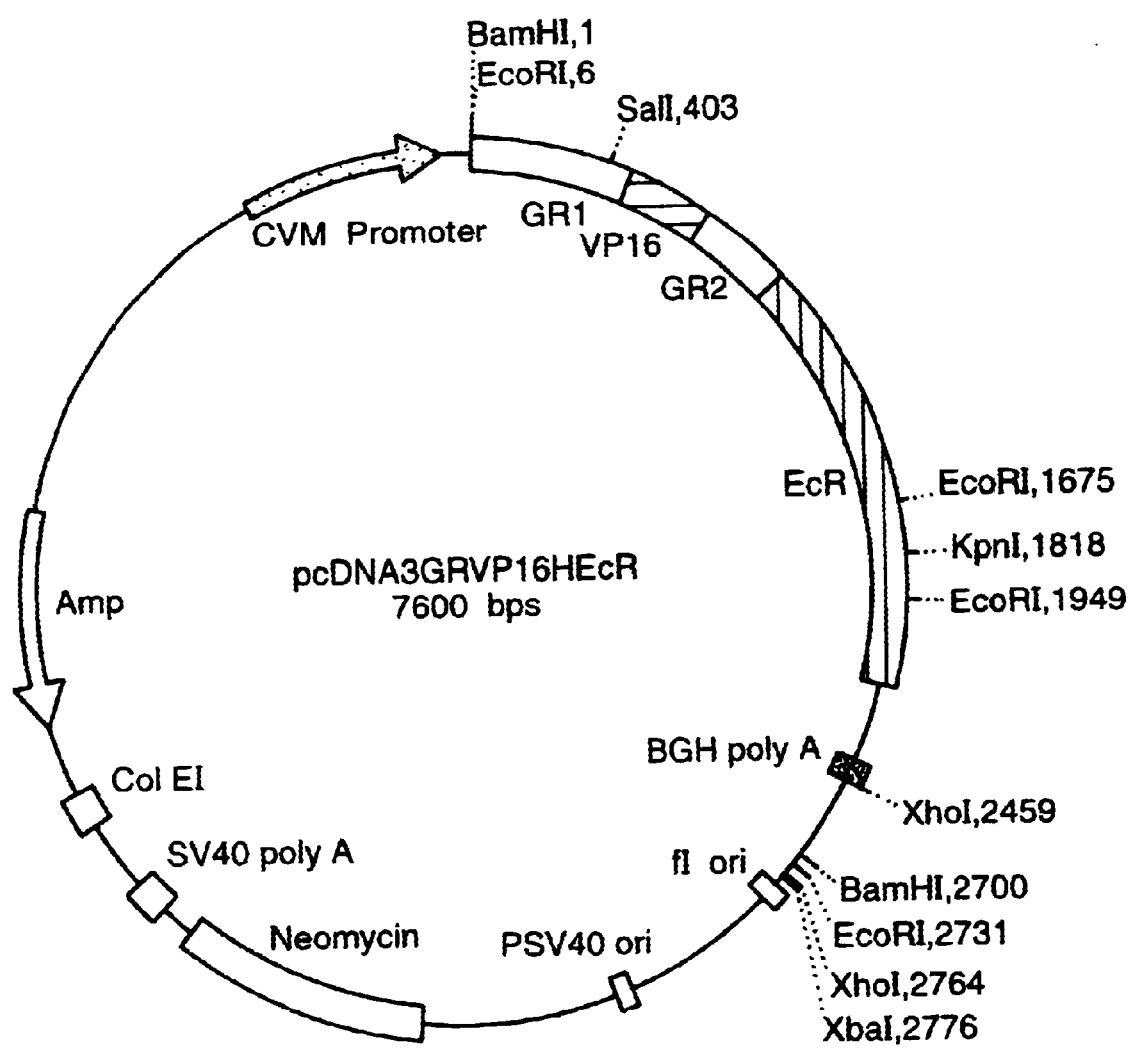
Figure 37:
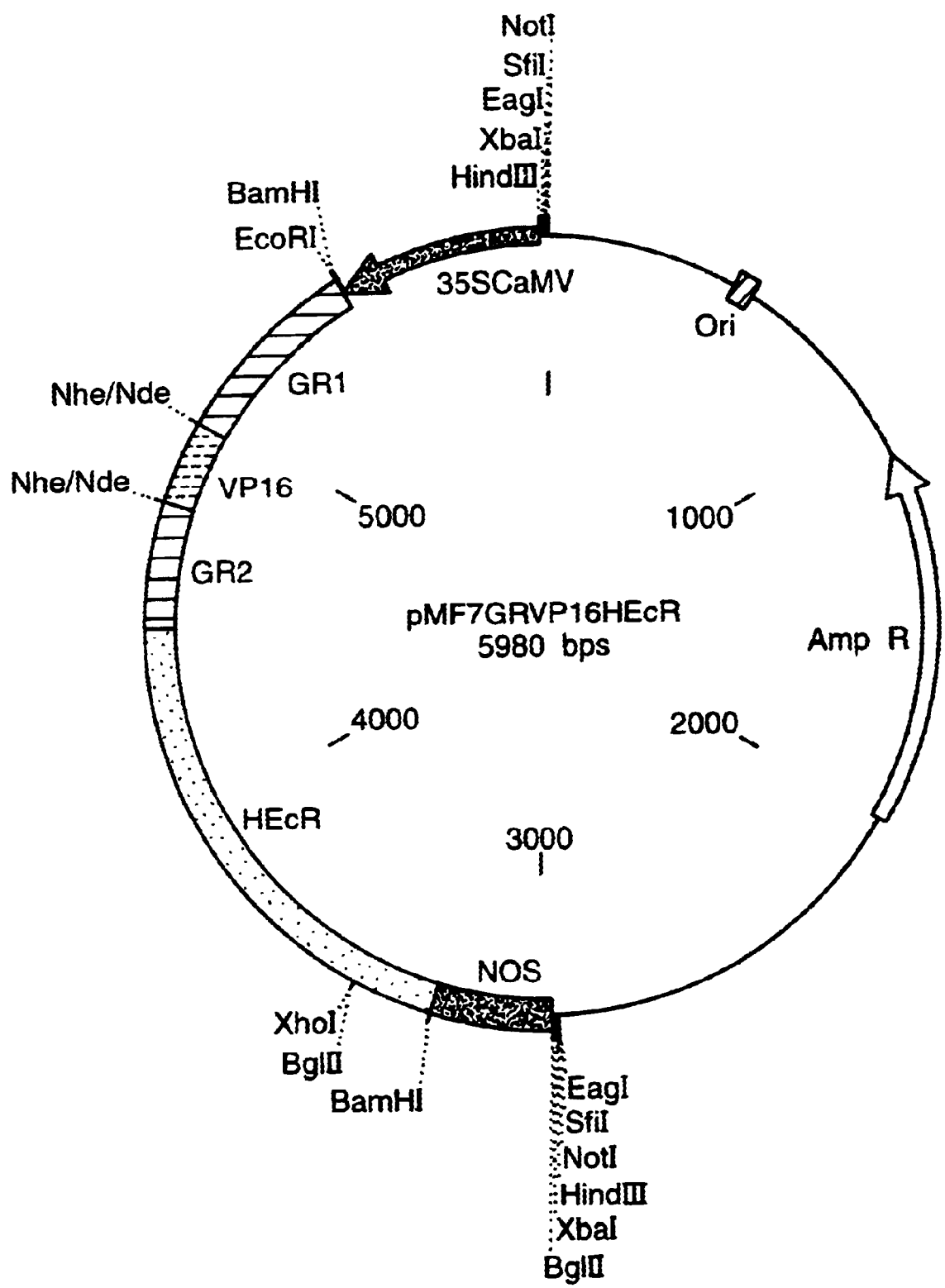
Figure 38:
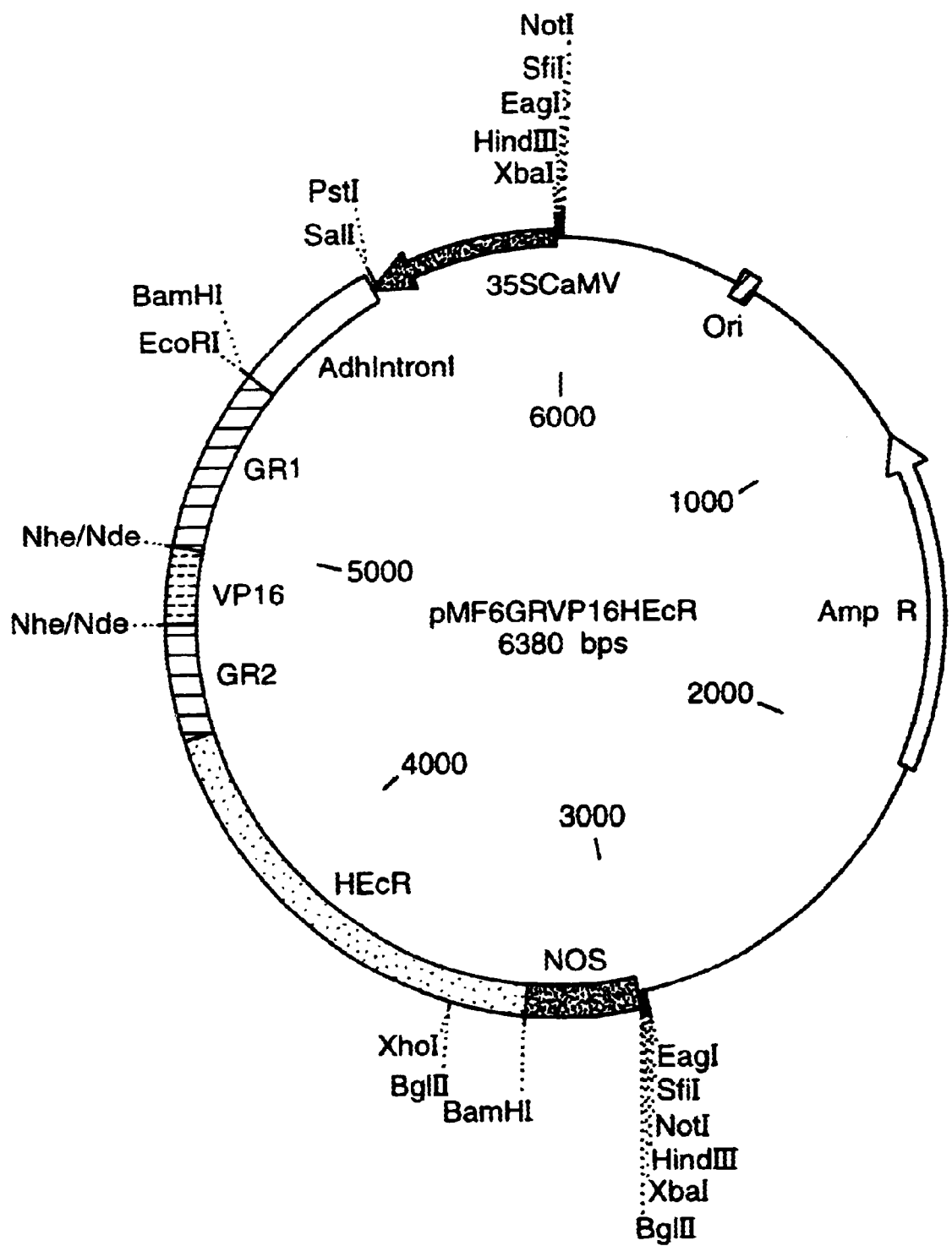
Figure 39:
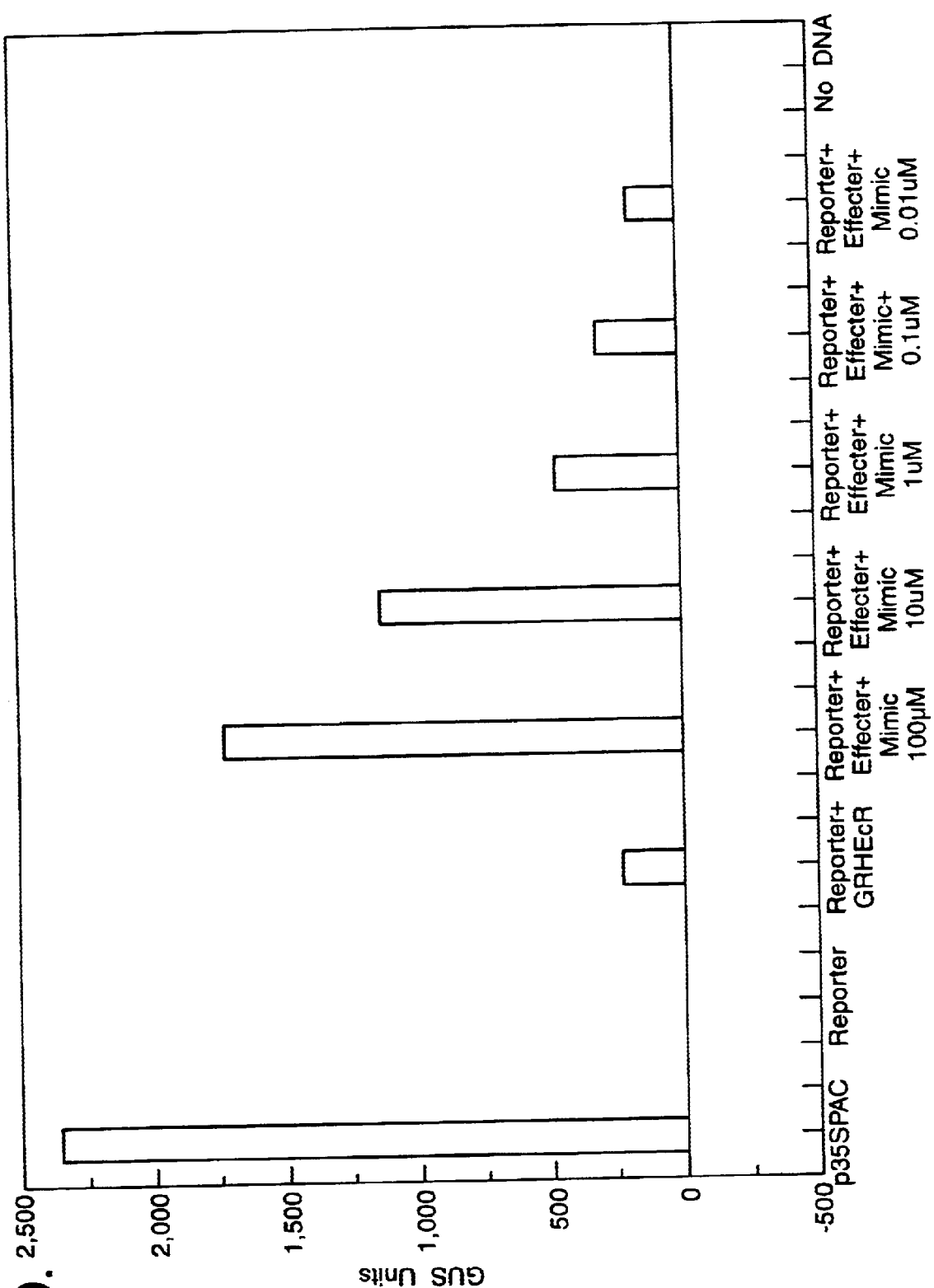
Figure 42:
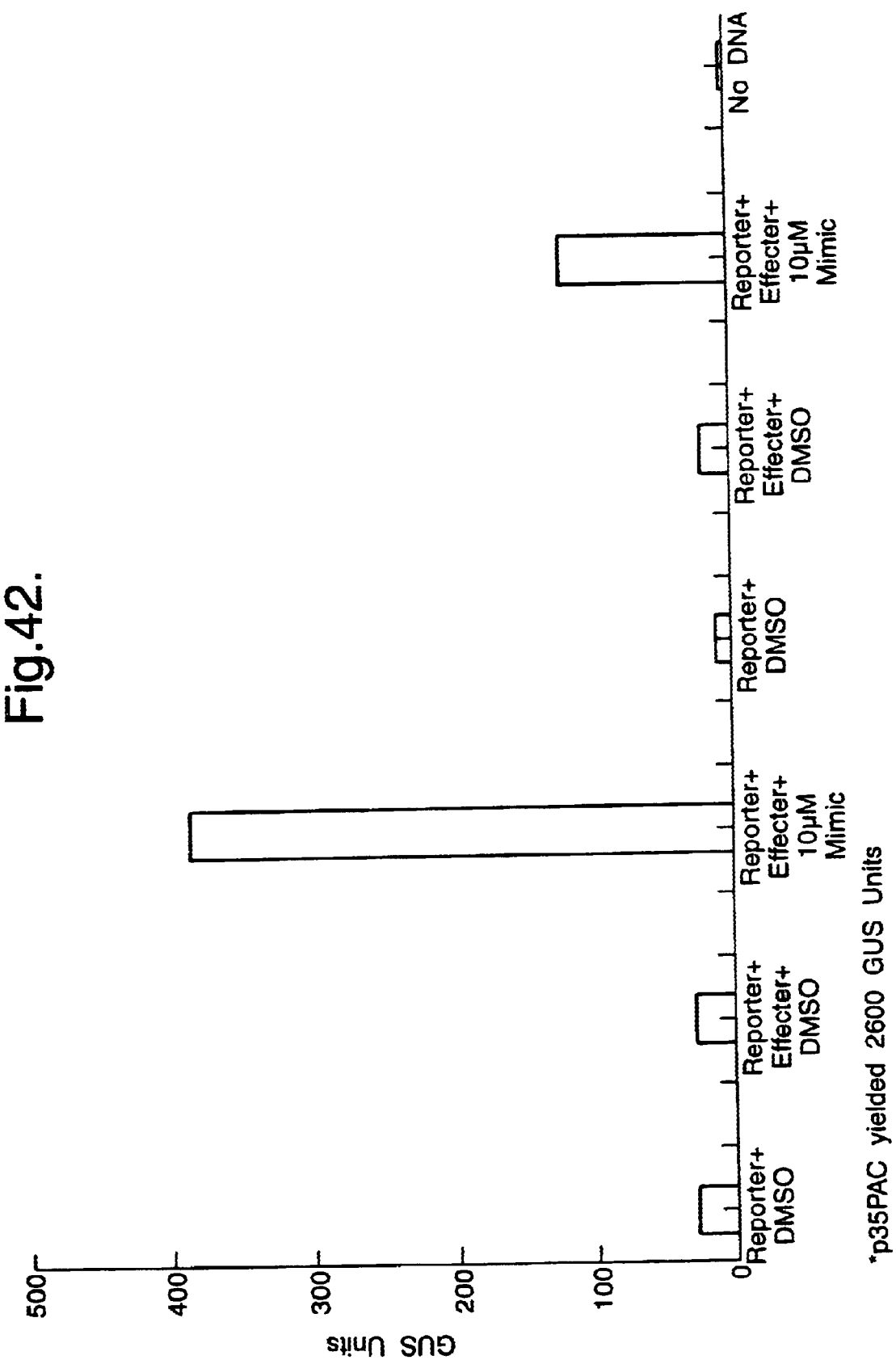

FIG. 4 presents the DNA sequence of 5'RACE products (in bold) fused to sequence of clone pSK16.1. The ORF (open reading frame; Sequence Id No:4) giving rise to the *Heliothis virescens* ecdysone receptor protein sequence (Sequence Id No:5) is shown under the corresponding DNA sequence;

FIG. 5 shows the protein sequence alignment of the ecdysone receptors DmEcR (*Drosophila melanogaster*, Sequence Id No. 8), CtEcR (*Chironomus tentans*; Sequence Id No:9), BmEcR (*Bombyx mori*; Sequence Id No:10), MsEcR (*Manduca sexta*; Sequence Id No:11), AaEcR (*Aedes aegypti*; Sequence Id No:12) and HvEcR (*Heliothis virescens*; Sequence ID No. 5). indicates conserved amino acid residue. "." indicates a conservative amino acid exchange;

FIG. 6 shows a model of an embodiment of the glucocorticoid/Heliothis ecdysone chimeric receptor useable as a gene switch;

FIG. 7 shows a plasmid map of the clone pcDNA319R. The three other mammalian expression vectors were constructed in the same way and look similar but for the size of the insert;

FIG. 8 shows a plasmid map of the reporter construct used to analyse the activity of the *Heliothis virescens* ecdysone receptor;

FIG. 9 is a graph which shows the effect of Muristerone A and RH5992 in reporter activity in HEK293 cells co-transfected with pcDNA3H3KHEcR alone (filled bars) or with αRXR (stripped bars);

FIG. 10 shows a plasmid map of the Maize expression vector containing the Glucocorticoid receptor (HG1 or pMF6HG1PAT);

FIG. 11 shows a plasmid map of the maize expression vector containing the chimeric glucocorticoid/Drosophila ecdysone receptor pMF6GREcRS;

FIG. 12 shows a plasmid map of the maize expression vector containing the chimeric glucocorticoid/Heliothis ecdysone receptor pMF6GRHEcR;

FIG. 13 shows a plasmid map of the plant reporter Plasmid containing the glucocorticoid response elements fused to the −60 S35CaMV promoter fused to GUS, p221.9GRE6;

FIG. 14 shows a plasmid map of the plant reporter plasmid containing the glucocorticoid response elements fused to the −46 S35CaMV promoter fused to GUS, p221.1OGRE6;

FIG. 15 shows a graph showing the effect of Muristerone A and Dexamethasone in Maize AXB protoplasts transformed with pMF6HG1PAT (GR) and p221.9GRE6 (reporter);

FIG. 16 shows a graph showing the effect of Muristerone A and Dexamethasone in Maize AXB protoplasts transformed with pMF6GREcRS (effector) and p221.9GRE6 (reporter);

FIG. 17 shows a graph showing the effect of Muristerone A and Dexamethasone in Maize AXB protoplasts transformed with pMF6GRHEcR (effector) and p221.9GRE6 (reporter);

FIG. 18 shows a graph showing the effect of RH5849 in Maize AXB protoplasts transformed with pMF6GREcRS (effector) and p221.9GRE6 (reporter);

FIG. 19 shows a graph showing the effect of RH5992 in Maize AXB protoplasts transformed with pMF6GREcRS (effector) and p221.9GRE6 (reporter);

FIG. 20 shows a graph showing the effect of RH5992 in Maize AXB protoplasts transformed with pMF6GRHEcR (effector) and p221.9GRE6 (reporter);

FIG. 21 shows a graph which shows the dose response effect of RH5992 in Maize AXB protoplasts transformed with pMF6GRHEcR (effector) and p221.9GRE6 (reporter);

FIG. 22 shows a plasmid map of the tobacco expression vector containing the chimeric glucocorticoid/Drosophila ecdysone receptor, pMGREcRS;

FIG. 23 shows a plasmid map of the tobacco expression vector containing the chimeric glucocorticoid/Heliothis ecdysone receptor, pMF7GRHEcR;

FIG. 24 shows a graph which shows the effect of RH5992 in Tobacco mesophyll protoplasts transformed with pMF6GRHEcR (Effector) and p221.9GRE6 (reporter);

FIG. 25 shows a plasmid map of the mammalian expression vector containing the chimeric glucocorticoid/Heliothis ecdysone receptor, pcDNA3GRHEcR;

FIG. 26 shows a plasmid map of the reporter plasmid pSWGRB4;

FIG. 27 shows a graph which shows a RH5992 dose response curve of CHO cells transfected with pcDNA3GRHEcR and pSWGRE4;

FIG. 28 shows a graph which shows the effect of Muristerone A and RH5992 on HEK293 cells co-transfected with pcDNA3GRHEcR and pSWGRE4;

FIG. 29 shows a plasmid map of the binary vector ES1;

FIG. 30 shows a plasmid map of the binary vector ES2;

FIG. 31 shows a plasmid map of the binary vector ES3;

FIG. 32 shows a plasmid map of the binary vector ES4;

FIG. 33 shows a plasmid map of the effector construct TEV-B 112 made to express the HEcR ligand binding domain in yeast;

FIG. 34 shows a plasmid map of the effector construct TEV8 made to express the HEcR ligand binding domain in yeast;

FIG. 35 shows a plasmid map of the effector construct TEVVP16-3 made to express the HEcR ligand binding domain in yeast;

FIG. 36 shows a plasmid map of the mammalian expression vector containing the chimeric glucocorticoid VP16/Heliothis ecdsysone receptor, pcDNA3GRVP16HEcR;

FIG. 37 shows a plasmid map of the maize expression vector containing the chimeric glucocorticoid VP16/Heliothis ecdsysone receptor, pMF6GRVP16HEcR;

FIG. 38 shows a plasmid map of the maize expression vector containing the chimeric glucocorticoid VP16/Heliothis ecdsysone receptor, pMF7GRVP16HEcR;

FIG. 39 shows a graph which shows the effect of RH5992 in Maize AXB protoplasts transformed with pMF6GRVP16HEcR (effector) and p221.9GRE6 (reporter);

FIG. 40 (Sequence ID No. 6) shows the DNA sequence of the hinge and ligand binding domains of the *Spodoptera exigua* ecdysone-receptor (Complimentary sequence, Sequence ID No. 63, is also shown);

FIG. 41 shows the protein sequence alignment of the Heliothis 19R (Sequence ID No. 13) and Spodoptera SEcR Taq clone hinge and ligand binding domains (Sequence ID No.7). "*" indicates conserved amino acid residue. "." indicates a conservative amino acid exchange;

FIG. 42 shows a graph which shows the effect of RH5992 on Tobacco mesophyll protoplasts transformed with pMF7GRHEcR (effector) and either p221.9GRE6 (Horizontal strips) or p221.1 OGRE6 (vertical strips).

EXAMPLE I

Cloning of the Heliothis Ecdysone Receptor

A. Probe Generation

The rational behind the generation of the probe to isolate Heliothis homologues to the steroid/thyroid receptor superfamily members was based on comparing the sequences of developmentally regulated steroid/thyroid receptor superfamily members. The sequences available showed a highly conserved motif within the DNA binding domain of the RAR and THR (thyroid) receptors. The motifs were used to design degenerate oligonucleotides for PCR amplification of sequences derived from cDNA template produced from tissue expected to express developmentally regulated steroid/thyroid receptor superfamily members (ie. larval tissues).

The sense oligonucleotide is based on the peptide sequence CEGCKGFF (Sequence Id No. 14), which at the DNA level yields an oligonucleotide with degeneracy of 32 as shown below:

ZnFA5' (Sequence Id No. 15)
  5' TGC GAG GGI TGC AAG GAI TTC TT 3'
      T A T A T The antisense oligonucleotide is based on the reverse complement nucleotide sequence derived from the peptide (Sequence Id No. 16):

CQECRLKK
  S R for which four sets of degenerate oligos were made. Namely:

ZnFA3' (Sequence Id No. 17)
  5' TTC TTI AGI CGG CAC TCT TGG CA 3'
      T A T C A ZnFB3' (Sequence Id No. 18)
  5' TTC TTI AAI CGG CAC TCT TGG CA 3'
      T A T C A ZnFC3' (Sequence Id No. 19)
  5' TTC TTI AGI CTG CAC TCT TGG CA 3'
      T A T C A ZnFD3' (Sequence Id No. 20)
  5' TTC TTI AAI CTG CAC TCT TGG CA 3'
      T A T C A The PCR amplification was carried out using a randomly primed cDNA library made from mRNA isolated from 4th and 5th instar *Heliothis virescens* larvae. The amplification was performed using $10^8$ pfus (plaque forming units) in 50 mM KCl. 20 mM Tris HCl pH 8.4, 15 mM MgCl2, 200 mM dNTPs (an equimolar mixture of dCTP, dATP, dGTP and dTTP), 100 ng of ZnFA5' and ZnF3' mixture. The conditions used in the reaction followed the hot start protocol whereby the reaction mixture was heated to 94° C. for 5 minutes after which 1 U of Taq polymerase was added and the reaction allowed to continue for 35 cycles of 93° C. for 50 seconds, 40° C. for 1 minute and 73° C. for 1 minute 30 seconds. The PCR products were fractionated on a 2%(w/v) agarose gel and the fragment migrating between 100 and 200 bp markers was isolated and subcloned into the vector pCRII (Invitrogen). The sequence of the insert was determined using Sequenase (USB).

The resulting sequence was translated and a database search carried out. The search recovered sequences matching to the DNA binding domain of the Drosophila ecdysone receptor, retinoic acid receptor and the thyroid receptor. Thus, the sequence of the insert in this plasmid, designated pCRIIZnf, is a Heliothis ecdysone cognate sequence (FIG. 1) and was used to screen a cDNA library in other to isolate the complete open reading frame.

B. Library Screening

The randomly primed cDNA 4th/5th Instar *Heliothis virescens* library was plated and replicate filter made from the plates. The number of plaques plated was 500,000. The insert fragment of pCRIIZnf was reamplified and 50 ng were end labelled using T4 Polynucleotide Kinase (as described in Sambrook et al 1990).

The filter were prehybridised using 0.25%(w/v) Marvel, 5×SSPE and 0.1%(w/v) SDS at 42° C. for 4 hours. The solution in the filters was ten replaced with fresh solution and the denatured probe added. The hybridisation was carried out overnight at 42° C. after which the filter were washed in 6×SSC +0.1%(w/v) SDS at 42° C. followed by another wash at 55° C. The filter were exposed to X-ray film (Kodak) for 48 hours before processing.

The developed film indicated the presence of one strong positive signal which was plaque purified and further characterised. The lambda ZAP II phage was in vivo excised (see Stratagene Manual) and the sequence determined of the resulting plasmid DNA. The clone known as pSK19R (or 19R) contained a 1.933 kb cDNA fragment with an open reading frame of 467 amino acids (FIG. 2). pSK19R was deposited with the NCIMB on Jun. 20, 1995 and has been accorded the deposit No NCIMB 40743.

Further analysis of pSK19R revealed that a 340 bp EcoRI fragment mapping at the 5' end of pSK19R has strong and significant similarities to a Drosophila cDNA encoding glyceraldehyde-3-phosphate dehydrogenase. In order to isolate the correct 5'end sequence belonging to. Heliothis, the random primed library was re-screened using a probe containing the 5'end of the pSK19R belonging to Heliothis ecdysone receptor. The probe was made by PCR using the sense oligonucleotide:

HecRH3C (Sequence Id No. 21)
5' aattaagcttccaccatgccgttaccaatgccaccgaca 3'
and antisense oligonucleotide:
HecrNdel (Sequence Id No. 22)
5' cttcaaccgacactcctgac 3'.

The PCR was carried out as described by Hirst et al., 1992) where the amount of radioisotope used in the labelling was 50 uCi of a $^{32}$P-dCTP and the PCR was cycled for 1 minute at 94° C., 1minute at 60° C. and 1 minute at 72° C. for 19 cycles. The resulting 353 bp radio labelled DNA fragment was denatured and added to prehybridised filters as described for the isolation of pSK19R. The library filters were made from 15 plates each containing 50000 pfus. The library filters were hybridised at 65° C. and washed in 3×SSPE+0.1%SDS at 65° C. twice for 30 minutes each. The filters were further washed with 1×SSPE+0.1%SDS for 30 minutes and exposed to X-ray film (Kodak) overnight. The film was developed and 16 putative positive plaques were picked. The plaques were re-plated and hybridised under the exact same conditions as the primary screen resulting in only one strong positive. The strong positive was consistently recognised by the probe and was plaque purified and in vivo excised. The resulting plasmid pSK16.1 was sequenced (Sequence Id No. 3) which revealed that the 5' end of the clone extended by 205 bp and at the 3' end by 653 bp and resulting in a DNA insert of 2.5 kb. Conceptual translation of the 205 bp yielded 73 amino acids with high similarity to the Drosophila, Aedes aegypti, Manduca and Bombyx sequences of the ecdysone receptor B1 isoform. However, the whole of the 5' end sequence is not complete since a Methionine start site was not found with a stop codon in frame 5' of the methionine. In order to isolate the remainder of the 5' end coding sequences a 5'RACE protocol (Rapid Amplification of cDNA Ends) was carried out using the BRL-GIBCO 5'RACE Kit. Two types of cDNA were synthesised where the first one used a specific oligonucleotide:

16PCR2A (Sequence Id No.23)
5' cagctccaggccgccgatctcg 3'
and the second type used random hexamers (oligonucleotide containing 6 random nucleotides). Each cDNA was PCR amplified using an anchor primer from BRL-GIBCO (Sequence Id No. 24):

5' cuacuacuacuaggccacgcgtcgactagtacgggiigggiigggiig 3'
and 16PCR2A and cycled for 1 minute at 94° C., 1 minute at 60° C. and 1 minute at 72° C. for 35 cycles. The reaction conditions were 20 mM Tris-HCl (pH8.4), 50 mM KCl, 1.5 mM MgCl$_2$, 400 nM of each anchor and 16PCR2A primers, 200 mM dNTPs (dATP,dCTP,dGTP and dTTP) and 0.02 U/ml Taq DNA polymerase. Dilutions of 1:50 of the first PCR reactions were made and 1 ml was use in a second PCR with oligonucleotides Universal Anchor Primer (UAP; Sequence Id No. 25):

5' caucaucaucauggccacgcgtcgactagtac 3'
and 16RACE2 (Sequence Id No.26):

5' acgtcacctcagacgagctctccattc 3'.

The conditions and cycling were the same as those followed for the first PCR. Samples of each PCR were run and a Southern blot carried out which was probed with a 5' specific primer:

16PCR1 (Sequence Id No. 27)
5' cgctggtataacaacggaccattc 3'.

This primer is specific for the 5' most sequence of pSK16.1 and was hybridised at 55° C. using the standard hybridisation buffer. The filter was washed at 55° C. 3 times in 3×SSPE +0.1%SDS and exposed to X-ray film for up to 6 hours. The developed film revealed bands recognised by the oligonucleotide migrating at 100bp and 500bp (relative to the markers). A sample of the PCR reaction (4 in total) was cloned into the pCRII vector in the TA cloning kit (Invitrogen). Analysis of 15 clones from 4 independent PCRs yielded sequence upsteam of pSK16.1 (FIG. 4).

Translation of the ORF results in a 575 amino acid protein with high similarity in the DNA and ligand binding domains when compared to the ecdysone receptor sequences of Drosophila, Aedes aegypti, Chironomus tentans, Manduca sexta and Bombyx mori (FIG. 5). Interestingly, the N-terminal end of the Heliothis sequence has an in frame methinonine start which is 20 amino acids longer that that reported for Drosophila, Aedes aegypti and Manduca sexta. However, the extended N-terminal end in the Heliothis EcR does not have similarity to that of Bombyx mori. Finally, the C-terminal end of the different B1 isoform ecdysone receptor sequences diverge and do not have significant similarity.

C. Northern Blot Analysis

The sequence identified by screening the library is expected to be expressed in tissues undergoing developmental changes, thus mRNA from different developmental stages of H. virescens were was isolated and a northen blot produced. The mRNAs were isolated from eggs, 1st, 2nd, 3rd, 4th and 5th instar larvae, pupae and adults. The northern blot was hybridised with a NdeI/XhoI DNA fragment from pSK19R encompassing the 3'end of the DNA binding domain through to the end of the ligand binding domain. The hybridisation was carried out in 1%(w/v)Marvel, 5×SSPE, 0.1%(w/v) SDS at 65° C. for 18 to 24 hours. The filters were washed in 3×SSPE +0.1%(w/v) SDS and 1×SSPE +0.1% (w/v) SDS at 65° C. The filter was blotted dry and exposed for one to seven days. The gene recognises two transcripts (6.0 and 6.5 kb) which appear to be expressed in all stages examined, however, the levels of expression differ in different stages. It should be noted that the same two transcripts are recognised by probes specific to the DNA binding domain and the ligand binding domain, indicating that the two transcripts arise from the same gene either by alternative splicing or alternative use of polyadenylation sites.

In summary, adult and 5th instar larvae have lower levels of expression while all other tissues have subtantial levels of expression.

EXAMPLE II

Expression of Heliothis Ecdysone Receptor in Mammalian Cells

To demonstrate that the cDNA encodes a functional ecdysone receptor, effector constructs were generated containing the HEcR under the control of the CMV (cytomegalovirus) promoter, and the DNA expressed in mammalian cells.

Effector Constructs

A first mammalian expression plasmid was constructed by placing a HindIII/NotI pSK19R fragment into the pcDNA3 HindIII/NotI vector resulting in pcDNA319R (FIG. 7).

A second effector plasmid was constructed wherein the non-coding region of the cDNA 19R was deleted and a consensus Kozak sequence introduced. The mutagenesis was carried out by PCR amplifying a DNA fragment with the oligo HecRH3C (Sequence Id No. 21):

5'aattaagcttccaccatgccgttaccaatgccaccgaca 3' containing a unique HindIII restriction enzyme recognition site followed by the mammalian Kozak consensus sequence, and HecRNdeI (Sequence Id No. 22):

5'cttcaaccgacactcctgac 3'.

The resulting 353 bp PCR fragment was restriction enzyme digested with HindIII and NdeI, gel purified and ligated with 19R NdeI/NotI fragment into a pcDNA3 HindIII/NotI vector resulting in pcDNA3HecR.

A third effector construct was made with the 5' end sequences of pSK16.1 by PCR. The PCR approach involved PCR amplifying the 5' end sequences using a 5' oligonucleotide containing a HindIII restriction cloning site, the Kozak consensus sequence followed by nucleotide sequence encoding for a Methionine start and two Arginines to be added to the 5' end of the amplified fragment:

16H3K (Sequence Id No. 28)

5' attaagcttgccgccatgcgccgacgctggtataacaacggaccattc 3', the 3' oligonucleotide used was HecrNdeI. The resulting fragment was restriction enzyme digested, gel purified and subcloned with an NdeI/NotI 19R fragment into pcDNA3 NdeI/NotI vector. The plasmid was named pcDNA3H3KHEcR.

A fourth effector construct was produced which contains the extended N-terminal end sequence obtained from the 5'RACE experiment. Thus, a, PCR approach was followed to introduce the new 5' end sequences in addition to a consensus Kozak sequence and a HindIII unique cloning-sequence. The sense oligonucleotide used was RACEH3K (Sequence Id No. 29):

5+ attaagcttgccgccatgtccctcggcgctcgtggatac 3', while the antisense primer was the same as that used before (HecrNdeI). The cloning strategy was the same as used for the pcDNA3H3KHEcR to give rise to pcDNA3RACEH3KHEcR.

The PCR mutagenesis reactions were carried out in the same manner for all constructs. The PCR conditions used were 1 minute at 94° C., 1 minute at 60° C. and 1 minute at 72° C. for 15 cycles. The reactions conditions were 50 mM Tris-HCl (pH8.4), 25mM KCl, 200 mM dNTPs (dATP, dCTP, dGTP and dTTP), 200 nM of each oligonucleotide and 2.5 U/Reaction of Taq DNA polymerase. For each construct at least 5 independant PCR reactions were carried out and several clones were sequenced to insure that at least one is mutation free.

Reporter Construct

The reporter plasmid to be co-transfected with the expression vector contained 4 copies of the Hsp27 ecdysone response element (Riddihough and Pelham, 1987) fused to B-globin promoter and the B-Galactosidase gene. The tandem repeats of the ecdysone response element were synthesised as two complementary oligonucleotides which when annealed produced a double stranded DNA molecule flanked by an SpeI site at the 5' end and a ClaI site at the 3' end:

Recr3A (Sequence Id No. 30)

5'ctagtagacaagggttcaatgcact-tgtccaataagcttagacaagggttcaatgcacttgtccaatgaattc agacaagggttcaatgcacttgtc-caatctgcagagacaagggttcaatgcacttgtccaatat 3'

Recr3B (Sequence Id No. 31)

5'cgatattggacaagtgcattgaaccct-tgtctctgcagattggacaagtgcattgaaccttgtctgaattcatt ggacaagtgcattgaaccct-tgtctaagcftattggacaagtgcattgaaccttgtcta 3'.

The resulting 135 bp DNA fragment was ligated to the vector pSWBGAL SpeI/ClaI resulting in pSWREcR4 (FIG. 8). The co-transfection of the two plasmid should result in B-galactosidase activity in the presence of ligand. The experiment relies upon the presence of RXR (a homologue of ultraspiracle) in mammalian cells for the formation of an active ecdysone receptor.

Mammalian Transfection Methods

Transfections of mammalian cell lines (CHO-K1 Chinese hamster ovary)-ATCC number CCL61 or cos-1 (Monkey cell line) were performed using either calcium phosphate precipitation (Gorman, Chapter 6 of "DNA cloning: a practical approach. Vol 2 D. M. Glover ed/.(1985) IRL Press, Oxford) or using LipofectAMINE (Gibco BRL Cat. No. 18324-012, following manufacturers instructions). Human Epithelial Kidney 293 cells were transfected using analogous methods.

Results—Native HEcR Drives Transient Reporter Gene Expression in Mammalian Cells Co-transfection of pcDNA3H3KHEcR (Effector) and reporter constructs into Human Epithelial Kidney 293 cells (HEK293) in the presence of either Muristerone A or RH5992 resulted in a 2–3 fold induction of reporter activity compared to the no chemical controls (FIG. 9). The HEK293 cells were used since they are known to have constitutive levels of αRXR which have been demonstrated to be necessary for Drosophila EcR activation by Muristerone A (Yao., et al., 1993). Moreover, to further investigate the need for RXR interactions, αRXR was co-transfected into HEK293 cells (along with the effector and reporter) resulting in a 9 fold induction of reporter activity compared to the untreated cells (FIG. 9). The co-transfection of αRXR with reporter and effector increased by four fold the reporter activity compared to cells transfected with effector and reporter alone. Induction was observed both in the presence of either Muristerone A or RH5992. These data clearly demonstrate that the cDNA HEcR encodes a functional ecdysone receptor. Moreover, The ability of HEcR to complex with αRXR and bind Muristerone A or RH5992 provide evidence for the usage of the entire HEcR as a component of a mammalian gene switch. In particular, it offers the advantage of reducing uninduced expression of target gene since ecdysone receptor and response elements are not present in mammalian cells.

EXAMPLE III

Chimeric Constructs and Ligand Validation in Maize Protoplasts

In order to apply the ecdysone receptor as an inducible system it was deemed necesary to simplify the requirements of the system by avoiding the need of a heterodimer formation to obtain an active complex. The glucocorticoid receptor is known to form homodimers and chimeric constructs of the glucocorticoid receptor transactivating and DNA binding domains fused to the ecdysone receptor hinge and ligand binding domains have been shown to be active as homodimers in mammalian cells in the presence of Muristerone A (an ecdysone agonist) (Christopherson et al., 1992). However, the chimeric receptor is not responsive to 20-hydroxyecdysone (Christopherson et al., 1992).

The analysis of the activation of the glucocorticoid/Heliothis ecdysone chimeric receptor entailed the production of two other control effector constructs. The first one of the constructs contained the intact glucocorticoid receptor while the second one contained a glucocorticoid/Drosophila ecdysone chimeric receptor.

Effector Constructs

The glucocorticoid receptor DNA for the Maize transient expression construct was produced via the polymerase chain reaction (PCR) of Human Fibrosarcoma cDNA (HT1080 cell line, ATCC#CCl121) library (Clontech)(see Hollenberg et al., 1985). The PCR approach taken was to amplify the 2.7 kb fragment encoding the glucocorticoid receptor in two segments. The first segment entails the N-terminal end up to and including the DNA binding domain while the second fragment begins with the hinge region (amino acid 500) thought to the end of the reading frame. Thus, the PCR primer for the N-terminal end segment was designed to contain an EcoRI site and the Kozak consensus sequence for translation initiation:

GREcoRI (Sequence Id No. 32)
5'attgaattccaccatggactccaaagaatcattaactc 3'.

The 3'end primer contains a XhoI site in frame with the reading frame at amino acid 500 of the published sequence:

GRXhoI (Sequence Id No. 33)
5' gagactcctgtagtggcctcgagcattccttttatttttc 3'.

The second fragment of the glucocorticoid receptor was produced with a 5' end oligonucleotide containing an XhoI site in frame with the open reading frame at the beginning of the hinge region (amino acid 500):

GRHinge (Sequence Id No. 34)
5' attctcgagattcagcaggccactacaggag 3' while the 3' end oligonucleotide contained an EcoRI site 400 bp after the stop codon:

GRStop (Sequence Id No.35)
5' attgaattcaatgctatcgtaactatacaggg 3'.

The glucocorticoid receptor PCR was carried out using Vent polymerase (Biolabs) under hot start conditions followed by 15 cycles of denaturing (94° C. for 1 minute), annealing (66° C. for 1 minute) and DNA synthesis (72° C. for 3 minute). The template was produced by making first strand cDNA as described in the TA cloning kit (Invitrogen) after which the PCR was carried out in 10 mM KCl, 10 mM $(NH_4)_2SO_4$, 20 mM TRIS-HCl pH 8.8, 2 mM $MgSO_4$, 0.1% (v/v) Triton X-100, 200 mM dNTPs, 100 ng of each Primer and 2 U of Vent Polymerase. The PCR products was restriction enzyme digested with EcoRI and XhoI and subcloned into pBluescript SK (pSK) EcoRI. The resulting plasmid pSKHGI was sequenced and found to lack any mutations from the published sequences (apart from those introduced in the PCR primers) (Hollenberg et al., 1985).

The 2.7 kb EcoRI fragment was subcloned into the vector pMF6PAT EcoRI resulting in pMF6HGIPAT (FIG. 10).

(ii) Maize expression construct containing a Glucocorticoid/Drosophila ecdysone chimeric receptor.

The glucocorticoid receptor portion of the chimeric receptor was isolated from pSKHGI by producing a 1.5 kb BamHI/XhoI restriction fragment containing the N-terminal end up to and including the DNA binding domain.

The Drosophila ecdysone receptor portion was isolated through PCR of first stand cDNA prepared from Drosophila adult mRNA. The PCR was carried out using a 5' oligonucleotide containing a SalI site (i.e. Drosophila ecdysone receptor contains a XhoI site at the end of the ligand binding domain), which starts at the beginning of the hinge region (amino acid 330):

Ecr8 (Sequence Id No. 36)
5' attgtcgacaacggccggaatggctcgtcccggag 3'.

The 3' end oligonucleotide contains an BamHI site adjacent to the stop codon:

EcRstop (Sequence Id No. 37)
5' tcgggctttgttaggatcctaagccgtggtcgaatgctccgacttaac 3'.

The PCR was carried out under the conditions described for the amplification of the Glucocorticoid receptor and yielded a 1.6 kb fragment. The fragment was introduced into pSK SalI/BamHI and the sequence determined and compared to the published one (Koelle et al., 1991).

The maize transient expression plasmid was produced by introducing into pMF6 BamHI vector the 1.5 kb BamHI/XhoI glucocorticoid receptor fragment and the 1.6 kb SalI/BamHI Drosophila receptor portion to yield the chimeric plasmid pMF6GREcRS (FIG. 9).

(iii) Construction of the Glucocorticoid/Heliothis ecdysone chimeric receptor Maize transient expression plasmid.

The Glucocorticoid receptor portion of the chimera was produced as describe in Example II(ii). The production of the Heliothis ecdysone receptor portion involves the introduction of a SalI recognition site at the DNA binding/hinge domain junction (amino acid 229). The addition of the SalI site:

Hecrsal (Sequence Id No. 38)
5'attgtcgacaaaggcccgagtgcgtggtgccggag 3' was achieved via PCR mutagenesis making use of an unique AccI site 107 bp downstream of the junction point (or 1007 bp relative to Sequence Id No. 4):

Hecracc (Sequence Id No. 39)
5' tcacattgcatgatgggaggcatg 3'.

The PCR was carried out using Taq polymerase (2.5 U) in a reaction buffer containing 100 ng of template DNA (pSK19R), 100 ng of Hecrsal and Hecracc, 20 mM TRIS-HCl pH 8.4, 50 mM KCl, 10 mM $MgCl_2$, 200 mM dNTPs. The reaction was carried out with an initial denaturation of 3 minutes followed by 15 cycles of denaturation (1 minute at 94° C.), annealing (1 minute at 60° C.) and DNA synthesis (1 minute at 72° C.). The DNA was restriction enzyme digested and subcloned into pSK SalI/SacI with the 1.2 kb AccI/SacI 3' end HecR fragment to yield pSK HeCRDEF (or containing the hinge and ligand binding domains of the Heliothis ecdysone receptor). The construction of the maize transient expression plasmid containing the Glucocorticoid/Heliothis ecdysone chimeric receptor involved the ligation of pMF6 EcoRI/SacI with the 1.5kb EcoRI/XhoI fragment of Glucocorticoid receptor N-terminal end and the 1.2 kb SalI/SacI fragment of pSk HEcRDEF to yield pMF6GRHEcR (FIG. 10).

Reporter Plasmids

Two reporter plasmids were made by inserting the into p221.9 or p221.10 BamHI/HindIII vectors two pairs or oligonucleotides containing six copies of the glucocorticoid response element (GRE). The two sets of oligonucleotides were designed with restriction enzyme recognition sites so as to ensure insertion of the two pairs in the right orientation. The first oligonucleotide pair GRE1A/B is 82 nucleotides long and when annealed result in a DNA fragment flanked with a HindIII site at the 5' end and a SalI site at the 3' end:

GRE1A (Sequence Id No. 40)
  5'agcttcgactgtacaggatgttctagc-
  tactcgagtagctagaacatcctgtacagtcgagtagctagaacat cct-
  gtacag 3'
GRE1B (Sequence Id No. 41)
  5'tcgactgtacaggatgtctagctactc-
  gactgtacaggatgtctagctactcgagtcgctagaacatcctgta
  cagtcga 3'.

The second pair of oligonucleotides is flanked by a SalI site at the 5' end and a BamHI site at the 3' end
GRE2A (Sequence Id No. 42)
  5' tcgactagctagaacatcctgtacagtcgagtagctagaacatcctgt
  acagtcgagtagctagaacatcctgtacag 3', and
GRE2B (Sequence Id No. 43)
  5'gatcctgtacaggatgttctagctactc-
  gactgtacaggatgttctagctactcgactgtacaggatg ttctagctag
  3'.

The resulting plasmids were named p221.9GRE6 (FIG. 13) and p221.10GRE6 (FIG. 14)(used in later Example). The difference between p221.9 and p221.10 plasmids is that p221.9 contains the −60 35SCaMV minimal promotor while p221.10 (p221.10GRE6) contains the −46 35SCaMV minimal promotor.

Method

Protoplasts were isolated from a maize suspension culture derived from BE70×A188 embryogenic callus material, which was maintained by subculturing twice weekly in MS0.5$_{mod}$. (MS medium supplemented with 3% sucrose, 690 mg/l proline, 1 g/l myo-inositol, 0.2 g/l casein acid hydrolysate, 0.5 mg/l 2,4-D, pH5.6). Cells from suspensions two days post subculture were digested in enzyme mixture (2.0% Cellulase RS, 0.2% Pectolyase Y23, 0.5M Mannitol, 5 mM $CaCl_2 2H_2O$, 0.5% MES, pH5.6, ~660 mmol/kg) using ~10 ml/g cells, incubating at 25° C., dim light, rotating gently for −2 hours. The digestion mixture was sieved sequentially through 250 μm and 38 μm sieves, and the filtrate centrifuged at 700 rpm for 3.5 minutes, discarding the supernatant. The protoplasts were resuspended in wash buffer (0.358M KCl, 1.0 mM $NHNO_3$, 5.0 mM $CaCl_2 2H_2O$, 0.5 mM $KH_2PO_4$, pH4.8, ~670 mmol/kg) and pelleted as before. This washing step was repeated. The pellet was resuspended in wash buffer and the protoplasts were counted. Transformation was achieved using a Polyethylene glycol method based on Negrutiu et.al. Protoplasts were resuspended at $2×10^6$/ml in MaMg medium (0.4M Mannitol, 15 mM $MgCl_2$, 0.1% MES, pH5.6, ~450 mmol/kg) aliquotting 0.5 ml/treatment (i.e. $1×10^6$ protoplasts/treatment). Samples were heat shocked at 45° C. for 5 minutes then cooled to room temperature. 10 μg each of p221.9GRE6 and pMF6HR1PAT (GR) (1 mg/ml)/treatment were added and mixed in gently, followed by immediate addition of 0.5 ml warm (~45° C.) PEG solution (40% PEG 3,350 MW in 0.4M Mannitol, 0.1M $Ca(NO_3)_2$, pH8.0), which was mixed in thoroughly but gently. Treatments were incubated at room temperature for 20–25 minutes, then 5 ml 0.292M KCl (pH5.6, ~530 mmol/kg) was added step-wise, 1 ml at a time, with mixing. The treatments were incubated for a further 10–15 minutes prior to pelleting the protoplasts by centrifuging as before. Each protoplast treatment was resuspended in 1.5 ml culture medium (MS medium, 2% sucrose, 2 mg/l 2,4-D, 9% Mannitol, pH5.6, ~700 mmol/kg) +/−0.0001M dexamethasone (glucocorticoid). The samples were incubated in 3 cm dishes at 25° C., dark, for 24–48 hours prior to harvesting. Fluorometric assays for GUS activity were performed with the substrate 4-methylumbelliferyl-D-glucuronide using a Perkin-Elmer LS-35 fluorometer (Jefferson et al., 1987). Protein concentration of tissue homogenates were determined by the Bio-Rad protein assay (Bradford, 1976). The method was repeated for each effector construct.

Results

Reporter Gene Assay

A reporter gene construct (p221.9GRE6) was generated containing the GUS reporter gene under the control of a −60 CaMV 35S promoter with 6 copies of the glucocorticoid response element. To test this construct was functional in maize protoplasts a co-transformation assay was performed with the reporter construct p221.9GRE6 and the effector construct pMF6HR1PAT (GR) construct containing the entire glucorticoid receptor.

FIG. 15 shows that Reporter p221.9GRE6 alone or reporter plus effector pMF6HR1PAT (GR) with no activating chemical gave no significant expression. When reporter plus effector were co-transformed into maize protoplasts in the presence of 0.0001M dexamethasone (glucocorticoid), a significant elevation of marker gene activity was observed (FIG. 15). The response is specific to glucorticoid as the steroid Muristerone A does not lead to induced levels of expression. These studies clearly show the reporter gene construct p221.9GRE6 is capable of monitoring effector/ligand mediated gene expression.

Chimeric Ecdysone Effector Constructs Mediate Inducible Expression in Maize Transient Protoplasts Assays A chimeric effector plasmid pMF6GREcRS was constructed, containing the ligand binding domain from the Drosophila ecdysone receptor and the DNA binding and transactivation domain from the glucorticoid receptor. To confirm the reporter gene construct p221.9GRE6 could respond to a chimeric ecdysone effector construct, a series of co-transformation into maize protoplasts was performed.

FIG. 16 shows that reporter (p221.9GRE6) alone or reporter plus effector (pMF6GREcRS) with no activating chemical, gave no significant expression in maize protoplasts. When reporter plus effector were co-transformed into maize protoplasts in the presence of 100 μM Muristerone A, a significant elevation of marker gene activity was observed. The response was specific to Muristerone A, as the steroid dexamethasone did not lead to induced levels of expression. These studies clearly showed the reporter gene construct p221.9GRE6 is capable of monitoring chimeric ecdysone effector/ligand mediated gene expression.

A second chimeric effector construct pMF6GRHEcR, was generated containing the ligand binding domain from Heliothis ecdysone receptor. When co-transformed into maize protoplasts with the reporter plasmid p221.9GRE6, no response to 100 μM Muristerone or 100 μM dexamethasone was observed (FIG. 17). These data clearly show the Drosophila and Heliothis ligand binding domains exhibit different properties.

When the effector plasmid pMF6GREcRS, containing the ligand binding domain from Drosophila , was tested with the reporter p221.9GRE6 in presence of the non-steroidal ecdysone agonists RH5849 and RH5992 (mimic), no chemical induced reporter gene activity was observed (FIGS. 18 and 19).

When the effector plasmid pMF6GRHEcR, containing the ligand binding domain from Heliothis, was tested with the reporter p221.9GRE6 in presence of the non-steroidal ecdysone agonists RH5992 (mimic), significant chemical induced reporter gene activity was observed (FIG. 20). These data demonstrate the ligand binding domain from Heliothis has different properties to the Drosophila receptor in that the former responded to the non-steroidal ecdysteroid agonist RH5992. FIG. 21 demonstrates the effector plasmid pMF6GRHEcR confers RH5992 dependant inducibility on the reporter p221.9GRE6 in a dose responsive manner. Induction was observed in a range from 1 μM–100 μM RH5992.

EXAMPLE IV

Testing of Effector Vectors in Tobacco Protoplasts

The experiments carried out in the previous example demonstrated the specific effect of RH5992 (mimic) on pMF6GRHEcR in maize protoplasts. It is the aim in this example to show the generic application to plants of the glucocorticoid/Heliothis ecdysone chimeric receptor switch system. Tobacco shoot cultures cv. Samsun, were maintained on solidified MS medium+3% sucrose in a controlled environment room (16 hour day/8 hour night at 25° C., 55% R.H), were used as the source material for protoplasts. Leaves were sliced parallel to the mid-rib, discarding any large veins and the slices were placed in CPW13M 13% Mannitol, pH5.6, ~860 mmol/kg) for ~1 hour to preplasmolyse the cells. This solution was replaced with enzyme mixture (0.2% Cellulase R10, 0.05% Macerozyme R10 in CPW9M (CPW13M but 9% Mannitol), pH5.6, ~600 mmol/kg) and incubated in the dark at 25° C. overnight (~16 hours). Following digestion, the tissue was teased apart with forceps and any large undigested pieces were discarded. The enzyme mixture was passed through a 75 μm sieve and the filtrate was centrifuged at 600 rpm for 3.5 minutes, discarding the supernatant. The pellet was resuspended in 0.6M sucrose solution and centrifuged at 600 rpm for 10 minutes. The floating layer of protoplasts was removed using a pasteur pipette and diluted with CPW9M (pH5.6, ~560 mmol/kg). The protoplasts were again pelleted by centrifuging at 600 rpm for 3.5 minutes, resuspended in CPW9M and counted. A modified version of the PEG-mediated transformation above was carried out. Protoplasts were resuspended at $2 \times 10^6$/ml in MaMg medium and aliquotted using 200 μl/treatment (i.e. $4 \times 10^5$ protoplasts/treatment). 20 μg each of pMF6GRHEcRS and p221.9GRE6 DNA (1 mg/ml) were added followed by 200 μl PEG solution and the solutions gently mixed. The protoplasts were left to incubate at room temperature for 10 minutes before addition of 5 ml MSP19M medium (MS medium, 3% sucrose, 9% Mannitol, 2 mg/l NAA, 0.5 mg/l BAP, pH5.6, ~700 mmol/kg) +/–10 μM RH5992. Following gentle mixing, the protoplasts were cultured in their tubes, lying horizontally at 25° C., light. The protoplasts were harvested for the GUS assay after ~24 hours.

Effector Construct (i) Construction of a Dicotyledonous expression vector

The vector produced is a derivative of pMF6. pMF6GREcRS was restriction enzyme digested with PstI to produce 3 fragments namely, 3.4(Adh Intronless pMF6), 3.2(GREcRS) and 0.5(Adh intron I) kb). Isolation and religation of the 3.4 and 3.2 kb fragments resulted in pMF7GREcRS (FIG. 22). pMF7GREcRS was restriction enzyme digested with EcoRI/SacI resulting in the 3.4 kb pMF7 EcoRI/SacI vector which when isolated and purified was ligated to a 1.5 kb EcoRI/XhoI N-terminal end of the glucocorticoid receptor and the 1.2 kb SalI/SacI Heliothis ecdysone C-terminal end sequences to produce pMF7GRHEcR (FIG. 23).

Reporter Plasmid

The reporter plasmids constructed for the maize transient experiments were the same as those used without alteration in the tobacco leaf protoplast transient expression experiments.

Results—Chimeric Ecdysone Effector Constructs Mediate Inducible Expression in Tobacco Transient Protoplast Assays Experiments were performed to demonstrate that the effector plasmid pMF6GRHEcR can confer chemical dependant inducible expression on the reporter p221.9GRE6 in tobacco mesophyll protoplasts.

FIG. 24 shows that reporter (p221.9GRE6) alone or reporter plus effector (pMF7GRHEcR) with no activating chemical, gave no significant expression in tobacco protoplasts. When reporter plus effector were co-transformed into tobacco protoplasts in the presence of 10 μM RH5992, a significant elevation of marker gene activity was observed. These data show a chimeric ecdysone effector construct, containing the Heliothis ligand binding domain can confer non-steroidal ecdysteroid dependant expression on reporter gene constructs in both monocotyledonous and dicotyledonous species.

EXAMPLE V

Chimeric Activity in Mammalian Cells

Effector Constructs (i) Construction of Glucocorticoid/Heliothis ecdysone chimeric receptor.

The mammalian expression vector used in this experiment was pcDNA3 (Invitrogen). The GRHEcR 2.7kb BamHI DNA fragment (isolated from pMF6GRHEcR) was introduced into the pcDNA3 BamHI vector. The recombinants were oriented by restriction enzyme mapping. The DNA sequence of the junctions was determined to ensure correct orientation and insertion (pcDNA3GRHEcR, FIG. 25).

Reporter Construct

The reporter plasmid for mammalian cell system was produced by taking pSWBGAL plasmid and replacing the CRESW SpeI/ClaI fragment for a synthetic 105 bp DNA fragment containing 4 copies of the glucocorticoid response element (GRE) and flanked by SpeI at the 5' end and AflII at the 3' end.

The oligonucleotides were synthesised using the sequences:

GREspeI (Sequence Id No. 44) 5'ctagttgtacaggatgttctagc-tactcgagtagctagaacatcctgtacagtcgagtagctagaac atcctg-tacagtcgagtagctagaacatcctgtacac 3', and GREafl2 (Sequence Id No. 45)
5'ttaagtgtacaggatgttctagctactc-gactgtacaggatgttctagctactcgactgtacaggatgt tctagc-tactcgagtagctagaacatcctgtacaa 3'.

The two oligonucleotides were purified annealed and ligated to pSWBGAL SpeI/AflII to produce pSWGRE4 (FIG. 26).

Results—Chimeric HEcR Drives Transient Reporter Gene Expression in Mammalian Cells No expression was detected when a reporter gene construct pSWGRE4, comprising of a minimal β-globin promoter containing four copies of the glucocorticoid response element, fused to a β-galactosidase reporter gene, was introduced into CHO cells. Similarly, no expression was detected when pSWGRE4 and an effector plasmid pcDNA3GRHEcR, containing the transactivation and DNA binding domain from the glucocorticoid receptor and the ligand binding domain from the Heliothis ecdysone receptor, under the control of the CMV promoter were co-transformed into CHO-K1 or HEK293 cells. When co-transformed CHO (FIG. 27) and HEK293 cells (FIG. 28) were incubated in the presence of the non-steroidal ecdysone agonists RH5992 (mimic), significant chemical induced reporter gene activity was observed. Equally, induction of reporter activity was observed when HEK293 cells transfected with pcDNA3GRHEcR and reporter were treated with Muristerone A (FIG. 28).

EXAMPLE VI

Screening System Allows New Chemical Activators and Modified Ligand Binding Domains to be Tested in Mammalian Cells The basis of a screening system are in place after the demonstration that the chimeric receptor was activated in the presence of RH5992. A screen was carried out using CHO cells transiently transfected with both pSWGRE4 (reporter) and pcDNA3GRHEcR (effector) constructs. In the first instance 20 derivatives compounds of RH5992 were screened. It was observed that 7 out of the 20 compounds gave an increased reporter gene activity compared to untreated cells. A second screen was carried out in which 1000 randomly selected compounds were applied to transiently transfected CHO cells. Two compounds were found to activate reporter gene activity above that from the untreated controls. The second screen suggest that this cell based assay is a robust and rapid way to screen a small library of compounds, where a thousand compounds can be put through per week.

EXAMPLE V

Stably Transformed Tobacco Plants

Stable Tobacco Vectors

The components of the stable Tobacco vectors were put together in pBluescript prior to transfer into the binary vector. The production of stable transformed plants entails the production of a vector in which both components of the switch system (ie. effector and reporter) are placed in the same construct to then introduce into plants.

The methodology described below was used to produce four different stable Tobacco vectors. The method involves three steps:

1. pBluescript SK HindIII/EcoRI vector was ligated to either GRE6-4635SCaMVGUSNOS HindIII/EcoRI (from p221.10GRE6) or GRE6-6035SCaMVGUSNOS HindIII/EcoRI (from p221.9GRE6) resulting in plasmid pSK46 and pSK-60.
2. This step involves the addition of the chimeric receptor (35SGRHEcRNOS or 35SGRVP16HEcRNOS) to pSK-60 or pSK-46. Thus a pSK-60 (or pSK-46) XbaI vector was ligated with either the 3.4 kb 35SGRHEcRNOS XbaI or the 3.0 kb 35SGRVP16HEcRNOS XbaI DNA fragment to produce pSKES1 (pSKGRE6-6035SCaMVGUSNOS-35SGRHEcRNOS), pSKES2 (pSKGRE64635SCaMVGUSNOS-35SGRHEcRNOS), pSKES3 (pSKGRE6-6035SCaMVGUSNOS-35SGRVP16HEcRNOS) and pSKES4 (pSKGRE64635SCaMVGUSNOS-35SGRVP16HEcRNOS).
3. Transfer from pBluescript based vectors to binary vectors. The transfer of the ES1 (FIG. 29) ES2 (FIG. 30), ES3 (FIG. 31) or ES4 (FIG. 32) DNA fragments into the binary vector JR1 involves five steps:
   (i) Restriction enzyme digestion of pSKES1 (ES2, ES3, and ES4) with ApaI and NotI to liberate the insert from the vector pBluescript.
   (ii) The two DNA fragments were BamHI methylated for 2 hours at 37° C. in TRIS-HCl, MgCl, 80 uM SAM (S-adenosylmethionine) and 20 U of BamHI methylase.
   (iii) Ligate a ApaI/NotI linker onto the fragment. The linker was designed to have an internal BamHI site ApaBNot1 (Sequence Id No. 46)
      5' cattggatccttagc 3' and
      ApaBNot2 (Sequence Id No. 47)
      5' ggccgctaaggatccaatgggcc 3'.
   (iv) Restriction enzyme digest the protected and linkered fragment with BamHI and fractionate the products on a 1%(w/v) agarose gel. The protected DNA fragment (5.5 kb) was cut out of the gel and purified.
   (v) A ligation of JRI BamHI vector with the protected band was carried out to produce JRIESI (JRIES2, JRIES3 or JRIES4). The DNA of the recombinant was characterised by restriction mapping and the sequence of the junctions determined.

The plant transformation construct pES1, containing a chimeric ecdysone receptor and a reporter gene cassette, was transferred into *Agrobacterium tumefaciens* LBA4404 using the freeze/thaw method described by Holsters et al. (1978). Tobacco (*Nicotiana tabacum* cv Samsun) transformants were produced by the leaf disc method (Bevan, 1984). Shoots were regenerated on medium containing 100 mg/l kanamycin. After rooting, plantlets were transferred to the glasshouse and grown under 16 hour light/8 hour dark conditions.

Results—Chimeric Ecdysone Effector Constructs Mediate Inducible Expression in Stably Tobacco Plants Transgenic tobacco plants were treated in cell culture by adding 100 $\mu$M RH5992 to MS media. In addition seedlings were grown hydroponically in the presence or absence of RH5992. In further experiments 5 mM RH5992 was applied in a foliar application to 8 week old glasshouse grown tobacco plants. In the three methods described uninduced levels of GUS activity were comparable to a wild type control, while RH5992 levels were significantly elevated.

Ecdysone Switch Modulation and Optimisation

EXAMPLE VIII

Yeast Indicator Strains for Primary Screen of Chemical Libraries

A set of yeast indicator strains was produced to use as a primary screen to find chemicals which may be used in the gene switch. The properties of the desired chemicals should include high affinity resulting in high activation but with different physico-chemical characteristics so as to increase the scope of application of the technology. Moreover, the production of this strain also demonstrates the generic features of this switch system.

Effector Vector

A base vector for yeast YCp15Gal-TEV-112 was generated containing:

Backbone—a modified version of pRS315 (Sikorski and Hieter (1989) Genetics 122, 19–27)—a shuttle vector with the LEU2 selectable marker for use in yeast;

ADH1 promoter (BamHI-Hind III fragment) and ADH1 terminator (Not I-Bam HI fragment) from pADNS (Colicelli et al PNAS 86, 3599–3603);

DNA binding domain of GAL4 (amino acids 1–147; GAL4 sequence is Laughon and Gesteland 91984) Mol. Cell Biol. 4, 260–267) from pSG424 (Sadowski and Ptashne (1989) Nuc. Acids Res. 17, 7539);

Activation domain—an acidic activation region corresponding to amino acids 1–107 of activation region B112 obtained from plasmid pB112 (Ruden et al (1991) Nature 350, 250–252).

The plasmid contains unique Eco RI, Nco I and Xba I sites between the DNA binding domain and activation domains.

Into this vector a PCR DNA fragment of the Heliothis ecdysone receptor containing the hinge, ligand binding domains and the C-terminal end was inserted. The 5' oligonucleotide is flanked by an NcoI restriction recognition site and begins at amino acid 259:

HecrNcoI (Sequence Id No. 48)

5' aattccatggtacgacgacagtagacgatcac 3'.

The 3' oligonucleotide is flanked by an XbaI site and encodes for up to amino acid 571:

HecRXbaI (Sequence Id No. 49)

5' ctgaggtctagagacggtggcgggcggcc 3'.

The PCR was carried out using vent polymerase with the conditions described in Example IA. The fragment was restriction enzyme digested with NcoI and XbaI purified and ligated into YCp15GALTEV112 NcoI/XbaI vector to produce YGALHeCRB112 or TEV-B112 (FIG. 34). In order to reduce constitutive activity of the YGALHeCRB112 plasmid a YGALHeCR plasmid was produced in which the B112 activator was deleted by restriction enzyme digesting YGALHeCRB112 with XbaI/SpeI followed by ligation of the resulting vector (ie. SpeI and XbaI sites when digested produce compatible ends)(TEV-8, FIG. 33). An effector plasmid was constructed whereby the B112 transactivating domain was excised from YGalHecRB112 with XbaI and replaced with the VP16 transactivation domain DNA fragment (encoding amino acids 411 and 490 including the stop codon). The resulting vector was named YGalHecRVP16 or TEVVP16-3 (FIG. 35).

Reporter Construction for Yeast

The S. cerevisiae strain GGY1::171 (Gill and Ptashne (1987) Cell 51, 121–126), YT6::171 (Himmelfarb et al (1990) Cell 63, 1299–1309) both contain reporter plasmids consisting of the GALA-responsive GAL1 promoter driving the E. coli B-galactosidase gene. These plasmids are integrated at the URA3 locus. The reporter strain YT6::185 contains the reporter plasmid pJP185 (two synthetic GAL4 sites driving the B-galactosidase gene) integrated at the URA3 locus of YT6 (Himmelfarb et al). (Note—the parental strains YT6 and GGY1 have mutations in the GAL4 and GAL80 genes, so the reporter genes are inactive in the absence of any plasmids expressing GAL4 fusions).

Yeast Assay

Standard transformation protocols (Lithium acetate procedure) and selection of colonies by growth of cells on selective media (leucine minus medium in the case of the YCp15Gal-TEV-112 plasmid)—as described in Guthrie and Fink)1991) Guide to Yeast Genetics and Molecular Biology: Methods in Enzymology Vol. 194 Academic Press) and the reporter gene assay is a modification of that described in Ausabel et al (1993) Current Protocols in Molecular Biology (Wiley) Chapter 13).

Results—Automated Screening System Allows New Chemical Activators and Modified Ligand Binding Domains to be Tested in Yeast An effector vector pYGALHEcRB112 has been generated containing a GAL4 DNA binding domain, a B112 activation domain and the ligand binding region from Heliothis virescens. In combination with a GAL reporter vector, pYGA-LHEcRB112 form the basis of a rapid, high throughput assay which is cheap to run. This cell-based assay in yeast (Saccharomyces cerevisiae) will be used to screen for novel non-steroidal ecdysone agonists which may of commercial interest as novel insecticides or potent activators of the ecdysone gene switch system. The demonstration of an efficient system to control gene expression in a chemical dependant manner, forms the basis of an inducible system for peptide production in yeast.

The yeast screening system forms the basis of a screen for enhanced ligand binding using the lac Z reporter gene vector to quantitatively assay the contribution of mutation in the ligand binding domain. Alternatively, enhanced ligand binding capabilities or with a selection cassette where the lac Z reporter is replaced with a selectable marker such as uracil (URA 3), tryptophan (Trp1) or leucine (Leu2), and histidine (His). Constructs based on pYGALHEcRB112 with alterations in the ligand binding domain are grown under selection conditions which impair growth of yeast containing the wild type ligand binding domain. Those surviving in the presence of inducer are retested and then sequenced to identify the mutation conferring resistance.

EXAMPLE IX

Optimisation of Chimeric Receptor Using a Strong Transactivator

Construction of Mammalian Expression Plasmid with Chimeric Receptor Containing Heipex Simplex VP16 Protein Sequences.

The construction of this chimeric receptor is based on replacing the sequences encoding for the glucocorticoid receptor transactivating domain with those belonging to the VP16 protein of Herpes simplex. Thus PCR was used to generate three fragments all to be assembled to produce the chimeric receptor. The PCRs were carried out as described in Example II, iii. The first fragment includes the Kozak sequences and methionine start site of the glucocorticoid receptor to amino acid 152 of the glucocorticoid receptor. The oligonucleotides used for the generation of this fragment included an EcoRI site at the 5' end:

GR1A (Sequence Id No. 50)

5' atat*gaattc*caccatggactccaaagaatc 3' and at the 3' end a NheI restriction enzyme recognition site

GR1B (Sequence Id No. 51)

5' atat*gctagc*tgtgggggcagcagacacagcagtgg 3'.

The second fragment also belongs to the glucocorticoid receptor and begins with a NheI site in frame with amino acid 406:

GR2A (Sequence Id No. 52)

5'atatgctagctccagctcctcaacagcaacaac 3' and ends with a XhoI site at amino acid 500:

GR2B (Sequence Id No. 53)

5'atatctcgagcaattcctttattttttc 3'.

The two fragments were introduced into pSKEcoRI/SacI in a ligation containing GR1A/B EcoRI/NheI, GR2A/B NheI/XhoI and HEcR SalI/SacI (from pSKHEcRDEF) to yield pSKGRDHEcR. The GR sequences and junctions of the ligation were found to be mutation free.

The third fragment to be amplified was a sequence between amino acid 411 to 490 of the herpes simplex VP16 protein. The amplified fragment was flanked with SpeI recognition sites. SpeI produces compatible ends to those of NheI sites. The oligonucleotides used VP16C (Sequence Id No. 54)

5' att*actagt*tctgcggcccccccgaccgat 3' and

VP16E (Sequence Id No. 55)

5' aatt*actagt*cccaccgtactcgtcaattcc 3' produced a 180 bp fragment which was restriction enzyme digested with SpeI and introduced into pSKGRΔHEcR NheI vector to produce pSKGRVP16HEcR. The DNA from the latter was sequenced and found to be mutation free, the junctions were also shown to be in frame with those of the glucocorticoid receptor.

The 2.2 kb EcoRV/NotI GRVP16HEcR fragment was introduced into a pcDNA3 EcoRV/NotI vector resulting in pcDNA3GRVP16HEcR (FIG. 36).

Construction of Plant Transient Expression Effector Plasmids Containing the Chimeric Receptor with VP16 Sequences The same procedure was carried out to clone the GRVP16HeCR DNA fragment into tobacco(pMF7b) and maize(pMF6) expression vectors. A 2.2 kb BamHI DNA fragment was isolated from pcDNA3GRVP16HeCR and ligated in to the pMF6 BamHI (or pMF7b BamHI) vector to produce pMF6GRVP16HeCR (FIG. 37) (or pMF7GRVP16HeCR) (FIG. 38).

Results—Addition of Strong Activation Domains Enhance Ecdysone Switch System

The VP16 transactivation domain from herpes simplex virus has been added to a maize protoplast vector pMF6GRHEcR to generate the vector pMF6GRVP16HEcR. When co-transformed into maize protoplasts with the reporter construct p221.9GRE6, in the presence of 100 µM RH5992, enhanced levels of expression were seen over pMF6GRHEcR. FIG. 39, shows that RH5992 is able to induce GUS levels comparable to those observed with the positive control (p35SCaMVGUS), moreover, a dose response effect is observable.

VP16 enhanced vectors (pES3 and pES4) have been generated for stable transformation of tobacco. Following transformation transgenic progeny containing pES3 and pES4, gave elevated GUS levels following treatment with RH5992, relative to comparable transgenic plants containing the non-VP16 enhanced vectors pES1 and pES2.

An enhanced mammalian vector pcDNA3GRVP16HEcR was prepared for transient transfection of mammalian cell lines. Elevated reporter gene activities were obtained relative to the effector construct (pCDNA3GRHEcR) without the VP16 addition.

"Acidic" activation domains are apparently "universal" activators in eukaryotes (Ptashne (1988) Nature 335 683–689). Other suitable acidic activation domains which have been used in fusions are the activator regions of GAL4 itself (region I and region II; Ma and Ptashne (Cell (1987) 48, 847–853), the yeast activator GCN4 (Hope and Struhl (1986) Cell 46, 885–894) and the herpes simplex virus VP16 protein (Triezenberg et al (1988) Genes Dev. 2, 718–729 and 730–742).

Other acidic and non-acidic transcriptional enhancer sequences for example from plant fungal and mammalian species can be added to the chimeric ecdysone receptor to enhance induced levels of gene expression.

Chimeric or synthetic activation domains can be generated to enhance induced levels of gene expression.

EXAMPLE X

Optimisation by Replacement of Heliothis Ligand Binding Domain in Chimeric Effector for that of an Ecdysone Ligand Binding Domain of Another Species Mutagenesis of the ecdysone ligand binding domain results in the increased sensitivity of the chimeric receptor for activating chemical. This can be achieved by deletions in the ligand binding domain, use of error prone PCR (Caldwell et al., PCR Meth. Applic 2, 28–33 1992), and in vitro DNA shuffling PCR (Stemmer, Nature 370, 389–391 1994). To enhance the efficacy of the listed techniques we have developed a screening system for enhanced levels of induced expression (see below).

An alternative strategy to the mutation of a known ligand binding domain is to identify insect species which are particularly sensitive to ecdysteroid agonists. For example *Spodoptera exigua* is particularly sensitive to RH 5992. To investigate the role of the ecdysone receptor ligand binding domain in increased sensitivity to RH5992 we have isolated corresponding DNA sequences from of *S. exigua* (FIG. 40, Sequence ID No. 6). FIG. 41, Sequence ID No. 7 shows a protein alignment of the hinge and ligand binding domains of the *Heliothis virescens* and *Spodoptera exigua* ecdysone receptors. The protein sequence between the two species is well conserved.

Results—Manipulation of the Ligand Binding Domain Leads to Enhanced Induced Expression Isolation of an ecdysone ligand binding domain from another lepidopteran species was carried out by using degenerate oligonucleotides and PCR of first strand cDNA (Perkin Elmer, cDNA synthesis Kit) of the chosen species. The degenerate oligonucleotides at the 5' end were HingxhoA and B and at the 3' end ligandxA/B HingxhoA (Sequence Id No. 56)
  5' attgctcgagaaagiccigagtgcgtigticc 3'
  a t HingxhoB (Sequence Id No. 57)
  5' attgctcgagaacgiccigagtgtgtigticc 3'
  a c LigandxA (Sequence Id No. 58)
  5' ttactcgagiacgtcccaiatctcttciaggaa 3'
  a t c a LigandxB (Sequence Id No. 59)
  5' ttactcgagiacgtcccaiatctcctciaagaa 3'
  a t t a RNA was extracted from 4th instar larvae of *Spodoptera exigua* since *Spodoptera exigua* appears to be more sensitive to RH5992 than Heliothis (Smagghe and Degheele, 1994). The first strand cDNA was used in PCR reactions under the following conditions 20 mM Tris-HCL (pH8.4), 50 mM KCl, 1.5 mM MgCl$_2$, 200 mM dNTPs (dATP,dCTP,dGTP and dTTP) and 0.02 U/ml Taq DNA polymerase and in the presence of 1ug of each Hinge (5'3') and Ligand (5'3') oligonucleotides. The PCR cycling conditions were 94° C. for 1 minute, 60° C. for 2 minutes and 72° C. for 1 minute and 35 cycles were carried out. A sample of the completed reaction was fractionated in a 1% agarose (w/v) 1×TBE gel, and the resulting 900 bp fragment was subcloned into pCRII vector (Invitrogen). The resulting clone (pSKSEcR 1–10) were further characterised and sequenced.

EXAMPLE X

Manipulation of Reporter Gene Promoter Regions Can Modulate Chemical Induced Expression The context of the effector response element in the reporter gene promoter can be used to modulate the basal and induced levels of gene expression. Six copies of the glucorticoid response element were fused to 46 bp or 60 bp of the CaMV 35S promoter sequence. When used with the effector construct pMF7GRHEcRS the reporter gene construct containing 46 bp of the CaMV 35S promoter gave reduced basal and induced levels of GUS expression relative to the 60 bp reporter construct (FIG. 42).

Constructs for plant transformation (pES1 and ES2) have been generated to demonstrate the size of minimal promoter can be used to modulate the basal and induced levels of gene expression in plants.

The number and spacing of response elements in the reporter gene promoter can be adjusted to enhance induced levels of trans-gene expression.

The utility of a two component system (effector and reporter gene cassettes) allows the spatial control of induced expression. Trans-gene expression can be regulated in an tissue specific, organ specific or developmentally controlled manner. This can be achieved by driving the effector construct from a spatially or temporally regulated promoter.

References

Allan, G. F., Tsai, S. Y., Tsai, M.-J. and O'Malley, B. W. (1992a) P.N.A.S. 89, 11750–11754.
Allan, G. F., Leng, X., Tsai, S. Y., Weigel, N. L., Edwards, D. P., Tsai, M.-J. and O'Malley, B. W. (1992b) J. Biol. Chem 267, 19513–19520.
Ashburner, M (1990) Cell 61, 1–3.
Beato, M. (1989) Cell 56, 335–344.
Carlberg, C., Bendik, I., Wyss, A., Meier, E., Sturzenbecker, L. J., Grippo, J. F. and Hunziker, W. (1993) Nature 361, 657–660.
Christopherson, K. S., Mark., M. R., Bajaj, V. and Godowski, P. J. (1992) P.N.A.S. 89, 6314–6318.
Evans, R. M. (1988) Science 240, 889–895.
Green, S. and Chambon, P. (1988) TIGs 11, 309–314.
Heyman, R. A., Mangelsdorf, D. J., Dyck, J. A., Stein, R. B., Eichele, G., Evans, R. M. and Thaller, C. (1992) Cell 68, 397–406.
Hirst, M. C., Bassett, J. H. D., Roche, A. and Davies, K. E. (1992) Trends in Genetics 8, 6–7.
Hogness, D. S., Talbot, W. S., Bender, M. T. and Koelle, M. (1992) X Ecdysone Workshop, Liverpool. Abstract.
Hollenberg, S. M., Weinberger, C., Ong, E. S., Cerelli, G., Oro, A., Lebo, R., Thompson, E. B., Rosenfeld, M. G. and Evans, R. M. (1985) Nature 318, 635–641.
Kliewer, S. A., Umesono, K., Mangeldorf, D. J. and Evans, R. M. (1992) Nature 355, 446–449.
Koelle, M. R., Talbot, W. S., Segraves, W. A., Bender, M. T., Cherbas, P. and Hogness, D. S. (1991) Cell 67, 59–77.
Krust et al, (1986) The EMBO Journal 5, 891–897.
Leid, M., Kastner, P., Lyons, R., Nakshatri, H., Saunders, M., Zacharewski, T., Chen, J-Y., Staud, A., Garnier, J-M., Mader, S. and Chambon, P. (1992a) Cell 68, 377–395.
Leid, M., Kastner, P and Chambon, P. (1992b) TIBs 17, 427–433.
Mangelsdorf, D. J., Borgmeyer, V., Heymann, R. A., Zhou, J. Y., Ong, E. S., Oro, A. E., Kakizuka, A. and Evans, R. M. (1992) Genes and Development 6, 329–344.
Oro, A. E., Mckeown, M. and Evans, R. M. (1990) Nature 347, 298–301.
Riddihough, G. and Pelham, H. R. B. (1987) EMBO Journal 6, 3729–3734.
Segraves, W. A. (1991) Cell 67, 225–228.
Segraves, W. A. and Hogness, D. S. (1990) Genes and Development 4, 204–219.
Smagghe, G. and Degheele, D (1994) Pestic. Sci. 42, 85–92.
Stemmer, W. P. (1994) Nature 370, 389–391.
Thummel, C. S., Burtis, K. S. and Hogness, D. S. (1990) Cell 61, 101–111.
Vegeta, E., Allan, G. F., Schrader, W. T., Tsai, M-J., McDonnell, D. P. and O'Maley, B. W. (1992) Cell 69, 703–713.
Yao, T. P., Segraves, W. A., Oro, A. E., Mckeown, M. and Evans, R. M. (1992) Cell 71, 63–72.
Yao, T-P., Forman, B. M., Jlang, Z., Cherbas, L., Chen, J-Don., Mckeown, M., Cherbas, P. and Evans, R. M. (1993) Nature 366, 476–479.
Yu, V. C., Delsert, C., Andersen, B., Holoway, J. M., Kim, S. Y., Boutin, J-M., Glass, C. K. and Rosenfeld, M. G. (1991) Cell 67, 1251–1266.

What is claimed is:

1. An isolated polypeptide comprising a polypeptide selected from the group consisting of:
   (a) the *Heliothis virescens* ecdysone steroid receptor shown in SEQ ID NO:5;
   (b) the transactivation domain of the *Heliothis virescens* ecdysone steroid receptor shown in amino acids 1–162 of SEQ ID NO:5;
   (c) the DNA binding domain of the *Heliothis virescens* ecdysone steroid receptor shown in amino acids 163–228 of SEQ ID NO:5;
   (d) the, hinge domain of the *Heliothis virescens* ecdysone steroid receptor shown in amino acids 229–326 of SEQ ID NO:5;
   (e) the ligand binding domain of the *Heliothis virescens* ecdysone receptor shown in amino acids 327–545 of SEQ ID NO:5; and
   (f) a derivative of the polypeptide of (a), (b), (d) or (e), wherein the derivative comprises one or more conservatively substituted amino acids and the derivative retains the function of the polypeptide, wherein the function is selected from the group consisting of ecdysone steroid receptor activity, ecdysone steroid receptor transactivation activity, ecdysone steroid receptor hinge domain activity, and ecdysone receptor ligand binding activity.

2. An isolated polypeptide selected from the group consisting of:
   (a) a polypeptide comprising the amino acid sequence of SEQ ID NO:5;
   (b) a polypeptide encoded by a nucleic acid molecule of SEQ ID NO:4; and
   (c) a derivative of the polypeptide of (a) or (b), wherein the derivative comprises one or more conservatively substituted amino acids and the derivative retains the function of the polypeptide, wherein the function is selected from the group consisting of ecdysone steroid receptor activity, ecdysone steroid receptor transactivation activity, ecdysone steroid receptor DNA binding activity, ecdysone steroid receptor hinge domain activity, and ecdysone receptor ligand binding activity.

3. The isolated polypeptide of claim 1, wherein the polypeptide is the *Heliothis virescens* ecdysone steroid receptor shown in SEQ ID NO:5.

4. The isolated polypeptide of claim 1, wherein the polypeptide is the transactivation domain of the *Heliothis virescens* ecdysone steroid receptor shown in amino acids 1–162 of SEQ ID NO:5.

5. The isolated polypeptide of claim 1, wherein the polypeptide is the DNA binding domain of the *Heliothis virescens* ecdysone steroid receptor shown in amino acids 163–228 of SEQ ID NO:5.

6. The isolated polypeptide of claim 1, wherein the polypeptide is the hinge domain of the *Heliothis virescens* ecdysone steroid receptor shown in amino acids 229–326 of SEQ ID NO:5.

7. The isolated polypeptide of claim 1, wherein the polypeptide is the ligand binding domain of the *Heliothis virescens* ecdysone receptor shown in amino acids 327–545 of SEQ ID NO:5.

* * * * *

SEQUENCE LISTING

```
<160> NUMBER OF SEQ ID NOS: 63

<210> SEQ ID NO 1
<211> LENGTH: 116
<212> TYPE: DNA
<213> ORGANISM: Heliothis virescens

<400> SEQUENCE: 1
tgcgaggggt gcaaggagtt cttcaggcgg agtgtaacca aaaatgcagt gtacatatgc     60
aaattcggcc atgcttgcga aatggatatg tatatgcgga gaaaatgcca agagta        116

<210> SEQ ID NO 2
<211> LENGTH: 1934
<212> TYPE: DNA
<213> ORGANISM: Heliothis virescens

<400> SEQUENCE: 2
tccactggtg ttttcaccac cacagaaaag gcctctgctc atttagaggg tggtgctaag     60
aaggtcatca tctcctgctg cccagcgctg acccatgttc gtcgttggtg tcaaccttga    120
agcagtatga cccctcttac aaggtcatct ccaacgcctc ctgcacaacc aactgcctcg    180
ctcctctcgc taaggtcatc catgacaact tcgagatcat tgaaggtctg atgaccactg    240
tacacgccac cactgccacc cagaagacag tggatggacc ctctggtaaa ctgtggcgtg    300
atggccgtgg tgctcagcag aatatcattc ccgcggaatt ccccagccgc agctagctaa    360
```

-continued

```
cctgcagcag acacaacccc taccttccat gccgttacca atgccaccga caacacccaa      420
atcagaaaac gagtcaatgt catcaggtcg tgaggaactg tctccagctt cgagtgtaaa      480
cggctgcagc acagatggcg aggcgaggcg gcagaagaaa ggcccagcgc cgaggcagca      540
agaagagcta tgtcttgtct gcggcgacag agcctccgga tatcactaca acgcgctcac      600
atgtgaaggg tgtaaaggtt tcttcaggcg gagtgtaacc aaaaatgcag tgtacatatg      660
caaattcggc catgcttgcg aaatggatat ctatatgcgg agaaaatgtc aggagtgtcg      720
gttgaagaaa tgtcttgcgg tgggcatgag gcccgagtgc gtggtgccgg agaaccagtg      780
tgcaatgaaa cggaaagaga aaaggcgca gagggaaaaa gacaaattgc ccgtcagtac      840
gacgacagta gacgatcaca tgcctcccat catgcaatgt gaccctccgc ccccagaggc      900
cgctagaatt ctggaatgtg tgcagcacga ggtggtgcca cgattcctga atgagaagct      960
aatggaacag aacagattga agaacgtgcc ccccctcact gccaatcaga agtcgttgat     1020
cgcaaggctc gtgtggtacc aggaaggcta tgaacaacct tccgaggaag acctgaagag     1080
ggttacacag tcggacgagg acgacgaaga ctcggatatg ccgttccgtc agattaccga     1140
gatgacgatt ctcacagtgc agctcatcgt agaattcgct aagggcctcc cgggcttcgc     1200
caagatctcg cagtcggacc agatcacgtt attaaaggcg tgctcaagtg aggtgatgat     1260
gctccgagtg gctcggcggt atgacgcggc caccgacagc gtactgttcg cgaacaacca     1320
ggcgtacact cgcgacaact accgcaaggc aggcatggcg tacgtcatcg aggacctgct     1380
gcacttctgt cggtgcatgt actccatgat gatggataac gtgcattatg cgctgcttac     1440
agccattgtc atcttctcag accggcccgg gcttgagcaa cccctgttgg tggaggacat     1500
ccagagatat tacctgaaca cgctacgggt gtacatcctg aaccagaaca gcgcgtcgcc     1560
ccgcggcgcc gtcatcttcg gcgagatcct gggcatactg acggagatcc gcacgctggg     1620
catgcagaac tccaacatgt gcatctccct caagctgaag aacaggaagc tgccgccgtt     1680
cctcgaggag atctgggacg tggcggacgt ggcgacgacg gcgacgccgg tggcggcgga     1740
ggcgccggcg cctctagccc ccgccccgcc cgcccggccg cccgccaccg tctagcgcgc     1800
ctcaggagag aacgctcata gactggctag ttttagtgaa gtgcacggac actgacgtcg     1860
acgtgatcaa cctatttata aggactgcga attttaccac ttaagagggc acaccgtac      1920 ccgatttcgt acgg                                                       1934
```

<210> SEQ ID NO 3
<211> LENGTH: 2464
<212> TYPE: DNA
<213> ORGANISM: Heliothis virescens
<220> FEATURE:
<221> NAME/KEY: misc
<222> LOCATION: (2241)..(2241)
<223> OTHER INFORMATION: n is a, c, g, or t

<400> SEQUENCE: 3

```
cgctggtata acaacggacc attccagacg ctgcgaatgc tcgaggagag ctcgtctgag       60
gtgacgtcgt cttcagcact gggcctgccg ccggctatgg tgatgtcccc ggaatcgctc      120
gcgtcgcccg agatcggcgg cctggagctg tggggctacg acgatggcat cacttacagc      180
atggcacagt cgctgggcac ctgcaccatg gagcagcagc agcccagcc gcagcagcag       240 ccgcagcaga cacaacccct accttccatg ccgttaccaa tgccaccgac aacacccaaa      300
tcagaaaacg agtcaatgtc atcaggtcgt gaggaactgt ctccagcttc gagtgtaaac      360
```

-continued

```
ggctgcagca cagatggcga ggcgaggcgg cagaagaaag gcccagcgcc gaggcagcaa    420
gaagagctat gtcttgtctg cggcgacaga gcctccggat atcactacaa cgcgctcaca    480
tgtgaagggt gtaaaggttt cttcaggcgg agtgtaacca aaaatgcagt gtacatatgc    540
aaattcggcc atgcttgcga atggatatc tatatgcgga gaaaatgtca ggagtgtcgg    600
ttgaagaaat gtcttgcggt gggcatgagg cccgagtgcg tggtgccgga gaaccagtgt    660
gcaatgaaac ggaaagagaa aaaggcgcag agggaaaaag acaaattgcc cgtcagtacg    720
acgacagtag acgatcacat gcctcccatc atgcaatgtg accctccgcc cccagaggcc    780
gctagaattc tggaatgtgt gcagcacgag gtggtgccac gattcctgaa tgagaagcta    840
atggaacaga acagattgaa gaacgtgccc cccctcactg ccaatcagaa gtcgttgatc    900
gcaaggctcg tgtggtacca ggaaggctat gaacaacctt ccgaggaaga cctgaagagg    960
gttacacagt cggacgagga cgacgaagac tcggatatgc cgttccgtca gattaccgag   1020
atgacgattc tcacagtgca gctcatcgta gaattcgcta agggcctccc gggcttcgcc   1080
aagatctcgc agtcggacca gatcacgtta ttaaaggcgt gctcaagtga ggtgatgatg   1140
ctccgagtgg ctcggcggta tgacgcggcc accgacagcg tactgttcgc gaacaaccag   1200
gcgtacactc gcgacaacta ccgcaaggca ggcatggcgt acgtcatcga ggacctgctg   1260
cacttctgtc ggtgcatgta ctccatgatg atggataacg tgcattatgc gctgcttaca   1320
gccattgtca tcttctcaga ccggcccggg cttgagcaac ccctgttggt ggaggacatc   1380
cagagatatt acctgaacac gctacgggtg tacatcctga accagaacag cgcgtcgccc   1440
cgcggcgccg tcatcttcgg cgagatcctg gcatactga cggagatccg cacgctgggc   1500
atgcagaact ccaacatgtg catctccctc aagctgaaga caggaagct gccgccgttc   1560
ctcgaggaga tctgggacgt ggcggacgtg gcgacgacgg cgacgccggt ggcggcggag   1620
gcgccggcgc ctctagcccc cgccccgccc gcccggccgc cgccaccgt ctagcgcgcc   1680
tcaggagaga acgctcatag actggctagt tttagtgaag tgcacggaca ctgacgtcga   1740
cgtgatcaac ctatttataa ggactgcgaa ttttaccact taagagggca cacccgtacc   1800
cgatttcgta cgtattcggt gaccgacgac gatgcagagc gtgtgtaatg tgaatatatg   1860
tgttgttgaa cgatttggag aatatatatt ggtgttgctg ttcgggcccg cacgccgtcg   1920
ccggtcggcg gcgatcgcgg cgcccgcggc ttcagttttta tttcgtttac gactgagttg   1980
gtcactcgga tacgactgta tgataagact tcgttcgata agtacaccta ctaaattaca   2040
catacgtacg tagcttacga gagttattag agacaaagaa tataagaaga agatgtttct   2100
attgggtgaa aagttgatag ttatgtttat ttaccaaaat taacaataat acgttgatta   2160
acctttcgag tataatattg tgatgagtcg tccgctgtcc acgtcgccgt cacatgtttg   2220
tttctgatgc acacgtgagg ngcgttatcg tgtttcatgg ttccatcgtc ctgtgcccgc   2280
gaccctcgac taaatgagta atttaattta ttgctgtgat tacatttta tgtgttgatt   2340
atctaccata gggtgatata agtgtgtctt attacaatac aaagtgtgtg tcgtcgatag   2400
cttccacacg agcaagcctt tgtttaagt gatttactga catggacact cgacccggaa   2460
cttc                                                               2464
```

<210> SEQ ID NO 4
<211> LENGTH: 2745
<212> TYPE: DNA
<213> ORGANISM: Heliothis virescens
<220> FEATURE:
<221> NAME/KEY: misc
<222> LOCATION: (2522)..(2522)
<223> OTHER INFORMATION: n=a, c, g, or t

<400> SEQUENCE: 4

| | | | | | |
|---|---|---|---|---|---|
| actcgcgtgc | tcttctcacc | tgttgctcgg | attgtgttgt | actagaaaaa | agttgtcgcc | 60 |
| gctcgaacga | gacttccgag | tcctattgga | ttgcacgaaa | gtcgagacag | tggatagcga | 120 |
| ttcggtttcg | tttgaacgtt | gcgtagacga | gtggtgcatg | tccatgagtc | gcgtttagat | 180 |
| agtttagtgc | gaggaaaaag | tgaagtgaaa | gccttcctcg | gaggatgtcc | ctcggcgctc | 240 |
| gtggataccg | gaggtgtgac | acgctcgccg | acatgagacg | ccgctggtat | aacaacggac | 300 |
| cattccagac | gctgcgaatg | ctcgaggaga | gctcgtctga | ggtgacgtcg | tcttcagcac | 360 |
| tgggcctgcc | gccggctatg | gtgatgtccc | cggaatcgct | cgcgtcgccc | gagatcggcg | 420 |
| gcctggagct | gtggggctac | gacgatggca | tcacttacag | catggcacag | tcgctgggca | 480 |
| cctgcaccat | ggagcagcag | cagccccagc | cgcagcagca | gccgcagcag | acacaacccc | 540 |
| taccttccat | gccgttacca | atgccaccga | caacacccaa | atcagaaaac | gagtcaatgt | 600 |
| catcaggtcg | tgaggaactg | tctccagctt | cgagtgtaaa | cggctgcagc | acagatggcg | 660 |
| aggcgaggcg | gcagaagaaa | ggcccagcgc | cgaggcagca | agaagagcta | tgtcttgtct | 720 |
| gcggcgacag | agcctccgga | tatcactaca | acgcgctcac | atgtgaaggg | tgtaaaggtt | 780 |
| tcttcaggcg | gagtgtaacc | aaaaatgcag | tgtacatatg | caaattcggc | catgcttgcg | 840 |
| aaatggatat | ctatatgcgg | agaaaatgtc | aggagtgtcg | gttgaagaaa | tgtcttgcgg | 900 |
| tgggcatgag | gcccgagtgc | gtggtgccgg | agaaccagtg | tgcaatgaaa | cggaaagaga | 960 |
| aaaaggcgca | gagggaaaaa | gacaaattgc | ccgtcagtac | gacgacagta | gacgatcaca | 1020 |
| tgcctcccat | catgcaatgt | gaccctccgc | ccccagaggc | cgctagaatt | ctggaatgtg | 1080 |
| tgcagcacga | ggtggtgcca | cgattcctga | atgagaagct | aatggaacag | aacagattga | 1140 |
| agaacgtgcc | cccctcact | gccaatcaga | agtcgttgat | cgcaaggctc | gtgtggtacc | 1200 |
| aggaaggcta | tgaacaacct | tccgaggaag | acctgaagag | ggttacacag | tcggacgagg | 1260 |
| acgacgaaga | ctcggatatg | ccgttccgtc | agattaccga | gatgacgatt | ctcacagtgc | 1320 |
| agctcatcgt | agaattcgct | aagggcctcc | cgggcttcgc | caagatctcg | cagtcggacc | 1380 |
| agatcacgtt | attaaaggcg | tgctcaagtg | aggtgatgat | gctccgagtg | gctcggcggt | 1440 |
| atgacgcggc | caccgacagc | gtactgttcg | cgaacaacca | ggcgtacact | cgcgacaact | 1500 |
| accgcaaggc | aggcatggcg | tacgtcatcg | aggacctgct | gcacttctgt | cggtgcatgt | 1560 |
| actccatgat | gatggataac | gtgcattatg | cgctgcttac | agccattgtc | atcttctcag | 1620 |
| accggcccgg | gcttgagcaa | cccctgttgg | tggaggagat | ccagagatat | tacctgaaca | 1680 |
| cgctacgggt | gtacatcctg | aaccagaaca | gcgcgtcgcc | ccgcggcgcc | gtcatcttcg | 1740 |
| gcgagatcct | gggcatactg | acggagatcc | gcacgctggg | catgcagaac | tccaacatgt | 1800 |
| gcatctccct | caagctgaag | aacaggaagc | tgccgccgtt | cctcgaggag | atctgggacg | 1860 |
| tggcggacgt | ggcgacgacg | gcgacgccgg | tggcggcgga | ggcgccggcg | cctctagccc | 1920 |
| ccgccccgcc | cgcccggccg | cccgccaccg | tctagcgcgc | tcaggagag | aacgctcata | 1980 |
| gactggctag | ttttagtgaa | gtgcacggac | actgacgtcg | acgtgatcaa | cctatttata | 2040 |
| aggactgcga | attttaccac | ttaagagggc | acaccgtac | ccgatttcgt | acgtattcgg | 2100 |
| tgaccgacga | cgatgcagag | cgtgtgtaat | gtgaatatat | gtgttgttga | acgatttgga | 2160 |
| gaatatatat | tggtgttgct | gttcgggccc | gcacgccgtc | gccggtcggc | ggcgatcgcg | 2220 |

```
gcgcccgcgg cttcagtttt atttcgttta cgactgagtt ggtcactcgg atacgactgt    2280
atgataagac ttcgttcgat aagtacacct actaaattac acatacgtac gtagcttacg    2340
agagttatta gagacaaaga atataagaag aagatgtttc tattgggtga aaagttgata    2400
gttatgttta tttaccaaaa ttaacaataa tacgttgatt aacctttcga gtataatatt    2460
gtgatgagtc gtccgctgtc cacgtcgccg tcacatgttt gtttctgatg cacacgtgag    2520
gngcgttatc gtgtttcatg gttccatcgt cctgtgcccg cgaccctcga ctaaatgagt    2580
aatttaattt attgctgtga ttacatttta atgtgttgat tatctaccat agggtgatat    2640
aagtgtgtct tattacaata caaagtgtgt gtcgtcgata gcttccacac gagcaagcct    2700
tttgtttaag tgatttactg acatggacac tcgacccgga acttc                   2745
```

<210> SEQ ID NO 5
<211> LENGTH: 575
<212> TYPE: PRT
<213> ORGANISM: Heliothis virescens

<400> SEQUENCE: 5

```
Met Ser Leu Gly Ala Arg Gly Tyr Arg Arg Cys Asp Thr Leu Ala Asp
1               5                   10                  15

Met Arg Arg Arg Trp Tyr Asn Asn Gly Gly Phe Gln Thr Leu Arg Met
            20                  25                  30

Leu Glu Glu Ser Ser Ser Glu Val Thr Ser Ser Ser Ala Leu Gly Leu
        35                  40                  45

Pro Pro Ala Met Val Met Ser Pro Glu Ser Leu Ala Ser Pro Glu Ile
    50                  55                  60

Gly Gly Leu Glu Leu Trp Gly Tyr Asp Asp Gly Ile Thr Tyr Ser Met
65                  70                  75                  80

Ala Gln Ser Leu Gly Thr Cys Thr Met Glu Gln Gln Gln Pro Gln Pro
                85                  90                  95

Gln Gln Gln Pro Gln Gln Thr Gln Pro Leu Pro Ser Met Pro Leu Pro
            100                 105                 110

Met Pro Thr Thr Pro Lys Ser Glu Asn Glu Ser Met Ser Ser Ser Gly
        115                 120                 125

Arg Glu Glu Leu Ser Pro Ala Ser Ser Val Asn Gly Cys Ser Thr Asp
    130                 135                 140

Gly Glu Ala Arg Arg Gln Lys Lys Gly Pro Ala Pro Arg Gln Gln Glu
145                 150                 155                 160

Glu Leu Cys Leu Val Cys Gly Asp Arg Ala Ser Gly Tyr His Tyr Asn
                165                 170                 175

Ala Leu Thr Cys Glu Gly Cys Lys Gly Phe Phe Arg Arg Ser Val Thr
            180                 185                 190

Lys Asn Ala Val Tyr Ile Cys Lys Phe Gly His Ala Cys Glu Met Asp
        195                 200                 205

Ile Tyr Met Arg Arg Lys Cys Gln Glu Cys Arg Leu Lys Lys Cys Leu
    210                 215                 220

Ala Val Gly Met Arg Pro Glu Cys Val Val Pro Glu Asn Gln Cys Ala
225                 230                 235                 240

Met Lys Arg Lys Glu Lys Lys Ala Gln Arg Glu Lys Asp Lys Leu Pro
                245                 250                 255

Val Ser Thr Thr Thr Val Asp Asp His Met Pro Pro Ile Met Gln Cys
            260                 265                 270

Asp Pro Pro Pro Glu Ala Ala Arg Ile Leu Glu Cys Val Gln His
        275                 280                 285
```

```
Glu Val Val Pro Arg Phe Leu Asn Glu Lys Leu Met Glu Gln Asn Arg
    290                 295                 300
Leu Lys Asn Val Pro Pro Leu Thr Ala Asn Gln Lys Ser Leu Ile Ala
305                 310                 315                 320
Arg Leu Val Trp Tyr Gln Glu Gly Tyr Glu Gln Pro Ser Glu Asp
            325                 330                 335
Leu Lys Arg Val Thr Gln Ser Asp Glu Asp Glu Asp Ser Asp Met
            340                 345                 350
Pro Phe Arg Gln Ile Thr Glu Met Thr Ile Leu Thr Val Gln Leu Ile
            355                 360                 365
Val Glu Phe Ala Lys Gly Leu Pro Gly Phe Ala Lys Ile Ser Gln Ser
    370                 375                 380
Asp Gln Ile Thr Leu Leu Lys Ala Cys Ser Ser Glu Val Met Met Leu
385                 390                 395                 400
Arg Val Ala Arg Arg Tyr Asp Ala Ala Thr Asp Ser Val Leu Phe Ala
                405                 410                 415
Asn Asn Gln Ala Tyr Thr Arg Asp Asn Tyr Arg Lys Ala Gly Met Ala
            420                 425                 430
Tyr Val Ile Glu Asp Leu Leu His Phe Cys Arg Cys Met Tyr Ser Met
            435                 440                 445
Met Met Asp Asn Val His Tyr Ala Leu Leu Thr Ala Ile Val Ile Phe
    450                 455                 460
Ser Asp Arg Pro Gly Leu Glu Gln Pro Leu Leu Val Glu Asp Ile Gln
465                 470                 475                 480
Arg Tyr Tyr Leu Asn Thr Leu Arg Val Tyr Ile Leu Asn Gln Asn Ser
                485                 490                 495
Ala Ser Pro Arg Gly Ala Val Ile Phe Gly Glu Ile Leu Gly Ile Leu
            500                 505                 510
Thr Glu Ile Arg Thr Leu Gly Met Gln Asn Ser Asn Met Cys Ile Ser
            515                 520                 525
Leu Lys Leu Lys Lys Arg Lys Leu Pro Pro Phe Leu Glu Glu Ile Trp
    530                 535                 540
Asp Val Ala Asp Val Ala Thr Thr Ala Thr Pro Val Ala Ala Glu Ala
545                 550                 555                 560
Pro Ala Pro Leu Ala Pro Ala Pro Pro Ala Arg Pro Ala Thr Val
                565                 570                 575

<210> SEQ ID NO 6
<211> LENGTH: 948
<212> TYPE: DNA
<213> ORGANISM: Spodoptera exigua

<400> SEQUENCE: 6
aggccggagt gcgtggtgcc agaaaaccag tgtgcaatga aaggaaaga gaaaaggca       60 caaagggaaa aagacaagtt gccagtcagt acaacgacag tggatgatca catgcctccc     120
attatgcagt gtgatccacc gcctccagag gccgcaagaa ttcacgaggt ggtgccacga     180
ttcctgaatg aaaagctaat ggacaggaca aggctcaaga atgtgccccc tcactgccaa     240
ccagaagtcc ttaatagcga ggctggtctg gtaccaagaa ggctatgaac agccatcaga     300
agaggatcta aaaagagtca cacagtcgga tgaagacgaa gaagagtcgg acatgccgtt     360
ccgtcagatc accgagatga cgatcctcac agtgcagctc attgttgaat tcgctaaggg     420
cctaccagcg ttcgcaaaga tctcacagtc ggatcagatc acattattaa aggcctgttc     480
```

-continued

```
gagtgaggtg atgatgttgc gagtagctcg gcggtacgac gcggcgacag acagcgtgtt    540
gttcgccaac aaccaggcgt acacccgcga caactaccgc aaggcaggca tggcctacgt    600
catcgaggac ctgctgcact tctgccggtg catgtactcc atgatgatgg ataacgtcca    660
ctatgcactg ctcactgcca tcgtcatttt ctcagaccga cccgggcttg agctaaccct    720
gttggtggag gagatccaga gatattacct gaacacgctg cgggtgtaca tcctgaacca    780
gaacagtcgg tcgccgtgct gccctgtcat ctacgctaag atcctcggca tcctgacgga    840
gctgcggacc ctgggcatgc agaactccaa catgtgcatc tcactcaagc tgaagaacag    900
gaacgtgccg ccgttcttcg aggatatctg ggacgtcctc gagtaaaa                 948
```

<210> SEQ ID NO 7
<211> LENGTH: 314
<212> TYPE: PRT
<213> ORGANISM: Spodoptera exigua

<400> SEQUENCE: 7

```
Arg Pro Glu Cys Val Val Pro Glu Asn Gln Cys Ala Met Lys Arg Lys
  1               5                  10                  15

Glu Lys Lys Ala Gln Arg Glu Lys Asp Lys Leu Pro Val Ser Thr Thr
             20                  25                  30

Thr Val Asp Asp His Met Pro Pro Ile Met Gln Cys Asp Pro Pro Pro
         35                  40                  45

Pro Glu Ala Ala Arg Ile His Glu Val Val Pro Arg Phe Leu Asn Glu
     50                  55                  60

Lys Leu Met Glu Arg Thr Arg Leu Arg Asn Val Pro Pro Leu Thr Ala
 65                  70                  75                  80

Asn Gln Lys Ser Leu Ile Ala Arg Leu Val Trp Tyr Gln Glu Gly Tyr
                 85                  90                  95

Glu Gln Pro Ser Glu Glu Asp Leu Lys Arg Val Thr Gln Ser Asp Glu
            100                 105                 110

Asp Glu Glu Glu Ser Asp Met Pro Phe Arg Gln Ile Thr Glu Met Thr
        115                 120                 125

Ile Leu Thr Val Gln Leu Ile Val Glu Phe Ala Lys Gly Leu Pro Ala
    130                 135                 140

Phe Ala Lys Ile Ser Gln Ser Asp Gln Ile Thr Leu Leu Lys Ala Cys
145                 150                 155                 160

Ser Ser Glu Val Met Met Leu Arg Val Ala Arg Arg Tyr Asp Ala Ala
                165                 170                 175

Thr Asp Ser Val Leu Phe Ala Asn Asn Gln Ala Tyr Thr Arg Asp Asn
            180                 185                 190

Tyr Arg Lys Ala Gly Met Ala Tyr Val Ile Glu Asp Leu Leu His Phe
        195                 200                 205

Cys Arg Cys Met Tyr Ser Met Met Met Asp Asn Val His Tyr Ala Leu
    210                 215                 220

Leu Thr Ala Ile Val Ile Phe Ser Asp Arg Pro Gly Leu Glu Leu Thr
225                 230                 235                 240

Leu Leu Val Glu Glu Ile Gln Arg Tyr Tyr Leu Asn Thr Leu Arg Val
                245                 250                 255

Tyr Ile Leu Asn Gln Asn Ser Arg Ser Pro Cys Cys Pro Val Ile Tyr
            260                 265                 270

Ala Lys Ile Leu Gly Ile Leu Thr Glu Leu Arg Thr Leu Gly Met Gln
        275                 280                 285

Asn Ser Asn Met Cys Ile Ser Leu Lys Leu Lys Asn Arg Asn Val Pro
```

```
                290                 295                 300

Pro Phe Phe Glu Asp Ile Asp Trp Asp Val
305                 310
```

<210> SEQ ID NO 8
<211> LENGTH: 878
<212> TYPE: PRT
<213> ORGANISM: Drosophila melanogaster

<400> SEQUENCE: 8

```
Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
                20                  25                  30

Ser Gly Val Asn Met Ser Pro Ser Ser Leu Asp Ser His Asp Tyr Cys
            35                  40                  45

Asp Asn Asp Lys Trp Leu Cys Gly Asn Glu Ser Gly Ser Phe Gly Gly
        50                  55                  60

Ser Asn Gly His Gly Leu Ser Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Gly Ser Thr Asn Gly Gln
            100                 105                 110

Tyr Val Pro Gly Ala Thr Asn Leu Gly Ala Leu Ala Asn Gly Met Leu
        115                 120                 125

Asn Gly Gly Phe Asn Gly Met Gln Gln Gln Ile Gln Asn Gly His Gly
130                 135                 140

Leu Ile Asn Ser Thr Thr Pro Ser Thr Pro Thr Thr Pro Leu His Leu
145                 150                 155                 160

Gln Gln Asn Leu Gly Gly Ala Gly Gly Gly Ile Gly Gly Met Gly
                165                 170                 175

Ile Leu His His Ala Asn Gly Thr Pro Asn Gly Leu Ile Gly Val Val
            180                 185                 190

Gly Gly Gly Gly Gly Val Gly Leu Gly Val Gly Gly Gly Val Gly
        195                 200                 205

Gly Leu Gly Met Gln His Thr Pro Arg Ser Asp Ser Val Asn Ser Ile
210                 215                 220

Ser Ser Gly Arg Asp Asp Leu Ser Pro Ser Ser Leu Asn Gly Tyr
225                 230                 235                 240

Ser Ala Asn Glu Ser Cys Asp Ala Lys Lys Ser Lys Lys Gly Pro Ala
                245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
        275                 280                 285

Arg Arg Ser Val Thr Lys Ser Ala Val Tyr Cys Cys Lys Phe Gly Arg
290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Met Arg Pro Gly Cys Val Val Pro
                325                 330                 335

Gly Asn Gln Cys Ala Met Lys Arg Arg Glu Lys Lys Ala Gln Lys Glu
            340                 345                 350
```

-continued

```
Lys Asp Lys Met Thr Thr Ser Pro Ser Ser Gln His Gly Gly Asn Gly
        355                 360                 365

Ser Leu Ala Ser Gly Gly Gln Asp Phe Val Lys Lys Glu Ile Leu
    370                 375                 380

Asp Leu Met Thr Cys Glu Pro Pro Gln His Ala Thr Ile Pro Leu Leu
385                 390                 395                 400

Pro Asp Glu Ile Leu Ala Lys Cys Gln Ala Arg Asn Ile Pro Ser Leu
                405                 410                 415

Thr Tyr Asn Gln Leu Ala Val Ile Thr Lys Leu Ile Trp Tyr Gln Asp
            420                 425                 430

Gly Tyr Glu Gln Pro Ser Glu Glu Asp Leu Arg Arg Ile Met Ser Gln
        435                 440                 445

Pro Asp Glu Asn Glu Ser Gln Thr Asp Val Ser Phe Arg His Ile Thr
    450                 455                 460

Glu Ile Thr Ile Leu Thr Val Gln Leu Ile Val Glu Phe Ala Lys Gly
465                 470                 475                 480

Leu Pro Ala Phe Thr Lys Ile Pro Gln Glu Asp Gln Ile Thr Leu Leu
                485                 490                 495

Lys Ala Cys Ser Ser Glu Val Met Met Leu Arg Met Ala Arg Arg Tyr
            500                 505                 510

Asp His Ser Ser Asp Ser Ile Phe Phe Ala Asn Asn Arg Ser Tyr Thr
        515                 520                 525

Arg Asp Ser Tyr Lys Met Ala Gly Met Ala Asp Asn Ile Glu Asp Leu
    530                 535                 540

Leu His Phe Cys Arg Gln Met Phe Ser Met Lys Val Asp Asn Val Glu
545                 550                 555                 560

Tyr Ala Leu Leu Thr Ala Ile Val Ile Phe Ser Asp Arg Pro Gly Leu
                565                 570                 575

Glu Lys Ala Gln Leu Val Glu Ala Ile Gln Ser Tyr Tyr Ile Asp Thr
            580                 585                 590

Leu Arg Ile Thr Ile Leu Asn Arg His Cys Gly Asp Ser Met Ser Leu
        595                 600                 605

Val Phe Tyr Ala Lys Leu Leu Ser Ile Leu Thr Glu Leu Arg Thr Leu
    610                 615                 620

Gly Asn Gln Asn Ala Glu Met Cys Phe Ser Leu Lys Leu Lys Asn Arg
625                 630                 635                 640

Lys Leu Pro Lys Phe Leu Glu Glu Ile Trp Asp Val His Ala Ile Pro
                645                 650                 655

Pro Ser Val Gln Ser His Leu Gln Ile Thr Gln Glu Glu Asp Glu Arg
            660                 665                 670

Leu Glu Arg Ala Glu Arg Met Arg Ala Ser Val Gly Gly Ala Ile Thr
        675                 680                 685

Ala Gly Ile Asp Cys Asp Ser Ala Ser Thr Ser Ala Ala Ala Ala Ala
    690                 695                 700

Ala Gln His Gln Pro Gln Pro Gln Pro Gln Pro Gln Pro Ser Ser Leu
705                 710                 715                 720

Thr Gln Asn Asp Ser Gln His Gln Thr Gln Pro Gln Leu Gln Pro Gln
                725                 730                 735

Leu Pro Pro Gln Leu Gln Gly Gln Leu Gln Pro Gln Leu Gln Pro Gln
            740                 745                 750

Leu Gln Thr Gln Leu Gln Pro Gln Ile Gln Pro Gln Pro Gln Leu Leu
        755                 760                 765

Pro Val Ser Ala Pro Val Pro Ala Ser Val Thr Ala Pro Gly Ser Leu
```

-continued

```
                770                 775                 780
Ser Ala Val Ser Thr Ser Glu Tyr Met Gly Gly Ser Ala Ala Ile
785                 790                 795                 800

Gly Pro Ile Thr Pro Ala Thr Ser Ser Ile Thr Ala Ala Val Thr
                805                 810                 815

Ala Ser Ser Thr Thr Ser Ala Val Pro Met Gly Asn Gly Val Gly Val
                820                 825                 830

Gly Val Gly Val Gly Gly Asn Val Ser Met Tyr Ala Asn Ala Gln Thr
                835                 840                 845

Ala Met Ala Leu Met Gly Val Ala Leu His Ser His Gln Gln Gln Leu
    850                 855                 860

Ile Gly Gly Val Ala Val Lys Ser Glu His Ser Thr Thr Ala
865                 870                 875
```

<210> SEQ ID NO 9
<211> LENGTH: 536
<212> TYPE: PRT
<213> ORGANISM: Chironomus tentans

<400> SEQUENCE: 9

```
Met Lys Thr Glu Asn Leu Ile Val Thr Thr Val Lys Val Glu Pro Leu
1               5                   10                  15

Asn Tyr Ala Ser Gln Ser Phe Gly Asp Asn Asn Ile Tyr Gly Gly Ala
                20                  25                  30

Thr Lys Lys Gln Arg Leu Glu Ser Asp Glu Thr Met Asn His Asn Gln
            35                  40                  45

Thr Asn Met Asn Leu Glu Ser Ser Asn Met Asn His Asn Thr Ile Ser
    50                  55                  60

Gly Phe Ser Ser Pro Asp Val Asn Tyr Glu Ala Tyr Ser Pro Asn Ser
65                  70                  75                  80

Lys Leu Asp Asp Gly Asn Met Ser Val His Met Gly Asp Gly Leu Asp
                85                  90                  95

Gly Lys Lys Ser Ser Lys Lys Gly Pro Val Pro Arg Gln Gln Glu
            100                 105                 110

Glu Leu Cys Leu Val Cys Gly Asp Arg Ala Ser Gly Tyr His Tyr Asn
        115                 120                 125

Ala Leu Thr Cys Glu Gly Cys Lys Gly Phe Phe Arg Arg Ser Val Thr
    130                 135                 140

Lys Asn Ala Val Tyr Cys Cys Lys Phe Gly His Glu Cys Glu Met Asp
145                 150                 155                 160

Met Tyr Met Arg Arg Lys Cys Gln Glu Cys Arg Leu Lys Lys Cys Leu
                165                 170                 175

Ala Val Gly Met Arg Pro Glu Cys Val Val Pro Glu Asn Gln Cys Ala
            180                 185                 190

Ile Lys Arg Lys Glu Lys Lys Ala Gln Lys Glu Lys Asp Lys Val Pro
        195                 200                 205

Gly Ile Val Gly Ser Asn Thr Ser Ser Ser Leu Leu Asn Gln Ser
    210                 215                 220

Leu Asn Asn Gly Ser Leu Lys Asn Leu Glu Ile Ser Tyr Arg Glu Glu
225                 230                 235                 240

Leu Leu Gln Gln Leu Met Lys Cys Asp Pro Pro His Pro Met Gln
                245                 250                 255

Gln Leu Leu Pro Glu Lys Leu Leu Met Glu Asn Arg Ala Lys Gly Thr
            260                 265                 270
```

-continued

```
Pro Gln Leu Thr Ala Asn Gln Val Ala Val Ile Tyr Lys Leu Ile Trp
        275                 280                 285

Tyr Gln Asp Gly Tyr Glu Gln Pro Ser Glu Glu Asp Leu Lys Arg Ile
    290                 295                 300

Thr Glu Leu Glu Glu Glu Asp Gln Glu His Glu Ala Asn Phe
305                 310                 315                 320

Arg Tyr Ile Thr Glu Val Thr Ile Leu Thr Val Gln Leu Ile Val Glu
                325                 330                 335

Phe Ala Lys Gly Leu Pro Ala Phe Ile Lys Ile Pro Gln Glu Asp Gln
                340                 345                 350

Ile Thr Leu Leu Lys Ala Cys Ser Ser Glu Val Met Met Leu Arg Met
            355                 360                 365

Ala Arg Arg Tyr Asp His Asp Ser Asp Ser Ile Leu Phe Ala Asn Asn
        370                 375                 380

Thr Ala Tyr Thr Lys Gln Thr Tyr Gln Leu Ala Gly Met Glu Glu Thr
385                 390                 395                 400

Ile Asp Asp Leu Leu His Phe Cys Arg Gln Met Tyr Ala Leu Ser Ile
                405                 410                 415

Asp Asn Val Glu Thr Ala Leu Leu Thr Ala Ile Val Ile Phe Ser Asp
                420                 425                 430

Arg Pro Gly Leu Glu Lys Ala Glu Met Val Asp Ile Ile Gln Ser Tyr
            435                 440                 445

Tyr Thr Glu Thr Leu Lys Val Tyr Ile Val Arg Asp His Gly Gly Glu
    450                 455                 460

Ser Arg Cys Ser Val Gln Phe Ala Lys Leu Leu Gly Ile Leu Thr Glu
465                 470                 475                 480

Leu Arg Thr Met Gly Asn Leu Asn Ser Glu Met Cys Phe Ser Leu Lys
                485                 490                 495

Leu Arg Asn Arg Lys Leu Pro Arg Phe Leu Glu Glu Val Trp Asp Val
            500                 505                 510

Gly Asp Val Asn Asn Gln Thr Thr Ala Thr Thr Asn Thr Glu Asn Ile
        515                 520                 525

Val Arg Glu Arg Ile Asn Arg Asn
    530                 535
```

<210> SEQ ID NO 10
<211> LENGTH: 606
<212> TYPE: PRT
<213> ORGANISM: Bombyx mori

<400> SEQUENCE: 10

```
Met Arg Val Glu Asn Val Asp Asn Val Ser Phe Ala Leu Asn Gly Arg
1               5                   10                  15

Ala Asp Glu Trp Cys Met Ser Val Glu Thr Arg Leu Asp Ser Leu Val
            20                  25                  30

Arg Glu Lys Ser Glu Val Lys Ala Tyr Val Gly Gly Cys Pro Ser Val
        35                  40                  45

Ile Thr Asp Ala Gly Ala Tyr Asp Ala Leu Phe Asp Met Arg Arg Arg
    50                  55                  60

Trp Ser Asn Asn Gly Gly Phe Pro Leu Arg Met Leu Glu Glu Ser Ser
65                  70                  75                  80

Ser Glu Val Thr Ser Ser Ser Ala Leu Gly Leu Pro Pro Ala Met Val
                85                  90                  95

Met Ser Pro Glu Ser Leu Ala Ser Pro Glu Tyr Gly Ala Leu Glu Leu
                100                 105                 110
```

-continued

```
Trp Ser Tyr Asp Asp Gly Ile Thr Tyr Asn Thr Ala Gln Ser Leu Leu
        115                 120                 125

Gly Ala Cys Asn Met Gln Gln Gln Leu Gln Pro Gln Gln Pro His
130                 135                 140

Pro Ala Pro Thr Leu Pro Thr Met Pro Leu Pro Met Pro Pro Thr
145                 150                 155                 160

Thr Pro Lys Ser Glu Asn Glu Ser Met Ser Ser Gly Arg Glu Glu Leu
        165                 170                 175

Ser Pro Ala Ser Ser Ile Asn Gly Cys Ser Ala Asp Ala Asp Ala Arg
            180                 185                 190

Arg Gln Lys Lys Gly Pro Ala Pro Arg Gln Gln Glu Glu Leu Cys Leu
        195                 200                 205

Val Cys Gly Asp Arg Ala Ser Gly Tyr His Tyr Asn Ala Leu Thr Cys
210                 215                 220

Glu Gly Cys Lys Gly Phe Phe Arg Arg Ser Val Thr Lys Asn Ala Val
225                 230                 235                 240

Tyr Ile Cys Lys Phe Gly His Ala Cys Glu Met Asp Met Tyr Met Arg
            245                 250                 255

Arg Lys Cys Gln Glu Cys Arg Leu Lys Lys Cys Leu Ala Val Gly Met
        260                 265                 270

Arg Pro Glu Cys Val Ile Gln Glu Pro Ser Lys Asn Lys Asp Arg Gln
        275                 280                 285

Arg Gln Lys Lys Asp Lys Gly Ile Leu Leu Pro Val Ser Thr Thr Thr
        290                 295                 300

Val Glu Asp His Met Pro Pro Ile Met Gln Cys Asp Pro Pro Pro Pro
305                 310                 315                 320

Glu Ala Ala Arg Ile His Glu Val Val Pro Arg Tyr Leu Ser Glu Lys
                325                 330                 335

Leu Met Glu Gln Asn Arg Gln Lys Asn Ile Pro Pro Leu Ser Ala Asn
            340                 345                 350

Gln Lys Ser Leu Ile Ala Arg Leu Val Trp Tyr Gln Glu Gly Tyr Glu
        355                 360                 365

Gln Pro Ser Asp Glu Asp Leu Lys Arg Val Thr Gln Thr Trp Gln Ser
370                 375                 380

Asp Glu Glu Asp Glu Glu Ser Asp Leu Pro Phe Arg Gln Ile Thr Glu
385                 390                 395                 400

Met Thr Ile Leu Thr Val Gln Leu Ile Val Glu Phe Ala Lys Gly Leu
                405                 410                 415

Pro Gly Phe Ser Lys Ile Ser Gln Ser Asp Gln Ile Thr Leu Leu Lys
            420                 425                 430

Ala Ser Ser Ser Glu Val Met Met Leu Arg Val Ala Arg Arg Tyr Asp
        435                 440                 445

Ala Ala Ser Asp Ser Val Leu Phe Ala Asn Asn Lys Ala Tyr Thr Arg
        450                 455                 460

Asp Asn Tyr Arg Gln Gly Gly Met Ala Tyr Val Ile Glu Asp Leu Leu
465                 470                 475                 480

His Phe Cys Arg Cys Met Phe Ala Met Gly Met Asp Asn Val His Phe
            485                 490                 495

Ala Leu Leu Thr Ala Ile Val Ile Phe Ser Asp Arg Pro Gly Leu Glu
            500                 505                 510

Gln Pro Ser Leu Val Glu Glu Ile Gln Arg Tyr Tyr Leu Asn Thr Leu
        515                 520                 525
```

```
Arg Ile Tyr Ile Ile Asn Gln Asn Ser Ala Ser Ser Arg Cys Ala Val
            530                 535                 540

Ile Tyr Gly Arg Ile Leu Ser Val Leu Thr Glu Leu Arg Thr Leu Gly
545                 550                 555                 560

Thr Gln Asn Ser Asn Met Cys Ile Ser Leu Lys Leu Lys Asn Arg Lys
                565                 570                 575

Leu Pro Pro Phe Leu Glu Glu Ile Trp Asp Val Ala Glu Val Ala Arg
            580                 585                 590

Arg His Pro Thr Val Leu Pro Pro Thr Asn Pro Val Val Leu
            595                 600                 605

<210> SEQ ID NO 11
<211> LENGTH: 556
<212> TYPE: PRT
<213> ORGANISM: Manduca sexta

<400> SEQUENCE: 11

Met Arg Arg Arg Trp Ser Asn Asn Gly Cys Phe Pro Leu Arg Met Phe
1               5                   10                  15

Glu Glu Ser Ser Ser Glu Val Thr Ser Ser Ser Ala Phe Gly Met Pro
            20                  25                  30

Ala Ala Met Val Met Ser Pro Glu Ser Leu Ala Ser Pro Glu Tyr Gly
            35                  40                  45

Gly Leu Glu Leu Trp Ser Tyr Asp Glu Thr Met Thr Asn Tyr Pro Ala
50                  55                  60

Gln Ser Leu Leu Gly Ala Cys Asn Ala Pro Gln Gln Gln Gln Gln Gln
65                  70                  75                  80

Gln Gln Gln Gln Pro Ser Ala Gln Pro Leu Pro Ser Met Pro Leu Pro
            85                  90                  95

Met Pro Pro Thr Thr Pro Lys Ser Glu Asn Glu Ser Met Ser Ser Gly
            100                 105                 110

Arg Glu Glu Leu Ser Pro Ala Ser Ser Ile Asn Gly Cys Ser Thr Asp
            115                 120                 125

Gly Glu Pro Arg Arg Gln Lys Lys Gly Pro Ala Pro Arg Gln Gln Glu
        130                 135                 140

Glu Leu Cys Leu Val Cys Gly Asp Arg Ala Ser Gly Tyr His Tyr Asn
145                 150                 155                 160

Ala Leu Thr Cys Glu Gly Cys Lys Gly Phe Phe Arg Arg Ser Val Thr
                165                 170                 175

Lys Asn Ala Val Tyr Ile Cys Lys Phe Gly His Ala Cys Glu Met Asp
            180                 185                 190

Met Tyr Met Arg Arg Lys Cys Gln Glu Cys Arg Leu Lys Lys Cys Leu
        195                 200                 205

Ala Val Gly Met Arg Pro Glu Cys Val Val Pro Glu Ser Thr Cys Lys
210                 215                 220

Asn Lys Arg Arg Glu Lys Glu Ala Gln Arg Glu Lys Asp Lys Leu Pro
225                 230                 235                 240

Val Ser Thr Thr Thr Val Asp Asp His Met Pro Ala Ile Met Gln Cys
                245                 250                 255

Asp Pro Pro Pro Pro Glu Ala Ala Arg Ile His Glu Val Val Pro Arg
            260                 265                 270

Phe Leu Thr Glu Lys Leu Met Glu Gln Asn Arg Leu Lys Asn Val Thr
        275                 280                 285

Pro Leu Ser Ala Asn Gln Lys Ser Leu Ile Ala Arg Leu Val Met Tyr
290                 295                 300
```

-continued

```
Gln Glu Gly Tyr Glu Gln Pro Ser Glu Glu Asp Leu Lys Arg Val Thr
305                 310                 315                 320

Gln Thr Trp Gln Leu Glu Glu Glu Glu Glu Thr Asp Met Pro
            325                 330                 335

Phe Arg Gln Ile Thr Glu Met Thr Ile Leu Thr Val Gln Leu Ile Val
            340                 345                 350

Glu Phe Ala Lys Gly Leu Pro Gly Phe Ser Lys Ile Ser Gln Ser Asp
            355                 360                 365

Gln Ile Thr Leu Leu Lys Ala Ser Ser Glu Val Met Met Leu Arg
            370                 375             380

Val Ala Arg Arg Tyr Asp Ala Ala Thr Asp Ser Val Leu Phe Ala Asn
385                 390                 395                 400

Asn Gln Ala Tyr Thr Arg Asp Asn Tyr Arg Lys Ala Gly Met Ser Tyr
                405                 410                 415

Val Ile Glu Asp Leu Leu His Phe Cys Arg Cys Met Tyr Ser Met Ser
                420                 425                 430

Met Asp Asn Val His Tyr Ala Leu Leu Thr Ala Ile Val Ile Phe Ser
            435                 440                 445

Asp Arg Pro Gly Leu Glu Gln Pro Leu Leu Val Glu Glu Ile Gln Arg
450                 455                 460

Tyr Tyr Leu Lys Thr Leu Arg Val Tyr Ile Leu Asn Gln His Ser Ala
465                 470                 475                 480

Ser Pro Arg Cys Ala Val Leu Phe Gly Lys Ile Leu Gly Val Leu Thr
                485                 490                 495

Glu Leu Arg Thr Leu Gly Thr Gln Asn Ser Asn Met Cys Ile Ser Leu
            500                 505                 510

Lys Leu Lys Asn Arg Lys Leu Pro Pro Phe Leu Glu Glu Ile Trp Asp
            515                 520                 525

Val Ala Glu Val Ser Thr Thr Gln Pro Thr Pro Gly Val Ala Ala Gln
            530                 535                 540

Val Thr Pro Ile Val Val Asp Asn Pro Ala Ala Leu
545                 550                 555

<210> SEQ ID NO 12
<211> LENGTH: 675
<212> TYPE: PRT
<213> ORGANISM: Aedes aegypti

<400> SEQUENCE: 12

Met Met Lys Arg Arg Trp Ser Asn Asn Gly Gly Phe Thr Ala Leu Arg
1               5                   10                  15

Met Leu Asp Asp Ser Ser Ser Glu Val Thr Ser Ser Ser Ala Ala Leu
            20                  25                  30

Gly Met Thr Met Ser Pro Asn Ser Leu Gly Ser Pro Asn Tyr Asp Glu
        35                  40                  45

Leu Glu Leu Trp Ser Ser Tyr Glu Asp Asn Ala Tyr Asn Gly His Ser
    50                  55                  60

Val Leu Ser Asn Gly Asn Asn Leu Gly Gly Cys Gly Ala Ala Asn
65              70                  75                  80

Asn Leu Leu Met Asn Gly Ile Val Gly Asn Asn Leu Asn Gly Met
            85                  90                  95

Met Asn Met Ala Ser Gln Ala Val Gln Ala Asn Ala Asn Ser Ile Gln
            100                 105                 110

His Ile Val Gly Asn Leu Ile Asn Gly Val Asn Pro Asn Gln Thr Leu
```

-continued

```
            115                 120                 125
Ile Pro Pro Leu Pro Ser Ile Ile Gln Asn Thr Leu Met Asn Thr Pro
    130                 135                 140
Arg Ser Glu Ser Val Asn Ser Ile Ser Ser Gly Arg Glu Asp Leu Ser
145                 150                 155                 160
Pro Ser Ser Ser Leu Asn Gly Tyr Thr Asp Gly Ser Asp Ala Lys Lys
                165                 170                 175
Gln Lys Lys Gly Pro Thr Pro Arg Gln Gln Glu Glu Leu Cys Leu Val
            180                 185                 190
Cys Gly Asp Arg Ala Ser Gly Tyr His Tyr Asn Ala Leu Thr Cys Glu
            195                 200                 205
Gly Cys Lys Gly Phe Phe Arg Arg Ser Val Thr Lys Asn Ala Val Tyr
    210                 215                 220
Cys Cys Lys Phe Gly His Ala Cys Glu Met Asp Met Tyr Met Arg Arg
225                 230                 235                 240
Lys Cys Gln Glu Cys Arg Leu Lys Lys Cys Leu Ala Val Gly Met Arg
                245                 250                 255
Pro Glu Cys Val Val Pro Glu Asn Gln Cys Ala Ile Lys Arg Lys Glu
            260                 265                 270
Lys Lys Ala Gln Lys Glu Lys Asp Lys Val Gln Thr Asn Ala Thr Val
    275                 280                 285
Ser Thr Thr Asn Ser Thr Tyr Arg Ser Glu Ile Leu Pro Ile Leu Met
    290                 295                 300
Lys Cys Asp Pro Pro His Gln Ala Ile Pro Leu Leu Pro Glu Lys
305                 310                 315                 320
Leu Leu Gln Glu Asn Arg Leu Arg Asn Ile Pro Leu Leu Thr Ala Asn
                325                 330                 335
Gln Met Ala Val Ile Tyr Lys Leu Ile Trp Tyr Gln Asp Gly Tyr Glu
            340                 345                 350
Gln Pro Ser Glu Glu Asp Leu Lys Arg Ile Met Ile Gly Ser Pro Asn
            355                 360                 365
Glu Glu Glu Asp Gln His Asp Val His Phe Arg His Ile Thr Glu Ile
    370                 375                 380
Thr Ile Leu Thr Val Gln Leu Ile Val Glu Phe Ala Lys Gly Leu Pro
385                 390                 395                 400
Ala Phe Thr Lys Ile Pro Gln Glu Asp Gln Ile Thr Leu Leu Lys Ala
                405                 410                 415
Cys Ser Ser Glu Val Met Met Leu Arg Met Ala Arg Arg Tyr Asp Ala
            420                 425                 430
Ala Thr Asp Ser Ile Leu Phe Ala Asn Asn Arg Ser Tyr Thr Arg Asp
            435                 440                 445
Ser Tyr Arg Met Ala Gly Met Ala Asp Thr Ile Glu Asp Leu Leu His
    450                 455                 460
Phe Cys Arg Gln Met Phe Ser Leu Thr Val Asp Asn Val Glu Tyr Ala
465                 470                 475                 480
Leu Leu Thr Ala Ile Val Ile Phe Ser Asp Arg Pro Gly Leu Glu Gln
                485                 490                 495
Ala Glu Leu Val Glu His Ile Gln Ser Tyr Tyr Ile Asp Thr Leu Arg
            500                 505                 510
Ile Tyr Ile Leu Asn Arg His Ala Gly Asp Pro Lys Cys Ser Val Ile
    515                 520                 525
Phe Ala Lys Leu Leu Ser Ile Leu Thr Glu Leu Arg Thr Leu Gly Asn
530                 535                 540
```

Gln Asn Ser Glu Met Cys Phe Ser Leu Lys Leu Lys Asn Arg Lys Leu
545                 550                 555                 560

Pro Arg Phe Leu Glu Glu Ile Trp Asp Val Gln Asp Ile Pro Pro Ser
                565                 570                 575

Met Gln Ala Gln Met His Ser His Gly Thr Gln Ser Ser Ser Ser Ser
            580                 585                 590

Ser Ser Ser Ser Ser Ser Ser Asn Gly Ser Ser Asn Gly Asn Ser
        595                 600                 605

Ser Ser Asn Ser Asn Ser Ser Gln His Gly Pro His Pro His
        610                 615                 620

Gly Gln Gln Leu Thr Pro Asn Gln Gln Gln His Gln Gln Gln His Ser
625                 630                 635                 640

Gln Leu Gln Gln Val His Ala Asn Gly Ser Gly Ser Gly Gly Ser
            645                 650                 655

Asn Asn Asn Ser Ser Ser Gly Gly Val Val Pro Gly Leu Gly Met Leu
            660                 665                 670

Asp Gln Val
        675

<210> SEQ ID NO 13
<211> LENGTH: 319
<212> TYPE: PRT
<213> ORGANISM: Heliothis virescens

<400> SEQUENCE: 13

Arg Pro Glu Cys Val Val Pro Glu Asn Gln Cys Ala Met Lys Arg Lys
1               5                   10                  15

Glu Lys Lys Ala Gln Arg Glu Lys Asp Lys Leu Pro Val Ser Thr Thr
            20                  25                  30

Thr Val Asp Asp His Met Pro Pro Ile Met Gln Cys Asp Pro Pro Pro
            35                  40                  45

Pro Glu Ala Ala Arg Ile Leu Glu Cys Val Gln His Glu Val Val Pro
        50                  55                  60

Arg Phe Leu Asn Glu Lys Leu Met Glu Gln Asn Arg Leu Lys Asn Val
65                  70                  75                  80

Pro Pro Leu Thr Ala Asn Gln Lys Ser Leu Ile Ala Arg Leu Val Trp
                85                  90                  95

Tyr Gln Glu Gly Tyr Glu Gln Pro Ser Glu Glu Asp Leu Lys Arg Val
            100                 105                 110

Thr Gln Ser Asp Glu Asp Asp Glu Asp Ser Asp Met Pro Phe Arg Gln
        115                 120                 125

Ile Thr Glu Met Thr Ile Leu Thr Val Gln Leu Ile Val Glu Phe Ala
        130                 135                 140

Lys Gly Leu Pro Gly Phe Ala Lys Ile Ser Gln Ser Asp Gln Ile Thr
145                 150                 155                 160

Leu Leu Lys Ala Cys Ser Ser Glu Val Met Met Leu Arg Val Ala Arg
                165                 170                 175

Arg Tyr Asp Ala Ala Thr Asp Ser Val Leu Phe Ala Asn Asn Gln Ala
            180                 185                 190

Tyr Thr Arg Asp Asn Tyr Arg Lys Ala Gly Met Ala Tyr Val Ile Glu
        195                 200                 205

Asp Leu Leu His Phe Cys Arg Cys Met Tyr Ser Met Met Met Asp Asn
        210                 215                 220

Val His Tyr Ala Leu Leu Thr Ala Ile Val Ile Phe Ser Asp Arg Pro

```
                     225                 230                 235                 240

Gly Leu Glu Gln Pro Leu Leu Val Glu Glu Ile Gln Arg Tyr Tyr Leu
                245                 250                 255

Asn Thr Leu Arg Val Tyr Ile Leu Asn Gln Asn Ser Ala Ser Pro Arg
            260                 265                 270

Gly Ala Val Ile Phe Gly Glu Ile Leu Gly Ile Leu Thr Glu Ile Arg
        275                 280                 285

Thr Leu Gly Met Gln Asn Ser Asn Met Cys Ile Ser Leu Lys Leu Lys
    290                 295                 300

Lys Arg Lys Leu Pro Pro Phe Leu Glu Glu Ile Asp Trp Asp Val
305                 310                 315

<210> SEQ ID NO 14
<211> LENGTH: 8
<212> TYPE: PRT
<213> ORGANISM: synthetic construct

<400> SEQUENCE: 14

Cys Glu Gly Cys Lys Gly Phe Phe
1               5

<210> SEQ ID NO 15
<211> LENGTH: 23
<212> TYPE: DNA
<213> ORGANISM: synthetic construct
<220> FEATURE:
<221> NAME/KEY: misc_feature
<222> LOCATION: (1)..(23)
<223> OTHER INFORMATION: y=c or t
<220> FEATURE:
<221> NAME/KEY: misc_feature
<222> LOCATION: (1)..(23)
<223> OTHER INFORMATION: r=g or a
<220> FEATURE:
<221> NAME/KEY: misc_feature
<222> LOCATION: (1)..(23)
<223> OTHER INFORMATION: n=inosine

<400> SEQUENCE: 15
tgygarggnt gyaargantt ytt                                              23

<210> SEQ ID NO 16
<211> LENGTH: 8
<212> TYPE: PRT
<213> ORGANISM: synthetic construct
<220> FEATURE:
<221> NAME/KEY: MISC_FEATURE
<222> LOCATION: (3)..(3)
<223> OTHER INFORMATION: Xaa=E or S
<220> FEATURE:
<221> NAME/KEY: MISC_FEATURE
<222> LOCATION: (6)..(6)
<223> OTHER INFORMATION: Xaa=L or R

<400> SEQUENCE: 16

Cys Gln Xaa Cys Arg Xaa Lys Lys
1               5

<210> SEQ ID NO 17
<211> LENGTH: 23
<212> TYPE: DNA
<213> ORGANISM: synthetic construct
<220> FEATURE:
<221> NAME/KEY: misc_feature
<222> LOCATION: (1)..(23)
<223> OTHER INFORMATION: r=g or a
<220> FEATURE:
```

```
<221> NAME/KEY: misc_feature
<222> LOCATION: (1)..(23)
<223> OTHER INFORMATION: y=c or t
<220> FEATURE:
<221> NAME/KEY: misc_feature
<222> LOCATION: (1)..(23)
<223> OTHER INFORMATION: n=inosine

<400> SEQUENCE: 17
ttyttnagnc grcaytcytg rca                                              23

<210> SEQ ID NO 18
<211> LENGTH: 23
<212> TYPE: DNA
<213> ORGANISM: synthetic construct
<220> FEATURE:
<221> NAME/KEY: misc_feature
<222> LOCATION: (1)..(23)
<223> OTHER INFORMATION: r=g or a
<220> FEATURE:
<221> NAME/KEY: misc_feature
<222> LOCATION: (1)..(23)
<223> OTHER INFORMATION: y=c or t
<220> FEATURE:
<221> NAME/KEY: misc_feature
<222> LOCATION: (1)..(23)
<223> OTHER INFORMATION: n=inosine

<400> SEQUENCE: 18
ttyttnaanc grcaytcytg rca                                              23

<210> SEQ ID NO 19
<211> LENGTH: 23
<212> TYPE: DNA
<213> ORGANISM: synthetic construct
<220> FEATURE:
<221> NAME/KEY: misc_feature
<222> LOCATION: (1)..(23)
<223> OTHER INFORMATION: r=g or a
<220> FEATURE:
<221> NAME/KEY: misc_feature
<222> LOCATION: (1)..(23)
<223> OTHER INFORMATION: y=c or t
<220> FEATURE:
<221> NAME/KEY: misc_feature
<222> LOCATION: (1)..(23)
<223> OTHER INFORMATION: n=inosine

<400> SEQUENCE: 19
ttyttnagnc trcaytcytg rca                                              23

<210> SEQ ID NO 20
<211> LENGTH: 23
<212> TYPE: DNA
<213> ORGANISM: synthetic construct
<220> FEATURE:
<221> NAME/KEY: misc_feature
<222> LOCATION: (1)..(23)
<223> OTHER INFORMATION: r=g or a
<220> FEATURE:
<221> NAME/KEY: misc_feature
<222> LOCATION: (1)..(23)
<223> OTHER INFORMATION: y=c or t
<220> FEATURE:
<221> NAME/KEY: misc_feature
<222> LOCATION: (1)..(23)
<223> OTHER INFORMATION: n=inosine

<400> SEQUENCE: 20
ttyttnaanc trcaytcytg rca                                              23
```

<210> SEQ ID NO 21
<211> LENGTH: 39
<212> TYPE: DNA
<213> ORGANISM: synthetic construct

<400> SEQUENCE: 21
aattaagctt ccaccatgcc gttaccaatg ccaccgaca                     39

<210> SEQ ID NO 22
<211> LENGTH: 20
<212> TYPE: DNA
<213> ORGANISM: synthetic construct

<400> SEQUENCE: 22
cttcaaccga cactcctgac                                          20

<210> SEQ ID NO 23
<211> LENGTH: 22
<212> TYPE: DNA
<213> ORGANISM: synthetic construct

<400> SEQUENCE: 23
cagctccagg ccgccgatct cg                                       22

<210> SEQ ID NO 24
<211> LENGTH: 48
<212> TYPE: DNA
<213> ORGANISM: synthetic construct
<220> FEATURE:
<221> NAME/KEY: misc_feature
<222> LOCATION: (1)..(48)
<223> OTHER INFORMATION: n=inosine

<400> SEQUENCE: 24
cuacuacuac uaggccacgc gtcgactagt acgggnnggg nnggtnng            48

<210> SEQ ID NO 25
<211> LENGTH: 32
<212> TYPE: DNA
<213> ORGANISM: synthetic construct

<400> SEQUENCE: 25
caucaucauc auggccacgc gtcgactagt ac                            32

<210> SEQ ID NO 26
<211> LENGTH: 27
<212> TYPE: DNA
<213> ORGANISM: synthetic construct

<400> SEQUENCE: 26
acgtcacctc agacgagctc tccattc                                  27

<210> SEQ ID NO 27
<211> LENGTH: 24
<212> TYPE: DNA
<213> ORGANISM: synthetic construct

<400> SEQUENCE: 27
cgctggtata acaacggacc attc                                     24

<210> SEQ ID NO 28
<211> LENGTH: 48
<212> TYPE: DNA
<213> ORGANISM: synthetic construct -continued

```
<400> SEQUENCE: 28
attaagcttg ccgccatgcg ccgacgctgg tataacaacg gaccattc          48

<210> SEQ ID NO 29
<211> LENGTH: 39
<212> TYPE: DNA
<213> ORGANISM: synthetic construct

<400> SEQUENCE: 29
attaagcttg ccgccatgtc cctcggcgct cgtggatac                    39

<210> SEQ ID NO 30
<211> LENGTH: 137
<212> TYPE: DNA
<213> ORGANISM: synthetic construct

<400> SEQUENCE: 30
ctagtagaca agggttcaat gcacttgtcc aataagctta gacaagggtt caatgcactt    60
gtccaatgaa ttcagacaag ggttcaatgc acttgtccaa tctgcagaga caagggttca   120
atgcacttgt ccaatat                                                  137

<210> SEQ ID NO 31
<211> LENGTH: 135
<212> TYPE: DNA
<213> ORGANISM: synthetic construct

<400> SEQUENCE: 31
cgatattgga caagtgcatt gaaccttgt ctctgcagat tggacaagtg cattgaaccc     60
ttgtctgaat tcattggaca agtgcattga accttgtct aagcttattg gacaagtgca    120 ttgaacccctt gtcta                                                  135

<210> SEQ ID NO 32
<211> LENGTH: 38
<212> TYPE: DNA
<213> ORGANISM: synthetic construct

<400> SEQUENCE: 32
attgaattcc accatggact ccaaagaatc attaactc                     38

<210> SEQ ID NO 33
<211> LENGTH: 42
<212> TYPE: DNA
<213> ORGANISM: synthetic construct

<400> SEQUENCE: 33
gagactcctg tagtggcctc gagcattcct tttattttt tc                 42

<210> SEQ ID NO 34
<211> LENGTH: 31
<212> TYPE: DNA
<213> ORGANISM: synthetic construct

<400> SEQUENCE: 34
attctcgaga ttcagcaggc cactacagga g                            31

<210> SEQ ID NO 35
<211> LENGTH: 32
<212> TYPE: DNA
<213> ORGANISM: synthetic construct

<400> SEQUENCE: 35
```

```
attgaattca atgctatcgt aactatacag gg                                    32

<210> SEQ ID NO 36
<211> LENGTH: 35
<212> TYPE: DNA
<213> ORGANISM: synthetic construct

<400> SEQUENCE: 36
attgtcgaca acggccggaa tggctcgtcc cggag                                 35

<210> SEQ ID NO 37
<211> LENGTH: 48
<212> TYPE: DNA
<213> ORGANISM: synthetic construct

<400> SEQUENCE: 37
tcgggctttg ttaggatcct aagccgtggt cgaatgctcc gacttaac                   48

<210> SEQ ID NO 38
<211> LENGTH: 35
<212> TYPE: DNA
<213> ORGANISM: synthetic construct

<400> SEQUENCE: 38
attgtcgaca aaggcccgag tgcgtggtgc cggag                                 35

<210> SEQ ID NO 39
<211> LENGTH: 24
<212> TYPE: DNA
<213> ORGANISM: synthetic construct

<400> SEQUENCE: 39
tcacattgca tgatgggagg catg                                             24

<210> SEQ ID NO 40
<211> LENGTH: 82
<212> TYPE: DNA
<213> ORGANISM: synthetic construct

<400> SEQUENCE: 40
agcttcgact gtacaggatg ttctagctac tcgagtagct agaacatcct gtacagtcga      60
gtagctagaa catcctgtac ag                                               82

<210> SEQ ID NO 41
<211> LENGTH: 82
<212> TYPE: DNA
<213> ORGANISM: synthetic construct

<400> SEQUENCE: 41
tcgactgtac aggatgttct agctactcga ctgtacagga tgttctagct actcgagtcg      60
ctagaacatc ctgtacagtc ga                                               82

<210> SEQ ID NO 42
<211> LENGTH: 78
<212> TYPE: DNA
<213> ORGANISM: synthetic construct

<400> SEQUENCE: 42
tcgactagct agaacatcct gtacagtcga gtagctagaa catcctgtac agtcgagtag      60
ctagaacatc ctgtacag                                                    78
```

-continued

```
<210> SEQ ID NO 43
<211> LENGTH: 78
<212> TYPE: DNA
<213> ORGANISM: synthetic construct

<400> SEQUENCE: 43
gatcctgtac aggatgttct agctactcga ctgtacagga tgttctagct actcgactgt    60
acaggatgtt ctagctag                                                  78

<210> SEQ ID NO 44
<211> LENGTH: 104
<212> TYPE: DNA
<213> ORGANISM: synthetic construct

<400> SEQUENCE: 44
ctagttgtac aggatgttct agctactcga gtagctagaa catcctgtac agtcgagtag    60
ctagaacatc ctgtacagtc gagtagctag aacatcctgt acac                    104

<210> SEQ ID NO 45
<211> LENGTH: 104
<212> TYPE: DNA
<213> ORGANISM: synthetic construct

<400> SEQUENCE: 45
ttaagtgtac aggatgttct agctactcga ctgtacagga tgttctagct actcgactgt    60
acaggatgtt ctagctactc gagtagctag aacatcctgt acaa                    104

<210> SEQ ID NO 46
<211> LENGTH: 15
<212> TYPE: DNA
<213> ORGANISM: synthetic construct

<400> SEQUENCE: 46
cattggatcc ttagc                                                     15

<210> SEQ ID NO 47
<211> LENGTH: 23
<212> TYPE: DNA
<213> ORGANISM: synthetic construct

<400> SEQUENCE: 47
ggccgctaag gatccaatgg gcc                                            23

<210> SEQ ID NO 48
<211> LENGTH: 32
<212> TYPE: DNA
<213> ORGANISM: synthetic construct

<400> SEQUENCE: 48
aattccatgg tacgacgaca gtagacgatc ac                                  32

<210> SEQ ID NO 49
<211> LENGTH: 29
<212> TYPE: DNA
<213> ORGANISM: synthetic construct

<400> SEQUENCE: 49
ctgaggtcta gagacggtgg cgggcggcc                                      29

<210> SEQ ID NO 50
<211> LENGTH: 31
```

```
<212> TYPE: DNA
<213> ORGANISM: synthetic construct

<400> SEQUENCE: 50
atatgaattc caccatggac tccaaagaat c                              31

<210> SEQ ID NO 51
<211> LENGTH: 36
<212> TYPE: DNA
<213> ORGANISM: synthetic construct

<400> SEQUENCE: 51
atatgctagc tgtgggggca gcagacacag cagtgg                         36

<210> SEQ ID NO 52
<211> LENGTH: 33
<212> TYPE: DNA
<213> ORGANISM: synthetic construct

<400> SEQUENCE: 52
atatgctagc tccagctcct caacagcaac aac                            33

<210> SEQ ID NO 53
<211> LENGTH: 30
<212> TYPE: DNA
<213> ORGANISM: synthetic construct

<400> SEQUENCE: 53
atatctcgag caattccttt tattttttc                                 30

<210> SEQ ID NO 54
<211> LENGTH: 30
<212> TYPE: DNA
<213> ORGANISM: synthetic construct

<400> SEQUENCE: 54
attactagtt ctgcggcccc cccgaccgat                                30

<210> SEQ ID NO 55
<211> LENGTH: 31
<212> TYPE: DNA
<213> ORGANISM: synthetic construct

<400> SEQUENCE: 55
aattactagt cccaccgtac tcgtcaattc c                              31

<210> SEQ ID NO 56
<211> LENGTH: 32
<212> TYPE: DNA
<213> ORGANISM: synthetic construct
<220> FEATURE:
<221> NAME/KEY: misc_feature
<222> LOCATION: (1)..(32)
<223> OTHER INFORMATION: n=inosine
<220> FEATURE:
<221> NAME/KEY: misc_feature
<222> LOCATION: (1)..(32)
<223> OTHER INFORMATION: w=t or a
<220> FEATURE:
<221> NAME/KEY: misc_feature
<222> LOCATION: (1)..(32)
<223> OTHER INFORMATION: k=g or t

<400> SEQUENCE: 56
attgctcgag aaagnccnga gwgcktngtn cc                             32
```

```
<210> SEQ ID NO 57
<211> LENGTH: 32
<212> TYPE: DNA
<213> ORGANISM: synthetic construct
<220> FEATURE:
<221> NAME/KEY: misc_feature
<222> LOCATION: (1)..(32)
<223> OTHER INFORMATION: n=inosine
<220> FEATURE:
<221> NAME/KEY: misc_feature
<222> LOCATION: (1)..(32)
<223> OTHER INFORMATION: w=t or a
<220> FEATURE:
<221> NAME/KEY: misc_feature
<222> LOCATION: (1)..(32)
<223> OTHER INFORMATION: s=g or c

<400> SEQUENCE: 57
attgctcgag aacgnccnga gwgtstngtn cc                                      32

<210> SEQ ID NO 58
<211> LENGTH: 33
<212> TYPE: DNA
<213> ORGANISM: synthetic construct
<220> FEATURE:
<221> NAME/KEY: misc_feature
<222> LOCATION: (1)..(33)
<223> OTHER INFORMATION: n=inosine
<220> FEATURE:
<221> NAME/KEY: misc_feature
<222> LOCATION: (1)..(33)
<223> OTHER INFORMATION: w=t or a
<220> FEATURE:
<221> NAME/KEY: misc_feature
<222> LOCATION: (1)..(33)
<223> OTHER INFORMATION: y=t or c

<400> SEQUENCE: 58
ttactcgagn acgwcccana tctctycnag gaa                                     33

<210> SEQ ID NO 59
<211> LENGTH: 33
<212> TYPE: DNA
<213> ORGANISM: synthetic construct
<220> FEATURE:
<221> NAME/KEY: misc_feature
<222> LOCATION: (1)..(33)
<223> OTHER INFORMATION: n=inosine
<220> FEATURE:
<221> NAME/KEY: misc_feature
<222> LOCATION: (1)..(33)
<223> OTHER INFORMATION: w=t or a
<220> FEATURE:
<221> NAME/KEY: misc_feature
<222> LOCATION: (1)..(33)
<223> OTHER INFORMATION: y=c or t

<400> SEQUENCE: 59
ttactcgagn acgwcccana tctcctynaa gaa                                     33

<210> SEQ ID NO 60
<211> LENGTH: 116
<212> TYPE: DNA
<213> ORGANISM: Heliothis virescens

<400> SEQUENCE: 60
tactcttggc attttctccg catatacata tccatttcgc aagcatggcc gaatttgcat        60
atgtacactg cattttggt tacactccgc ctgaagaact ccttgcaccc ctcgca            116
```

-continued

```
<210> SEQ ID NO 61
<211> LENGTH: 1934
<212> TYPE: DNA
<213> ORGANISM: Heliothis virescens

<400> SEQUENCE: 61
ccgtacgaaa tcgggtacgg gtgtgccctc ttaagtggta aaattcgcag tccttataaa     60
taggttgatc acgtcgacgt cagtgtccgt gcacttcact aaaactagcc agtctatgag    120
cgttctctcc tgaggcgcgc tagacggtgg cgggcggccg ggcgggcggg gcgggggcta    180
gaggcgccgg cgcctccgcc gccaccggcg tcgccgtcgt cgccacgtcc gccacgtccc    240
agatctcctc gaggaacggc ggcagcttcc tgttcttcag cttgagggag atgcacatgt    300
tggagttctg catgcccagc gtgcggatct ccgtcagtat gcccaggatc tcgccgaaga    360
tgacggcgcc gcggggcgac gcgctgttct ggttcaggat gtacacccgt agcgtgttca    420
ggtaatatct ctggatgtcc tccaccaaca ggggttgctc aagcccgggc cggtctgaga    480
agatgacaat ggctgtaagc agcgcataat gcacgttatc catcatcatg gagtacatgc    540
accgacagaa gtgcagcagg tcctcgatga cgtacgccat gcctgccttg cggtagttgt    600
cgcgagtgta cgcctggttg ttcgcgaaca gtacgctgtc ggtggccgcg tcataccgcc    660
gagccactcg gagcatcatc acctcacttg agcacgcctt taataacgtg atctggtccg    720
actgcgagat cttggcgaag cccgggaggc ccttagcgaa ttctacgatg agctgcactg    780
tgagaatcgt catctcggta atctgacgga acggcatatc cgagtcttcg tcgtcctcgt    840
ccgactgtgt aaccctcttc aggtcttcct cggaaggttg ttcatagcct tcctggtacc    900
acacgagcct tgcgatcaac gacttctgat tggcagtgag gggggcacg ttcttcaatc     960 tgttctgttc cattagcttc tcattcagga atcgtggcac cacctcgtgc tgcacacatt   1020
ccagaattct agcggcctct gggggcggag ggtcacattg catgatggga ggcatgtgat   1080
cgtctactgt cgtcgtactg acgggcaatt tgtctttttc cctctgcgcc tttttctctt   1140
tccgtttcat tgcacactgg ttctccggca ccacgcactc gggcctcatg cccaccgcaa   1200
gacatttctt caaccgacac tcctgacatt ttctccgcat atagatatcc atttcgcaag   1260
catggccgaa tttgcatatg tacactgcat ttttggttac actccgcctg aagaaacctt   1320
tacacccttc acatgtgagc gcgttgtagt gatatccgga ggctctgtcg ccgcagacaa   1380
gacatagctc ttcttgctgc ctcggcgctg ggcctttctt ctgccgcctc gcctcgccat   1440
ctgtgctgca gccgtttaca ctcgaagctg gagacagttc ctcacgacct gatgacattg   1500
actcgttttc tgatttgggt gttgtcggtg gcattggtaa cggcatggaa ggtaggggtt   1560
gtgtctgctg caggttagct agctgcggct ggggaattcc gcgggaatga tattctgctg   1620
agcaccacgg ccatcacgcc acagtttacc agagggtcca tccactgtct tctgggtggc   1680
agtggtggcg tgtacagtgg tcatcagacc ttcaatgatc tcgaagttgt catggatgac   1740
cttagcgaga ggagcgaggc agttggttgt gcaggaggcg ttggagatga ccttgtaaga   1800
ggggtcatac tgcttcaagg ttgacaccaa cgacgaacat gggtcagcgc tgggcagcag   1860
gagatgatga ccttcttagc accaccctct aaatgagcag aggccttttc tgtggtggtg   1920
aaaacaccag tgga                                                     1934

<210> SEQ ID NO 62
<211> LENGTH: 2464
<212> TYPE: DNA
<213> ORGANISM: Heliothis virescens
<220> FEATURE:
```

<210> NAME/KEY: misc_feature
<222> LOCATION: (224)..(224)
<223> OTHER INFORMATION: n = a, c, g, or t, or i

<400> SEQUENCE: 62

```
gaagttccgg gtcgagtgtc catgtcagta aatcacttaa acaaaaggct tgctcgtgtg      60
gaagctatcg acgacacaca ctttgtattg taataagaca cacttatatc accctatggt     120
agataatcaa cacattaaaa tgtaatcaca gcaataaatt aaattactca tttagtcgag     180
ggtcgcgggc acaggacgat ggaaccatga aacacgataa cgcncctcac gtgtgcatca     240
gaaacaaaca tgtgacggcg acgtggacag cggacgactc atcacaatat tatactcgaa     300
aggttaatca acgtattatt gttaattttg gtaaataaac ataactatca acttttcacc     360
caatagaaac atcttcttct tatattcttt gtctctaata actctcgtaa gctacgtacg     420
tatgtgtaat ttagtaggtg tacttatcga acgaagtctt atcatacagt cgtatccgag     480
tgaccaactc agtcgtaaac gaaataaaac tgaagccgcg ggcgccgcga tcgccgccga     540
ccggcgacgg cgtgcgggcc cgaacagcaa caccaatata tattctccaa atcgttcaac     600
aacacatata ttcacattac acacgctctg catcgtcgtc ggtcaccgaa tacgtacgaa     660
atcgggtacg ggtgtgccct cttaagtggt aaaattcgca gtccttataa ataggttgat     720
cacgtcgacg tcagtgtccg tgcacttcac taaaactagc cagtctatga gcgttctctc     780
ctgaggcgcg ctagacggtg gcggcggcc gggcgggcgg ggcggggct agaggcgccg       840
gcgcctccgc cgccaccggc gtcgccgtcg tcgccacgtc cgccacgtcc cagatctcct     900
cgaggaacgg cggcagcttc ctgttcttca gcttgaggga gatgcacatg ttggagttct     960
gcatgcccag cgtgcggatc tccgtcagta tgcccaggat ctcgccgaag atgacggcgc    1020
cgcggggcga cgcgctgttc tggttcagga tgtacacccg tagcgtgttc aggtaatatc    1080
tctggatgtc ctccaccaac aggggttgct caagcccggg ccggtctgag aagatgacaa    1140
tggctgtaag cagcgcataa tgcacgttat ccatcatcat ggagtacatg caccgacaga    1200
agtgcagcag gtcctcgatg acgtacgcca tgcctgcctt gcggtagttg tcgcgagtgt    1260
acgcctggtt gttcgcgaac agtacgctgt cggtggccgc gtcataccgc cgagccactc    1320
ggagcatcat cacctcactt gagcacgcct ttaataacgt gatctggtcc gactgcgaga    1380
tcttggcgaa gcccgggagg cccttagcga attctacgat gagctgcact gtgagaatcg    1440
tcatctcggt aatctgacgg aacggcatat ccgagtcttc gtcgtcctcg tccgactgtg    1500
taaccctctt caggtcttcc tcggaaggtt gttcatagcc ttcctggtac cacacgagcc    1560
ttgcgatcaa cgacttctga ttggcagtga ggggggggcac gttcttcaat ctgttctgtt    1620
ccattagctt ctcattcagg aatcgtggca ccacctcgtg ctgcacacat tccagaattc    1680
tagcggcctc tggggcgga gggtcacatt gcatgatggg aggcatgtga tcgtctactg    1740
tcgtcgtact gacgggcaat ttgtcttttt ccctctgcgc ctttttctct ttccgtttca    1800
ttgcacactg gttctccggc caccgcact cgggcctcat gcccaccgca agacatttct    1860
tcaaccgaca ctcctgacat tttctccgca tatagatatc catttcgcaa gcatggccga    1920
atttgcatat gtacactgca tttttggtta cactccgcct gaagaaacct ttacacctt    1980
cacatgtgag cgcgttgtag tgatatccgg aggctctgtc gccgcagaca agacatagct    2040
cttcttgctg cctcggcgct gggcttttct tctgccgcct cgcctcgcca tctgtgctgc    2100
agccgtttac actcgaagct ggagacagtt cctcacgacc tgatgacatt gactcgtttt    2160
ctgatttggg tgttgtcggt ggcattggta acggcatgga aggtagggt tgtgtctgct    2220
```

```
gcggctgctg ctgcggctgg ggctgctgct gctccatggt gcaggtgccc agcgactgtg     2280
ccatgctgta agtgatgcca tcgtcgtagc cccacagctc caggccgccg atctcgggcg     2340
acgcgagcga ttccggggac atcaccatag ccggcggcag gcccagtgct gaagacgacg     2400
tcacctcaga cgagctctcc tcgagcattc gcagcgtctg gaatggtccg ttgttatacc     2460
agcg                                                                 2464

<210> SEQ ID NO 63
<211> LENGTH: 948
<212> TYPE: DNA
<213> ORGANISM: Spodoptera exigua

<400> SEQUENCE: 63
ttttactcga ggacgtccca gatatcctcg aagaacggcg gcacgttcct gttcttcagc       60
ttgagtgaga tgcacatgtt ggagttctgc atgcccaggg tccgcagctc cgtcaggatg      120
ccgaggatct tagcgtagat gacagggcag cacggcgacc gactgttctg gttcaggatg      180
tacacccgca gcgtgttcag gtaatatctc tggatctcct ccaccaacag ggttagctca      240
agcccgggtc ggtctgagaa aatgacgatg gcagtgagca gtgcatagtg gacgttatcc      300
atcatcatgg agtacatgca ccggcagaag tgcagcaggt cctcgatgac gtaggccatg      360
cctgccttgc ggtagttgtc gcgggtgtac gcctggttgt tggcgaacaa cacgctgtct      420
gtcgccgcgt cgtaccgccg agctactcgc aacatcatca cctcactcga acaggccttt      480
aataatgtga tctgatccga ctgtgagatc tttgcgaacg ctggtaggcc cttagcgaat      540
tcaacaatga gctgcactgt gaggatcgtc atctcggtga tctgacggaa cggcatgtcc      600
gactcttctt cgtcttcatc cgactgtgtg actcttttta gatcctcttc tgatggctgt      660
tcatagcctt cttggtacca gaccagcctc gctattaagg acttctggtt ggcagtgagg      720
gggcacattc ttgagccttg tcctgtccat tagcttttca ttcaggaatc gtggcaccac      780
ctcgtgaatt cttgcggcct ctggaggcgg tggatcacac tgcataatgg gaggcatgtg      840
atcatccact gtcgttgtac tgactggcaa cttgtctttt tccctttgtg ccttttctc       900 tttccttttc attgcacact ggttttctgg caccacgcac tccggcct                  948
```